US010982216B2

(12) United States Patent
Tesar et al.

(10) Patent No.: US 10,982,216 B2
(45) Date of Patent: Apr. 20, 2021

(54) METHODS AND COMPOSITIONS FOR ENHANCING FUNCTIONAL MYELIN PRODUCTION

(71) Applicant: Case Western Reserve University, Cleveland, OH (US)

(72) Inventors: Paul Tesar, Wickliffe, OH (US); Matthew Elitt, Shaker Heights, OH (US)

(73) Assignee: Case Western Reserve University, Cleveland, OH (US)

( * ) Notice: Subject to any disclaimer, the term of this patent is extended or adjusted under 35 U.S.C. 154(b) by 0 days.

(21) Appl. No.: 16/857,652

(22) Filed: Apr. 24, 2020

(65) Prior Publication Data
US 2020/0299701 A1    Sep. 24, 2020

Related U.S. Application Data

(63) Continuation of application No. 16/467,428, filed as application No. PCT/US2017/064870 on Dec. 6, 2017.

(60) Provisional application No. 62/542,660, filed on Aug. 8, 2017, provisional application No. 62/431,787, filed on Dec. 8, 2016.

(51) Int. Cl.
*C12N 15/63* (2006.01)
*C07K 14/47* (2006.01)
*C12N 15/10* (2006.01)

(52) U.S. Cl.
CPC .......... *C12N 15/63* (2013.01); *C07K 14/4713* (2013.01); *C12N 15/102* (2013.01); *C12N 2310/20* (2017.05); *C12N 2750/14143* (2013.01)

(58) Field of Classification Search
CPC .. C12N 15/63; C12N 15/102; C12N 2310/20; C12N 2750/14143; C07K 14/4713; A61P 7/00; A61P 3/00; A61P 27/02; A61P 25/28; A61P 25/16; A61P 25/14; A61P 25/04; A61P 25/00; A61P 21/02
See application file for complete search history.

(56) References Cited

U.S. PATENT DOCUMENTS

| 8,415,106 B2 | 4/2013 | Popko et al. | |
|---|---|---|---|
| 2012/0059042 A1* | 3/2012 | Platenburg | A61P 43/00 514/44 A |
| 2020/0040345 A1 | 2/2020 | Tesar et al. | |

FOREIGN PATENT DOCUMENTS

JP          2010-43025 A      2/2010

OTHER PUBLICATIONS

Regis et al. (PLOS One (2013) vol. 8(9), e 736333, pp. 1-6) (Year: 2013).*
Barrie et al., Modulation of rumpshaker phenotype with wild-type PLP/DM20 suggests several pathogenic mechanisms. J Neurosci Res. Aug. 1, 2010;88(10):2135-45.
Cailloux et al., Genotype-phenotype correlation in inherited brain myelination defects due to proteolipid protein gene mutations. Clinical European Network on Brain Dysmyelinating Disease. Eur J Hum Genet. Nov. 2000;8(11):837-45.
Edgar et al., Oligodendroglial modulation of fast axonal transport in a mouse model of hereditary spastic paraplegia. J Cell Biol. Jul. 5, 2004;166(1):121-31
Osorio et al., Stem Cell-Based Treatment of Pelizaeus-Merzbacher Disease. Stem Cells. Feb. 2017;35(2):311-315.
Stecca et al., The evolution of lipophilin genes from invertebrates to tetrapods: DM-20 cannot replace proteolipid protein in CNS myelin. J Neurosci. Jun. 1, 2000;20(11):4002-10.
International Search Report and Written Opinion for Application No. PCT/US2017/064870, dated Mar. 20, 2018, 11 pages.
Garbern et al., The molecular pathogenesis of Pelizaeus-Merzbacher disease. Arch Neurol. Oct. 1995;56(10):1210-4.
Yang et al., Proteolipid protein regulates the survival and differentiation of oligodendrocytes. J Neurosci. Mar. 15, 1997;17(6):2056-70.
U.S. Appl. No. 16/467,428, filed Jun. 6, 2019, 2020-0040345, Published.
Elitt et al., Suppression of proteolipid protein rescues Pelizaeus-Merzbacher disease. Nature. Sep. 2020;585(7825):397-403.
Jafar-Nejad et al., The atlas of RNase H antisense oligonucleotide distribution and activity in the CNS of rodents and non-human primates following central administration. bioRxiv preprint doi: https://doi.org/10.1101/2020.07.31.216721. 35 pages, Aug. 2, 2020.
Karim et al., PLP/DM20 expression and turnover in a transgenic mouse model of Pelizaeus-Merzbacher disease. Glia. Nov. 1, 2010;58(14):1727-38.

* cited by examiner

Primary Examiner — J. E. Angell
(74) Attorney, Agent, or Firm — McCarter & English, LLP; Steven G. Davis

(57) ABSTRACT

A method of generating a cell that enhances functional myelin production is provided, the method including genetically modifying the cell such that: (i) an endogenous PLP1 gene is modified to decrease its ability to inhibit myelin production; (ii) an endogenous PLP1 genetic regulatory element is modified to decrease its ability to promote PLP1 expression; (iii) an endogenous PLP1 genetic regulatory element is modified to increase its ability to inhibit PLP1 expression; or (iv) an endogenous PLP1 gene product or a PLP1 regulatory element gene product that promotes PLP1 expression is modified to decrease the PLP1 expression level, wherein the cell produces functional myelin.

8 Claims, 11 Drawing Sheets

Specification includes a Sequence Listing.

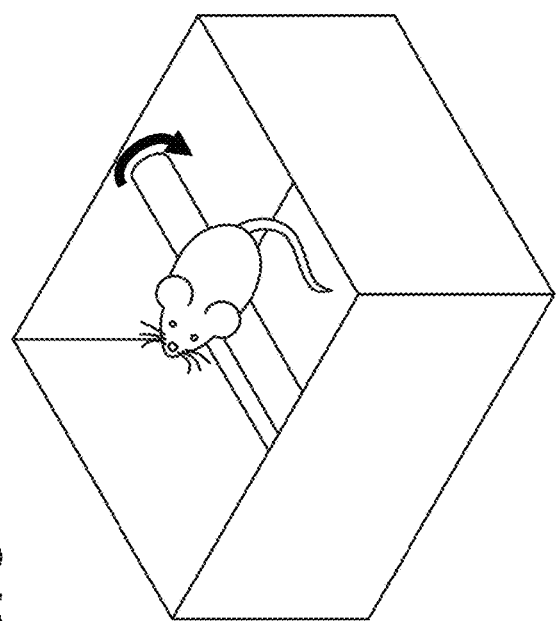
FIG. 8
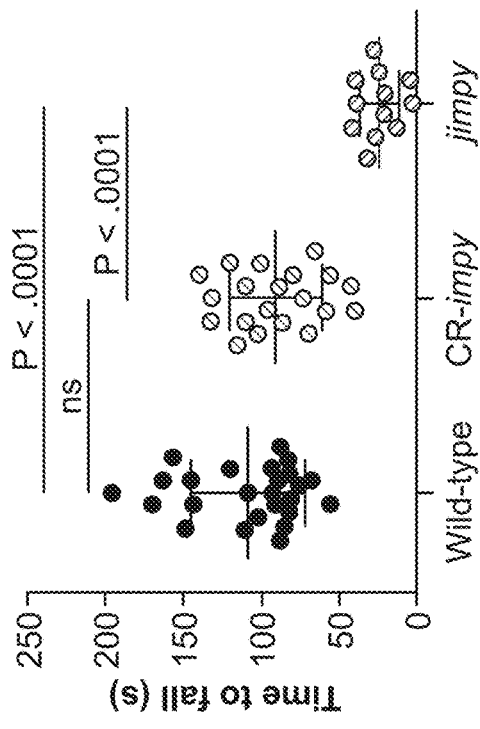
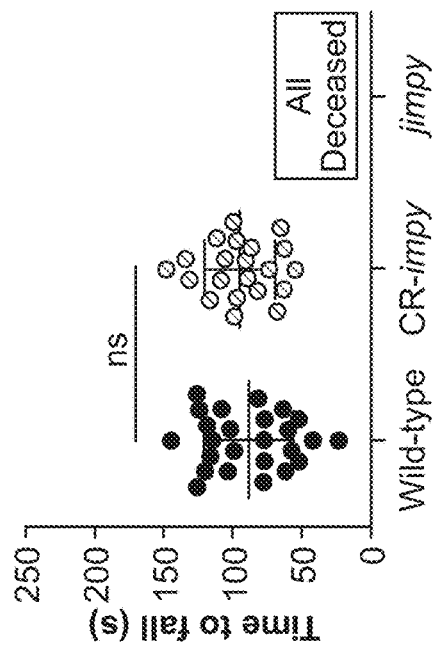
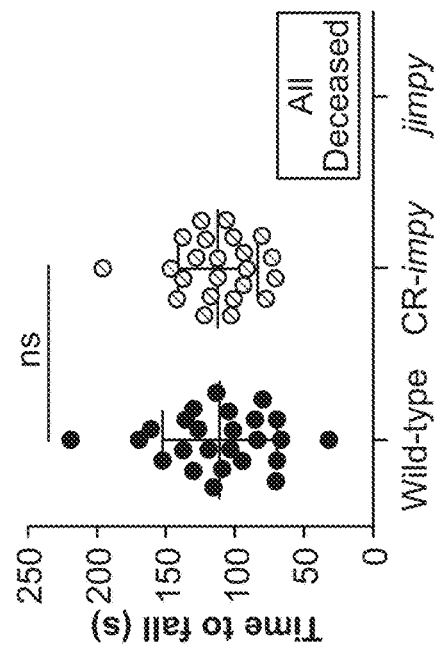

FIG. 11
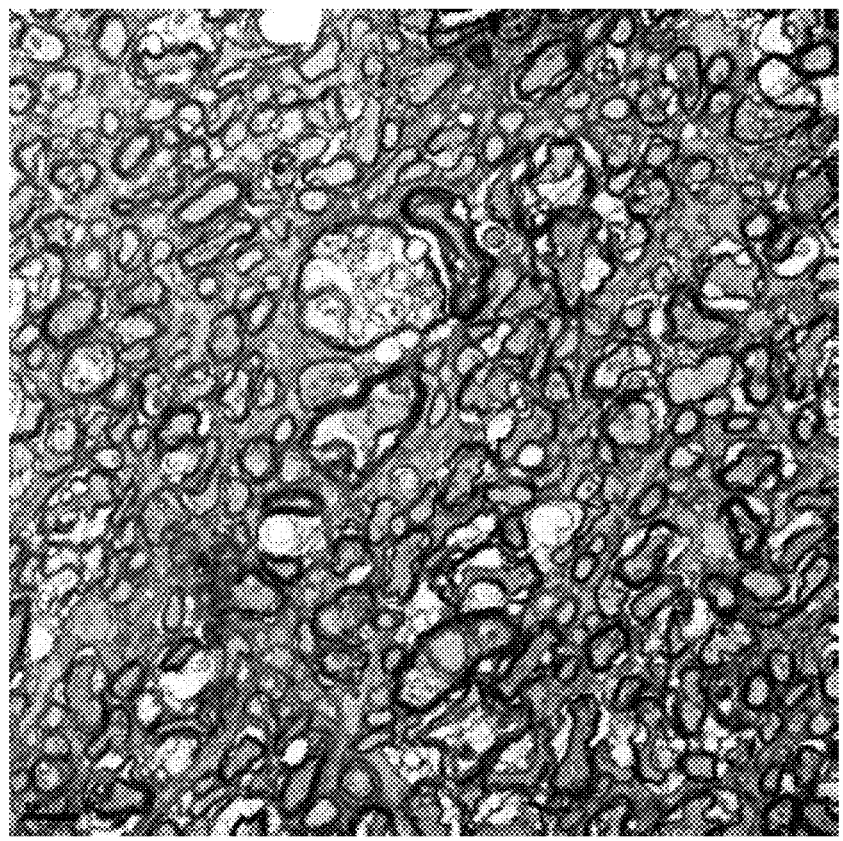
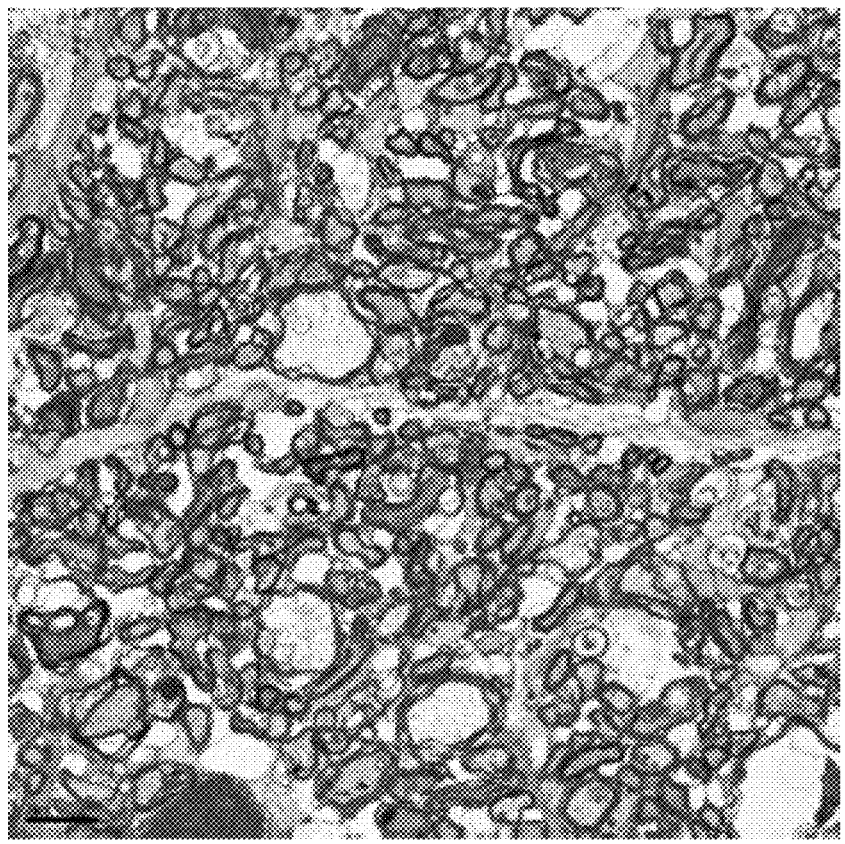

SEQUENCE LISTING

```
<160> NUMBER OF SEQ ID NOS: 6

<210> SEQ ID NO 1
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (21)..(21)
```

```
<223> OTHER INFORMATION: a, c, t, g, unknown or other

<400> SEQUENCE: 1
aagaccacca tctgcggcaa ngg                                              23

<210> SEQ ID NO 2
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (21)..(21)
<223> OTHER INFORMATION: a, c, t, g, unknown or other

<400> SEQUENCE: 2
ccagcaggag ggccccataa ngg                                              23

<210> SEQ ID NO 3
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (22)..(23)
<223> OTHER INFORMATION: a, c, t, g, unknown or other

<400> SEQUENCE: 3
gtcagagtgc caaagacatg gnngrrt                                          27

<210> SEQ ID NO 4
<211> LENGTH: 25
<212> TYPE: DNA
<213> ORGANISM: Homo sapiens

<400> SEQUENCE: 4
ctgacctctt ctcttcctcc cacag                                            25

<210> SEQ ID NO 5
<211> LENGTH: 13
<212> TYPE: DNA
<213> ORGANISM: Homo sapiens

<400> SEQUENCE: 5
tttctctcca cag                                                         13

<210> SEQ ID NO 6
<211> LENGTH: 9
<212> TYPE: PRT
<213> ORGANISM: Unknown
<220> FEATURE:
<223> OTHER INFORMATION: Description of Unknown:
      'LAGLIDADG' family peptide motif sequence

<400> SEQUENCE: 6

Leu Ala Gly Leu Ile Asp Ala Asp Gly
1               5
```

METHODS AND COMPOSITIONS FOR ENHANCING FUNCTIONAL MYELIN PRODUCTION

REFERENCE TO RELATED APPLICATIONS

This application is a continuation application of U.S. patent application Ser. No. 16/467,428, filed on Jun. 6, 2019, which is a U.S. national stage application filed under 35 U.S.C. § 371(c) of International Patent Application No. PCT/US2017/064870, filed on Dec. 6, 2017, which claims the benefit of the filing dates of U.S. Provisional Patent Application No. 62/431,787, filed on Dec. 8, 2016, and U.S. Provisional Patent Application No. 62/542,660, filed on Aug. 8, 2017, the entire contents of each of the above-referenced applications are incorporated herein by reference.

SEQUENCE LISTING

The instant application contains a Sequence Listing which has been submitted electronically in ASCII format and is hereby incorporated by reference in its entirety. Said ASCII copy, created on Apr. 23, 2020, is named SEQUENCE_LISTING_129241_00504.txt and is 1,895 bytes in size.

BACKGROUND OF THE INVENTION

Myelin-related disorders impact millions of people, levying a heavy burden of morbidity and mortality on affected individuals and their families. Leukodystrophies are genetic myelin-related disorders that collectively impact 1 in 7,500 newborns in the United States. These disorders lack disease-modifying therapies and inevitably result in severe morbidity and mortality during childhood and adolescence. Several common leukodystrophies have known genetic mutations that result in improper myelination (myelin wrapping) of neuronal axons by oligodendrocytes in the central nervous system (CNS).

Pelizaeus Merzbacher Disease (PMD) is a particularly severe leukodystrophy which causes significant cognitive and motor deficits by four months of age and death in childhood or early adulthood. In more extreme cases patients experience symptoms within two weeks of birth, never learn to walk or speak, and succumb to the disease before the age of 10.

Unfortunately, the pathological processes underlying many of these disorders remain poorly understood and few disease-modifying therapies exist. Therefore, there is pressing need for therapeutics to disorders which impact central nervous system myelin.

SUMMARY OF THE INVENTION

Embodiments described herein relate to compositions and methods for the treatment of myelin-related disorders using gene therapy or genome engineering.

Thus in one aspect, the invention provides a method that generates a cell that enhances functional myelin production, the method comprising genetically modifying the cell such that: (i) an endogenous PLP1 gene is modified to decrease its ability to inhibit myelin production; (ii) an endogenous PLP1 genetic regulatory element is modified to decrease its ability to promote PLP1 expression; (iii) an endogenous PLP1 genetic regulatory element is modified to increase its ability to inhibit PLP1 expression; or (iv) an endogenous PLP1 gene product or a PLP1 regulatory element gene product that promotes PLP1 expression is modified to decrease the PLP1 expression level, wherein the cell produces functional myelin, or is a progenitor that produces or differentiates into the cell that produces functional myelin.

In some embodiments, the generated cell enhances myelin production by reducing PLP1-related toxicity in the cell. In certain embodiments, the modification of the endogenous PLP1 gene or PLP1 genetic regulatory element alleviates PLP1 related cell stress in the cell.

In some embodiments, the modification of the endogenous PLP1 gene can include introduction of mutations that reduce the expression of the endogenous PLP1 gene or result in degradation (e.g., through nonsense-mediated decay) of the PLP1 transcript.

In certain embodiments, the endogenous PLP1 gene or the endogenous PLP1 genetic regulatory element comprises a point mutation, and wherein said modification of the endogenous PLP1 gene or the endogenous PLP1 genetic regulatory element comprises correcting the point mutation to wild-type sequence.

In certain embodiments, the endogenous PLP1 genetic regulatory element is a PLP1 enhancer or promoter.

In some embodiments, the genetic modification of the endogenous PLP1 genetic regulatory element can include introduction of small insertions or deletions (indels) to alter the activity of the PLP1 genetic regulatory element, or larger exonic deletions of PLP1.

In certain embodiments, the genetic modification can include large deletions near the start codon in exon 1 or anywhere in the first three exons of PLP1. In exemplary embodiments, the genetic modification can include large deletions at the 5' end of exon 3 of PLP1.

In other embodiments, the modification of the endogenous PLP1 genetic regulatory elements can include introduction of indels or larger deletions to alter activity of PLP1 genetic regulatory elements, such as a PLP1 enhancer or promoter. In some aspects, the endogenous PLP1 genetic regulatory element is modified to decrease its ability to promote PLP1 transcription. For example, the modification can include disruption of a PLP1 enhancer or promoter.

In certain embodiments, the endogenous PLP1 gene is a deleterious disease-causing mutant PLP1 gene.

In some embodiments, the modification of the endogenous PLP1 gene or PLP1 genetic regulatory element can be made using a nuclease. The nuclease can include a zinc finger nuclease (ZFN), a TALE-effector (TALEN), a CRISPR/Cas system, or an NgAgo system.

In certain embodiments, the nuclease can include a class 2 CRISPR/Cas system. For example, the class 2 CRISPR/Cas system can include a type II Cas9-based CRISPR system or a type V Cpf1-based CRISPR system.

In certain embodiments, the PLP1 gene is modified at exon 1 or exon 3 with a CRISPR/Cas system nuclease. In certain embodiments, the PLP1 gene is modified with a CRISPR/Cas system nuclease at the 5' end of exon 3. In certain embodiments, the PLP1 gene is modified with a CRISPR/Cas system nuclease by disruption of the start codon in exon 1.

In some embodiments, the modification of the PLP1 gene product or PLP1 regulatory element gene product includes delivering to the cell a gene silencing agent. In some embodiments, the gene silencing agent can include an RNAi construct (such as an siRNA, shRNA or miRNA, or a construct that can be transcribed to produce the same).

In some embodiments, the gene silencing agent can include an antisense oligonucleotide (ASO).

In certain embodiments, the cell that is genetically modified exhibit enhanced myelin production (e.g., due to reduced PLP1-related toxicity in the cell).

In certain embodiments, the method comprises contacting the cell with a delivery vehicle comprising the nuclease or the gene silencing agent.

In certain embodiments, the delivery vehicle is an AAV vector, an adenoviral vector, or a lentivirus vector.

In certain embodiments, the method comprises: (a) contacting the cell with a first AAV vector comprising a nucleic acid encoding a functional Type II CRISPR-Cas9 (such as a Cas9 or a Cas9 ortholog cDNA), and a second AAV vector comprising a guide RNA (sgRNA) sequence specific for a target site in the endogenous PLP1 gene or the endogenous PLP1 genetic regulatory element, and optionally a third AAV vector comprising a donor nucleic acid sequence for correction or replacement of a defective or mutant portion of the endogenous PLP1 gene or the endogenous PLP1 genetic regulatory element; or, (b) contacting the cell with a first AAV vector comprising a nucleic acid encoding a functional Type II CRISPR-Cas9 (such as a Cas9 or a Cas9 ortholog cDNA), and a guide RNA (sgRNA) sequence encoded in cis and is specific for a target site in the endogenous PLP1 gene or the endogenous PLP1 genetic regulatory element, and optionally a third AAV vector comprising a donor nucleic acid sequence for correction or replacement of a defective or mutant portion of the endogenous PLP1 gene or the endogenous PLP1 genetic regulatory element.

In certain embodiments, the first AAV vector further comprises one or more of the following elements, optionally in 5'→3' orientation: i) a 5' AAV inverted terminal repeat (ITR); ii) a promoter and optional enhancer; iii) a Cas9 cDNA encoding the functional Type II CRISPR-Cas9; iv) a polyadenylation signal; and, v) a 3' AAV inverted terminal repeat (ITR).

In certain embodiments, the promoter and optional enhancer may be a ubiquitous or constitutive promoter and optional ubiquitous or constitutive enhancer; a regulatable, inducible or de-repressible promoter and optional regulatable, inducible or de-repressible enhancer; a tissue specific promoter and optional tissue specific enhancer; a viral promoter and optional viral enhancer; a promoter active in zygote, OPC, NSC, or oligodendrocytes; a viral promoter, optionally a CMV promoter, or a viral enhancer; a mammalian Beta Actin promoter; a Chicken Beta Actin promoter; a mammalian U6 promoter; or a human U6 promoter.

In certain embodiments, the second or the third AAV vector (when present) further comprises one or more of the following elements, optionally in 5'→3' orientation: i) a 5' AAV ITR; ii) a promoter and optional enhancer; iii) the guide RNA sequence; iv) a stuffer or filler nucleic acid sequence; and, v) a 3' AAV ITR.

In certain embodiments, the third AAV vector (when present) further comprises one or more of the following elements, optionally in 5'→3' orientation: i) a 5' AAV ITR; ii) a 5' slice acceptor site; iii) the donor nucleic acid sequence; iv) a polyadenylation signal; and, v) an AAV 3' ITR.

In certain embodiments, the 1st, 2nd, and/or 3rd AAV vector comprises a VP1, VP2, or VP3 capsid selected from any serotype of AAV1, AAV2, AAV3, AAV4, AAV5, AAV6, AAV7, AAV8, AAV9, AAV10, AAV11, or mixtures, variants or derivatives thereof.

In certain embodiments, the 5' AAV ITR is selected from any one of AAV1, AAV2, AAV3, AAV4, AAV5, AAV6, AAV7, AAV8, AAV9, AAV 10, AAV11, or chimeras or fusions thereof, or wherein the 3'AAV ITR is selected from any one of AAV1, AAV2, AAV3, AAV4, AAV5, AAV6, AAV7, AAV8, AAV9, AAV 10, AAV11, or chimeras or fusions thereof.

In certain embodiments, the cell is contacted in vitro, in vivo, or ex vivo.

Another aspect of the invention provides a composition comprising the first and the second AAV vectors (and optionally the 3rd AAV vector) of any of the embodiments described herein.

Another aspect of the invention provides a pharmaceutical composition comprising the composition described herein.

Another aspect of the invention provides a genetically modified cell. The cell can be genetically modified such that: (i) an endogenous PLP1 gene is modified to decrease its ability to inhibit myelin production; (ii) an endogenous PLP1 genetic regulatory element is modified to decrease its ability to promote PLP1 expression; (iii) an endogenous PLP1 genetic regulatory element is modified to increase its ability to inhibit PLP1 expression; or (iv) an endogenous PLP1 gene product or a PLP1 regulatory element gene product that promotes PLP1 expression is modified to decrease the PLP1 expression level, wherein the cell produces functional myelin, or is a progenitor that produces or differentiates into the cell that produces functional myelin.

In certain embodiments, the cell is selected from a neural stem cell (NSC), oligodendrocyte progenitor cell (OPC), neuron cell, and a glial cell such as an oligodendrocyte, astrocyte, ependymal cell, or microglia cell, preferably NSC, OPC, and oligodendrocyte, more preferably NSC or OPC.

Still other aspect of the invention relates to a genetically modified cell descended or differentiated from a cell that is genetically modified such that: (i) an endogenous PLP1 gene is modified to decrease its ability to inhibit myelin production; (ii) an endogenous PLP1 genetic regulatory element is modified to decrease its ability to promote PLP1 expression; (iii) an endogenous PLP1 genetic regulatory element is modified to increase its ability to inhibit PLP1 expression; or (iv) an endogenous PLP1 gene product or a PLP1 regulatory element gene product that promotes PLP1 expression is modified to decrease the PLP1 expression level, wherein the cell produces functional myelin, or is a progenitor that produces or differentiates into the cell that produces functional myelin.

Still other aspect of the invention relates to compositions including a genetically modified cell described above and to methods of treating a myelin related disorder in a subject. The method can include administering to the subject a cell that is genetically modified such that: (i) an endogenous PLP1 gene is modified to decrease its ability to inhibit myelin production; (ii) an endogenous PLP1 genetic regulatory element is modified to decrease its ability to promote PLP1 expression; (iii) an endogenous PLP1 genetic regulatory element is modified to increase its ability to inhibit PLP1 expression; or (iv) an endogenous PLP1 gene product or a PLP1 regulatory element gene product that promotes PLP1 expression is modified to decrease the PLP1 expression level, wherein the cell produces functional myelin in the subject, or is a progenitor that produces or differentiates into the cell that produces functional myelin.

In a related aspect, the invention provides a method of treating a myelin related disorder in a subject, the method comprising genetically modifying a cell of the subject according to the method of the invention described herein, thereby producing functional myelin in the subject, wherein the myelin related disorder preferably is characterized by abnormal PLP1 gene activity and/or expression.

In certain embodiments, the myelin-related disorder is selected from multiple sclerosis (MS), neuromyelitis optica (NMO), transverse myelitis, chronic inflammatory demyelinating polyneuropathy, Guillain-Barre Syndrome, progressive multifocal leukoencephalopathy (PML), encephalomyelitis (EPL), central pontine myelolysis (CPM), adrenoleukodystrophy, Alexander's disease, Pelizaeus Merzbacher disease (PMD), Wallerian Degeneration, optic neuritis, amylotrophic lateral sclerosis (ALS), Huntington's disease, Alzheimer's disease, Parkinson's disease, spinal cord injury, traumatic brain injury, post radiation injury, neurologic complications of chemotherapy, stroke, acute ischemic optic neuropathy, vitamin E deficiency, isolated vitamin E deficiency syndrome, Bassen-Kornzweig syndrome, Marchiafava-Bignami syndrome, trigeminal neuralgia, Marie-Charcot-Tooth disease, Bell's palsy, and leukodystrophy.

In other embodiments, the myelin-related disorder can be a leukodystrophy, such as one selected from the group consisting of 18q Syndrome with deficiency of myelin basic protein, Acute Disseminated Encephalomyeolitis (ADEM), Acute Disseminated Leukoencephalitis, Acute Hemorrhagic Leukoencephalopathy, Adrenoleukodystrophy (ALD), Adrenomyeloneuropathy (AMN), Adult Onset Autosomal Dominant Leukodystrophy (ADLD), Adult Polyglucosan Body Disease, Aicardi-Goutieres Syndrome, Alexander Disease, Autosomal Dominant Diffuse Leukoencephalopathy with Neuroaxonal Spheroids (HDLS), Autosomal Dominant Late-Onset Leukoencephalopathy, Canavan Disease, Childhood Ataxia with diffuse CNS Hypomyelination (CACH or Vanishing White Matter Disease), Cerebral Autosomal Dominant Arteriopathy with Subcortical Infarcts and Leukoencephalopathy (CADASIL), Cerebroretinal Micro-angiography with calcifications and cysts, Cerebrotendinous Xanthomatosis (CTX), Childhood Ataxia with Central Nervous System Hypomyelination (CACH), Craniometaphysical Dysplasia with Leukoencephalopathy, Cystic Leukoencephalopathy (RNASET2 related), Elongation of Very Long-Chain Fatty Acids-4 (ELOVL4; Pseudo-Sjogren-Larsson), Extensive Cerebral White Matter abnormality without clinical symptoms, Familial Adult-Onset Leukodystrophy manifesting as cerebellar ataxia and dementia, Familial Leukodystrophy with adult onset dementia and abnormal glycolipid storage, Fatty Acid 2-hydroxylase Deficiency, Fucosidosis, Fukuyama Congenital Muscular Dystrophy, Galactosialidosis, Globoid Cell Leukodystrophy (Krabbe Disease), GM1 Gangliosidosis, GM2 Gangliosidosis (Tay-Sachs Disease), Hereditary Adult Onset Leukodystrophy simulating chronic progressive multiple sclerosis, Herditary Diffuse Leukoencephalopathy with Axonal Spheroids (HDLS), Hypomyelination with Atrophy of the Basal Ganglia and Cerebellum (H-ABC), Hypomyelination, Hypogonadotropic, Hypogonadism and Hypodontia (4H Syndrome), Lipomembranous Osteodysplasia with Leukodystrophy (Nasu Disease), Metachromatic Leukodystrophy (MLD), Megalencephalic Leukodystrophy with subcortical Cysts (MLC), Neuroaxonal Leukoencephalopathy with axonal spheroids (Hereditary diffuse leukoencephalopathy with spheroids—HDLS), Neonatal Adrenoleukodystrophy (NALD), Oculodetatoldigital Dysplasia with cerebral white matter abnormalities, Orthochromatic Leukodystrophy with pigmented glia, Ovarioleukodystrophy Syndrome, Pelizaeus Merzbacher Disease (X-linked spastic paraplegia), Refsum Disease, Sjogren-Larsson Syndrome, Sudanophilic Leukodystrophy, Van der Knaap Syndrome (Vacuolating Leukodystrophy with Subcortical Cysts or MLC), Vanishing White Matter Disease (VWM) or Childhood ataxia with diffuse central nervous system hypomyelination (CACH), X-linked Adrenoleukodystrophy (X-ALD), Zellweger Spectrum: Zellweger Syndrome, Neonatal Adrenoleukodystrophy, and Infantile Refsum Disease.

In certain embodiments, the myelin-related disorder includes Pelizaeus Merzbacher disease (PMD).

In certain embodiments, the method restores the lifespan of the subject to at least 30%, 40%, 50%, 60%, 70%, 80%, 90%, or about 100% of a control subject without the myelin related disorder.

In certain embodiments, the method alleviates at least one symptom(s) of the subject associated with said myelin related disorder.

In certain embodiments, the method restores a function of the subject to at least 30%, 40%, 50%, 60%, 70%, 80%, 90%, or about 100% of a control subject without the myelin related disorder, preferably, the function is motor coordination, locomotion, or axon conduction velocity.

In certain embodiments, the cell is selected from the group consisting of a genetically modified NSC, OPC, neuron cell, oligodendrocyte, astrocyte, ependymal cell, and microglia cell, preferably NSC, OPC, or oligodendrocyte.

In certain embodiments, the endogenous PLP1 gene or genetic regulatory element thereof, or a portion thereof (such as a portion no more than 4.8, 4.5, 4.0, 3.5, 3.0, 2.5, 2.0, 1.5, or 1.0 kb), is inactivated, disrupted, corrected or replaced.

In certain embodiments, the subject is a mammal, such as a human (e.g., a human younger than 20 years old, 15 years old, 10 years old, 5 years old, 3 years old, 2 years old, 1 year old, 6 months old, 3 months old, 1 month old, 2 weeks old, 1 week old, 3 days old, or 1 day old).

All of the features disclosed herein may be combined in any combination. Each feature disclosed in the specification may be replaced by an alternative feature serving a same, equivalent, or similar purpose, unless expressly stated otherwise.

BRIEF DESCRIPTION OF THE DRAWINGS

FIG. 4 shows the relative locations of the sgRNA targeting sites in exon 3. FIG. 5 shows the general experimental approach to generate the jimpy male zygote for receiving the sgRNAs and the SpCas9 mRNA. Successful CRISPR/Cas9 mediated knockout of the jimpy PLP1 gene leads to the birth of a PLP1 null male CR-impy founder born by a surrogate host female. Two generations of crossing to the parental strain yield progeny mice for further characterization. At postnatal day 21 (P21), when most jimpy mice exhibit severe neurological symptoms or are dead, the CR-impy mice lacked an overt phenotype (data not shown).

FIG. 8 shows a schematic drawing for the rotarod testing for assessing motor coordination of CR-impy mice, where motor coordination is quantitated by a measured time to fall from the rotating bar when the rotating bar is accelerated. The measurements were done at postnatal day 19 (P19), 2 months postnatal, and 6 months postnatal, in wild-type, jimpy, and CR-impy mice at each time point. Statistical significance between the different values is indicated by p values. The results show restoration of motor coordination in CR-impy mice compared to wild-type and jimpy mice.

FIG. 11 shows that there is no discernible difference in optic nerve EM image between the wild-type and CR-impy mice at 6 months postnatal.

DETAILED DESCRIPTION OF THE INVENTION

Definitions

Figure 1:
FIG. 1 is an image of a histological analysis demonstrating full myelination of the central nervous system in PLP1-indel corrected jimpy (or crimpy) PMD model mice that is indistinguishable from wild-type in MBP (myelin basic protein) staining.

For convenience, certain terms employed in the specification, examples, and appended claims are collected here. Unless defined otherwise, all technical and scientific terms used herein have the same meaning as commonly understood by one of ordinary skill in the art to which this application belongs.

The articles "a" and "an" are used herein to refer to one or to more than one (i.e., to at least one) of the grammatical object of the article. By way of example, "an element" means one element or more than one element.

The terms "comprise," "comprising," "include," "including," "have," and "having" are used in the inclusive, open sense, meaning that additional elements may be included. The terms "such as", "e.g.", as used herein are non-limiting and are for illustrative purposes only. "Including" and "including but not limited to" are used interchangeably.

The term "or" as used herein should be understood to mean "and/or", unless the context clearly indicates otherwise.

As used herein, the term "about" or "approximately" refers to a quantity, level, value, number, frequency, percentage, dimension, size, amount, weight or length that varies by as much as 15%, 10%, 9%, 8%, 7%, 6%, 5%, 4%, 3%, 2% or 1% to a reference quantity, level, value, number, frequency, percentage, dimension, size, amount, weight or length. In one embodiment, the term "about" or "approximately" refers a range of quantity, level, value, number, frequency, percentage, dimension, size, amount, weight or length±15%, ±10%, ±9%, ±8%, ±7%, ±6%, ±5%, ±4%, ±3%, ±2%, or ±1% about a reference quantity, level, value, number, frequency, percentage, dimension, size, amount, weight or length.

The phrases "parenteral administration" and "administered parenterally" are art-recognized terms, and include modes of administration other than enteral and topical administration, such as injections, and include, without limitation, intravenous, intramuscular, intrapleural, intravascular, intrapericardial, intraarterial, intrathecal, intracapsular, intraorbital, intracardiac, intradermal, intraperitoneal, transtracheal, subcutaneous, subcuticular, intra-articular, subcapsular, subarachnoid, intraspinal and intrasternal injection and infusion.

The term "treating" is art-recognized and includes inhibiting a disease, disorder or condition in a subject, e.g., impeding its progress; and relieving the disease, disorder or condition, e.g., causing regression of the disease, disorder and/or condition. Treating the disease or condition includes ameliorating at least one symptom of the particular disease or condition, even if the underlying pathophysiology is not affected.

The term "preventing" is art-recognized and includes stopping a disease, disorder or condition from occurring in a subject, which may be predisposed to the disease, disorder and/or condition but has not yet been diagnosed as having it. Preventing a condition related to a disease includes stopping the condition from occurring after the disease has been diagnosed but before the condition has been diagnosed.

The term "pharmaceutical composition" refers to a formulation containing the disclosed compounds in a form suitable for administration to a subject. In a preferred embodiment, the pharmaceutical composition is in bulk or in unit dosage form. The unit dosage form is any of a variety of forms, including, for example, a capsule, an IV bag, a tablet, a single pump on an aerosol inhaler, or a vial. The quantity of active ingredient (e.g., a formulation of the disclosed compound or salts thereof) in a unit dose of composition is an effective amount and is varied according to the particular treatment involved. One skilled in the art will appreciate that it is sometimes necessary to make routine variations to the dosage depending on the age and condition of the patient. The dosage will also depend on the route of administration. A variety of routes are contemplated, including oral, pulmonary, rectal, parenteral, transdermal, subcutaneous, intravenous, intramuscular, intraperitoneal, intranasal, inhalational, and the like. Dosage forms for the topical or transdermal administration of a compound described herein includes powders, sprays, ointments, pastes, creams, lotions, gels, solutions, patches, nebulized compounds, and inhalants. In a preferred embodiment, the active compound is mixed under sterile conditions with a pharmaceutically acceptable carrier, and with any preservatives, buffers, or propellants that are required.

The phrase "pharmaceutically acceptable" is art-recognized. In certain embodiments, the term includes compositions, polymers and other materials and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The phrase "pharmaceutically acceptable carrier" is art-recognized, and includes, for example, pharmaceutically acceptable materials, compositions or vehicles, such as a liquid or solid filler, diluent, excipient, solvent or encapsulating material, involved in carrying or transporting any subject composition from one organ, or portion of the body, to another organ, or portion of the body. Each carrier must be "acceptable" in the sense of being compatible with the other ingredients of a subject composition and not injurious to the patient. In certain embodiments, a pharmaceutically acceptable carrier is non-pyrogenic. Some examples of materials which may serve as pharmaceutically acceptable carriers include: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) talc; (8) excipients, such as cocoa butter and suppository waxes; (9) oils, such as peanut oil, cottonseed oil, sunflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) phosphate buffer solutions; and (21) other non-toxic compatible substances employed in pharmaceutical formulations.

The terms "prophylactic" or "therapeutic" treatment is art-recognized and includes administration to the host of one or more of the subject compositions. If it is administered prior to clinical manifestation of the unwanted condition (e.g., disease or other unwanted state of the host animal such as, but not limited to, myelination disturbances, myelin deficiencies, myelin loss and ineffective myelin repair) then the treatment is prophylactic, i.e., it protects the host against developing the unwanted condition, whereas if it is administered after manifestation of the unwanted condition, the treatment is therapeutic (i.e., it is intended to diminish, ameliorate, or stabilize the existing unwanted condition or side effects thereof).

The terms "therapeutic agent", "drug", "medicament" and "bioactive substance" are art-recognized and include molecules and other agents that are biologically, physiologically, or pharmacologically active substances that act locally or systemically in a patient or subject to treat a disease or condition. The terms include without limitation pharmaceutically acceptable salts thereof and prodrugs. Such agents may be acidic, basic, or salts; they may be neutral molecules, polar molecules, or molecular complexes capable of hydrogen bonding; they may be prodrugs in the form of ethers, esters, amides and the like that are biologically activated when administered into a patient or subject.

The phrase "therapeutically effective amount" or "pharmaceutically effective amount" is an art-recognized term. In certain embodiments, the term refers to an amount of a therapeutic agent that produces some desired effect at a reasonable benefit/risk ratio applicable to any medical treatment. In certain embodiments, the term refers to that amount necessary or sufficient to eliminate, reduce or maintain a target of a particular therapeutic regimen. The effective amount may vary depending on such factors as the disease or condition being treated, the particular targeted constructs being administered, the size of the subject or the severity of the disease or condition. One of ordinary skill in the art may empirically determine the effective amount of a particular compound without necessitating undue experimentation. In certain embodiments, a therapeutically effective amount of an agent (e.g., a composition or genetically modified cells described herein) for in vivo use will likely depend on a number of factors, including: the rate of release of an agent from a polymer matrix, which will depend in part on the chemical and physical characteristics of the polymer; the identity of the agent; the mode and method of administration; and any other materials incorporated in the polymer matrix in addition to the agent.

The terms "nucleic acid", "nucleotide", "polynucleotide," and "oligonucleotide" are used interchangeably and refer to a deoxyribonucleotide or ribonucleotide polymer, in linear or circular conformation, and in either single- or double-stranded form. For the purposes of the present disclosure, these terms are not to be construed as limiting with respect to the length of a polymer. The terms can encompass known analogues of natural nucleotides, as well as nucleotides that are modified in the base, sugar and/or phosphate moieties (e.g., phosphorothioate backbones). In general, an analogue of a particular nucleotide has the same base-pairing specificity; i.e., an analogue of A will base-pair with T.

The terms "polypeptide," "peptide" and "protein" are used interchangeably to refer to a polymer of amino acid residues. The term also applies to amino acid polymers in which one or more amino acids are chemical analogues or modified derivatives of a corresponding naturally-occurring amino acids.

A "functional domain" is a domain of a polypeptide comprising a specific activity. Non-limiting examples of activities that a functional domain may possess are nuclease activity, transcriptional regulatory activity, viral capsid recognition activity and the like.

"Binding" refers to a sequence-specific, non-covalent interaction between macromolecules (e.g., between a protein and a nucleic acid). Not all components of a binding interaction need be sequence-specific (e.g., contacts with phosphate residues in a DNA backbone), as long as the interaction as a whole is sequence-specific. Such interactions are generally characterized by a dissociation constant $(K_d)$ of $10^{-6} M^{-1}$ or lower. "Affinity" refers to the strength of binding: increased binding affinity being correlated with a lower $K_d$.

A "binding protein" is a protein that is able to bind to another molecule. A binding protein can bind to, for example, a DNA molecule (a DNA-binding protein), an RNA molecule (an RNA-binding protein) and/or a protein molecule (a protein-binding protein). In the case of a protein-binding protein, it can bind to itself (to form homodimers, homotrimers, etc.) and/or it can bind to one or more molecules of a different protein or proteins. A binding protein can have more than one type of binding activity. For example, zinc finger proteins have DNA-binding, RNA-binding and protein-binding activity.

A "zinc finger DNA binding protein" (or binding domain) is a protein, or a domain within a larger protein, that binds DNA in a sequence-specific manner through one or more zinc fingers, which are regions of amino acid sequence within the binding domain whose structure is stabilized through coordination of a zinc ion. The term zinc finger DNA binding protein is often abbreviated as zinc finger protein or ZFP.

A "TALE DNA binding domain" or "TALE" is a polypeptide comprising one or more TALE repeat domains/units. The repeat domains are involved in binding of the TALE to its cognate target DNA sequence. A single "repeat unit" (also referred to as a "repeat") is typically 33-35 amino acids in length and exhibits at least some sequence homology with other TALE repeat sequences within a naturally occurring TALE protein.

Zinc finger and TALE binding domains can be "engineered" to bind to a predetermined nucleotide sequence, for example via engineering (altering one or more amino acids) of the recognition helix region of a naturally occurring zinc finger or TALE protein. Therefore, engineered DNA binding proteins (zinc fingers or TALEs) are proteins that are non-naturally occurring. Non-limiting examples of methods for engineering DNA-binding proteins are design and selection. A designed DNA binding protein is a protein not occurring in nature whose design/composition results principally from rational criteria. Rational criteria for design include application of substitution rules and computerized algorithms for processing information in a database storing information of existing ZFP and/or TALE designs and binding data. See, for example, U.S. Pat. Nos. 6,140,081; 6,453,242; 6,534,261 and 8,585,526; see also WO 98/53058; WO 98/53059; WO 98/53060; WO 02/016536 and WO 03/016496.

A "selected" zinc finger protein or TALE is a protein not found in nature whose production results primarily from an empirical process such as phage display, interaction trap or hybrid selection. See e.g., U.S. Pat. Nos. 5,789,538; 5,925, 523; 6,007,988; 6,013,453; 6,200,759; 8,586,526; WO 95/19431; WO 96/06166; WO 98/53057; WO 98/54311; WO 00/27878; WO 01/60970 WO 01/88197, WO 02/099084.

In general, "CRISPRs" (Clustered Regularly Interspaced Short Palindromic Repeats), also known as SPIDRs (SPacer Interspersed Direct Repeats), refer a family of DNA loci that are usually specific to a particular bacterial species. The CRISPR locus comprises a distinct class of interspersed short sequence repeats (SSRs) that were recognized in E. coli (Ishino et al. (1987) J. Bacteriol., 169:5429-5433; and Nakata et al., J. Bacteriol. (1989) 171:3553-3556), and associated genes. Similar interspersed SSRs have been identified in Haloferax mediterranei, Streptococcus pyogenes, Anabaena, and Mycobacterium tuberculosis (See, Groenen et al. (1993) Mol. Microbiol., 10:1057-1065; Hoe et al. (1999) Emerg. Infect. Dis., 5:254-263; Masepohl et al. (1996) Biochim. Biophys. Acta 1307:26-30; and Mojica et al. (1995) Mol. Microbiol., 17:85-93). The CRISPR loci typically differ from other SSRs by the structure of the repeats, which have been termed short regularly spaced repeats (SRSRs) (Janssen et al. (2002) OMICS J. Integ. Biol., 6:23-33; and Mojica et al. (2000) Mol. Microbiol., 36:244-246). In general, the repeats are short elements that occur in clusters that are regularly spaced by unique intervening sequences with a substantially constant length (Mojica et al. (2000), supra). Although the repeat sequences are highly conserved between strains, the number of interspersed repeats and the sequences of the spacer regions typically differ from strain to strain (van Embden et al., J. Bacteriol. (2002) 182:2393-2401). CRISPR loci have been identified in more than 40 prokaryotes including, but not limited to Aeropyrum, Pyrobaculum, Sulfolobus, Archaeoglobus, Halocarcula, Methanobacteriumn, Methanococcus, Methanosarcina, Methanopyrus, Pyrococcus, Picrophilus, Thernioplasnia, Corynebacterium, Mycobacterium, Streptomyces, Aquifrx, Porphvromonas, Chlorobium, Thermus, Bacillus, Listeria, Staphylococcus, Clostridium, Thermoanaerobacter, Mycoplasma, Fusobacterium, Azarcus, Chromobacterium, Neisseria, Nitrosomonas, Desulfovibrio, Geobacter, Myrococcus, Campylobacter, Wolinella, Acinetobacter, Erwinia, Escherichia, Legionella, Methylococcus, Pasteurella, Photobacterium, Salmonella, Xanthomonas, Yersinia, Treponema, and Thermotoga.

"CRISPR system" refers collectively to transcripts and other elements involved in the expression of or directing the activity of CRISPR-associated ("Cas") genes, including sequences encoding a Cas gene, a tracr (trans-activating CRISPR) sequence (e.g., tracrRNA or an active partial tracrRNA), a tracr-mate sequence (encompassing a "direct repeat" and a tracrRNA-processed partial direct repeat in the context of an endogenous CRISPR system), a guide sequence (also referred to as a "spacer" in the context of an endogenous CRISPR system), or other sequences and transcripts from a CRISPR locus. In some embodiments, one or more elements of a CRISPR system is derived from a class 1 type I or type III CRISPR system. In some embodiments, one or more elements of a CRISPR system is derived from a class 2 type II, or type V CRISPR system. In some embodiments, one or more elements of a CRISPR system is derived from a particular organism comprising an endogenous CRISPR system, such as Streptococcus pyogenes. In general, a CRISPR system is characterized by elements that promote the formation of a CRISPR complex at the site of a target sequence (also referred to as a protospacer in the context of an endogenous CRISPR system). In the context of formation of a CRISPR complex, "target sequence" refers to a sequence to which a guide sequence is designed to have complementarity, where hybridization between a target sequence and a guide sequence promotes the formation of a CRISPR complex. Full complementarity is not necessarily required, provided there is sufficient complementarity to cause hybridization and promote formation of a CRISPR complex. A target sequence may comprise any polynucleotide, such as DNA or RNA polynucleotides. In some embodiments, a target sequence is located in the nucleus or cytoplasm of a cell. A sequence or template that may be used for recombination into the targeted locus comprising the target sequences is referred to as an "editing template" or "editing polynucleotide" or "editing sequence." In aspects of the invention, an exogenous template polynucleotide may be referred to as an editing template. In an aspect of the invention the recombination is homologous recombination.

"NgAgo" is a prokaryotic Argonaute protein thought to be involved in gene silencing. NgAgo is derived from the archaebacteria Natronobacterium gregoryi (See, e.g., Gao et al. (2016) Nature Biotechnology 34, 768-773). A "NgAgo system" is all the components required including e.g., single stranded guide DNAs for cleavage by a NgAgo enzyme.

"Recombination" refers to a process of exchange of genetic information between two polynucleotides, including but not limited to, donor capture by non-homologous end joining (NHEJ) and homologous recombination. For the purposes of this disclosure, "homologous recombination (HR)" refers to the specialized form of such exchange that takes place, for example, during repair of double-strand breaks in cells via homology-directed repair mechanisms. This process requires nucleotide sequence homology, uses a "donor" molecule to template repair of a "target" molecule (i.e., the one that experienced the double-strand break), and is variously known as "non-crossover gene conversion" or "short tract gene conversion," because it leads to the transfer of genetic information from the donor to the target. Without wishing to be bound by any particular theory, such transfer can involve mismatch correction of heteroduplex DNA that forms between the broken target and the donor, and/or "synthesis-dependent strand annealing," in which the donor is used to resynthesize genetic information that will become part of the target, and/or related processes. Such specialized HR often results in an alteration of the sequence of the target molecule such that part or all of the sequence of the donor polynucleotide is incorporated into the target polynucleotide.

In the methods of the disclosure, one or more targeted nucleases as described herein cleave (e.g., create one or more single-stranded nicks and/or one or more double-stranded breaks [DSBs]) in the target sequence (e.g., cellular chromatin) at a predetermined site. The DSB may result in deletions and/or insertions by homology-directed repair (HDR) or by non-homology-directed repair mechanisms (e.g., NHEJ). Deletions may include any number of base pairs. Similarly, insertions may include any number of base pairs including, for example, integration of a "donor" polynucleotide, optionally having homology to the nucleotide sequence in the region of the break.

In certain embodiments, the methods of the invention generates DSBs in a target gene (such as the PLP1 gene or a regulatory element thereof) using any of the suitable nucleases, such as the CRISPR/Cas system nuclease, and the resulting repair (such as NHEJ) creates a small insertion or deletion (e.g., indel) that disrupts the function of the PLP1 gene or regulatory element thereof, resulting in reduced or eliminated PLP1 function. In this embodiment, no donor sequence is required for the method of the invention.

In other embodiments, a donor sequence may be included in the method to repair or replace a defective PLP1 gene or a regulatory element thereof. The donor sequence may be physically integrated or, alternatively, the donor polynucleotide is used as a template for repair of the break via homologous recombination, resulting in the introduction of all or part of the nucleotide sequence as in the donor into the cellular chromatin. Thus, a first sequence in cellular chromatin can be altered and, in certain embodiments, can be converted into a sequence present in a donor polynucleotide. Thus, the use of the terms "replace" or "replacement" can be understood to represent replacement of one nucleotide sequence by another, (i.e., replacement of a sequence in the informational sense), and does not necessarily require physical or chemical replacement of one polynucleotide by another.

In any of the methods described herein, additional pairs of zinc-finger proteins, TALENs, CRISPR/Cas or NgAgo systems can be used for additional (e.g., two or more) double-stranded cleavage of additional target sites within the cell (e.g., within the same target gene such as PLP1 but at different targeting sites).

Any of the methods described herein can be used for insertion of a donor of any size and/or partial or complete inactivation of one or more target sequences in a cell by targeted integration of donor sequence that disrupts expression of the gene(s) of interest. Cell lines with partially or completely inactivated genes are also provided.

In any of the methods described herein, the exogenous nucleotide sequence (the "donor sequence" or "transgene") can contain sequences that are homologous, but not identical, to genomic sequences in the region of interest, thereby stimulating homologous recombination to insert a non-identical sequence in the region of interest. Thus, in certain embodiments, portions of the donor sequence that are homologous to sequences in the region of interest exhibit between about 80 to 99% (or any integer therebetween) sequence identity to the genomic sequence that is replaced. In other embodiments, the homology between the donor and genomic sequence is higher than 99%, for example if only 1 nucleotide differs as between donor and genomic sequences of over 100 contiguous base pairs. In certain cases, a non-homologous portion of the donor sequence can contain sequences not present in the region of interest, such that new sequences are introduced into the region of interest. In these instances, the non-homologous sequence is generally flanked by sequences of 50-1,000 base pairs (or any integral value therebetween) or any number of base pairs greater than 1,000, that are homologous or identical to sequences in the region of interest. In other embodiments, the donor sequence is non-homologous to the first sequence, and is inserted into the genome by non-homologous recombination mechanisms.

"Genetically modified" refers to a modification made to a nucleic acid such that the sequence of the nucleic acid is altered in comparison to the nucleic acid prior to being modified. Genetically modifying a cell refers to modifying cellular nucleic acid within a cell, including genetic modifications to endogenous and/or exogenous nucleic acids within the cell, such as genomic DNA and transcribed mRNA. Genetic modifications can comprise cleavages, deletions, and insertions in endogenous and/or exogenous nucleic acids within the cell, integrations of exogenous DNA, gene correction and/or gene mutation.

"Cleavage" refers to the breakage of the covalent backbone of a nucleic acid (e.g., DNA or RNA such as mRNA) molecule. Cleavage can be initiated by a variety of methods including, but not limited to, enzymatic or chemical hydrolysis of a phosphodiester bond. Both single-stranded cleavage and double-stranded cleavage are possible, and double-stranded cleavage can occur as a result of two distinct single-stranded cleavage events. DNA cleavage can result in the production of either blunt ends or staggered ends. In certain embodiments, fusion polypeptides are used for targeted double-stranded DNA cleavage.

A "cleavage half-domain" is a polypeptide sequence which, in conjunction with a second polypeptide (either identical or different) forms a complex having cleavage activity (preferably double-strand cleavage activity). The terms "first and second cleavage half-domains;" "+ and −cleavage half-domains" and "right and left cleavage half-domains" are used interchangeably to refer to pairs of cleavage half-domains that dimerize.

An "engineered cleavage half-domain" is a cleavage half-domain that has been modified so as to form obligate heterodimers with another cleavage half-domain (e.g., another engineered cleavage half-domain). See, also, U.S. Patent Publication Nos. 2005/0064474, 20070218528, 20080131962 and 20110201055, incorporated herein by reference in their entireties.

The term "sequence" refers to a nucleotide sequence of any length, which can be DNA or RNA; can be linear, circular or branched and can be either single-stranded or double stranded.

The term "donor sequence" refers to a nucleotide sequence that is inserted into a genome. A donor sequence can be of any length, for example between 2 and 100,000,000 nucleotides in length (or any integer value therebetween or thereabove), preferably between about 100 and 100,000 nucleotides in length (or any integer therebetween), more preferably between about 2000 and 20,000 nucleotides in length (or any value therebetween) and even more preferable, between about 5 and 15 kb (or any value therebetween).

"Chromatin" is the nucleoprotein structure comprising the cellular genome. Cellular chromatin comprises nucleic acid, primarily DNA, and protein, including histones and non-histone chromosomal proteins. The majority of eukaryotic cellular chromatin exists in the form of nucleosomes, wherein a nucleosome core comprises approximately 150 base pairs of DNA associated with an octamer comprising two each of histones H2A, H2B, H3 and H4; and linker DNA (of variable length depending on the organism) extends between nucleosome cores. A molecule of histone H1 is generally associated with the linker DNA. For the purposes of the present disclosure, the term "chromatin" is meant to encompass all types of cellular nucleoprotein, both prokaryotic and eukaryotic. Cellular chromatin includes both chromosomal and episomal chromatin (e.g., mitochondrial DNA).

A "chromosome," is a chromatin complex comprising all or a portion of the genome of a cell. The genome of a cell is often characterized by its karyotype, which is the collection of all the chromosomes that comprise the genome of the cell. The genome of a cell can comprise one or more chromosomes.

An "episome" is a replicating nucleic acid, nucleoprotein complex or other structure comprising a nucleic acid that is not part of the chromosomal karyotype of a cell. Examples of episomes include plasmids and certain viral genomes/vectors (such as AAV vectors and encoded sequences).

An "accessible region" is a site in cellular chromatin in which a target site present in the nucleic acid can be bound by an exogenous molecule which recognizes the target site. Without wishing to be bound by any particular theory, it is believed that an accessible region is one that is not packaged into a nucleosomal structure. The distinct structure of an accessible region can often be detected by its sensitivity to chemical and enzymatic probes, for example, nucleases.

A "target site" or "target sequence" is a nucleic acid sequence that defines a portion of a nucleic acid to which a binding molecule will bind, provided sufficient conditions for binding exist.

An "exogenous" molecule is a molecule that is not normally present in a cell, but can be introduced into a cell by one or more genetic, biochemical or other methods. "Normal presence in the cell" is determined with respect to the particular developmental stage and environmental conditions of the cell. Thus, for example, a molecule that is present only during embryonic development of muscle is an exogenous molecule with respect to an adult muscle cell. Similarly, a molecule induced by heat shock is an exogenous molecule with respect to a non-heat-shocked cell. An exogenous molecule can comprise, for example, a functioning version of a malfunctioning endogenous molecule or a malfunctioning version of a normally-functioning endogenous molecule.

An exogenous molecule can be, among other things, a small molecule, such as is generated by a combinatorial chemistry process, or a macromolecule such as a protein, nucleic acid, carbohydrate, lipid, glycoprotein, lipoprotein, polysaccharide, any modified derivative of the above molecules, or any complex comprising one or more of the above molecules. Nucleic acids include DNA and RNA, can be single- or double-stranded; can be linear, branched or circular; and can be of any length. Nucleic acids include those capable of forming duplexes, as well as triplex-forming nucleic acids. See, for example, U.S. Pat. Nos. 5,176,996 and 5,422,251. Proteins include, but are not limited to, DNA-binding proteins, transcription factors, chromatin remodeling factors, methylated DNA binding proteins, polymerases, methylases, demethylases, acetylases, deacetylases, kinases, phosphatases, integrases, recombinases, ligases, topoisomerases, gyrases and helicases.

An exogenous molecule can be the same type of molecule as an endogenous molecule, e.g., an exogenous protein or nucleic acid. For example, an exogenous nucleic acid can comprise an infecting viral genome, a plasmid or episome introduced into a cell, or a chromosome that is not normally present in the cell. Methods for the introduction of exogenous molecules into cells are known to those of skill in the art and include, but are not limited to, lipid-mediated transfer (i.e., liposomes, including neutral and cationic lipids), electroporation, direct injection, cell fusion, particle bombardment, calcium phosphate co-precipitation, DEAE-dextran-mediated transfer and viral vector-mediated transfer. An exogenous molecule can also be the same type of molecule as an endogenous molecule but derived from a different species than the cell is derived from. For example, a human nucleic acid sequence may be introduced into a cell line originally derived from a mouse or hamster. Methods for the introduction of exogenous molecules into plant cells are known to those of skill in the art and include, but are not limited to, protoplast transformation, silicon carbide (e.g., WHISKERS™), *Agrobacterium*-mediated transformation, lipid-mediated transfer (i.e., liposomes, including neutral and cationic lipids), electroporation, direct injection, cell fusion, particle bombardment (e.g., using a "gene gun"), calcium phosphate co-precipitation, DEAE-dextran-mediated transfer and viral vector-mediated transfer.

By contrast, an "endogenous" molecule is one that is normally present in a particular cell at a particular developmental stage under particular environmental conditions. For example, an endogenous nucleic acid can comprise a chromosome, the genome of a mitochondrion, chloroplast or other organelle, or a naturally-occurring episomal nucleic acid. Additional endogenous molecules can include proteins, for example, transcription factors and enzymes.

As used herein, the term "product of an exogenous nucleic acid" includes both polynucleotide and polypeptide products, for example, transcription products (polynucleotides such as RNA) and translation products (polypeptides).

A "fusion" molecule is a molecule in which two or more subunit molecules are linked, preferably covalently. The subunit molecules can be the same chemical type of molecule, or can be different chemical types of molecules. Examples of the first type of fusion molecule include, but are not limited to, fusion proteins (for example, a fusion between a ZFP or TALE DNA-binding domain and one or more activation domains) and fusion nucleic acids (for example, a nucleic acid encoding the fusion protein described supra). Examples of the second type of fusion molecule include, but are not limited to, a fusion between a triplex-forming nucleic acid and a polypeptide, and a fusion between a minor groove binder and a nucleic acid.

Expression of a fusion protein in a cell can result from delivery of the fusion protein to the cell or by delivery of a polynucleotide encoding the fusion protein to a cell, wherein the polynucleotide is transcribed, and the transcript is translated, to generate the fusion protein. Trans-splicing, polypeptide cleavage and polypeptide ligation can also be involved in expression of a protein in a cell. Methods for polynucleotide and polypeptide delivery to cells are presented elsewhere in this disclosure.

A "gene," for the purposes of the present disclosure, includes a DNA region encoding a gene product (see infra), as well as all DNA regions which regulate the production of the gene product (genetic regulatory elements), whether or not such genetic regulatory element sequences are adjacent to coding and/or transcribed sequences. Accordingly, a gene includes, but is not necessarily limited to, promoter sequences, terminators, translational regulatory sequences such as ribosome binding sites and internal ribosome entry sites, enhancers, silencers, insulators, boundary elements, replication origins, matrix attachment sites and locus control regions.

"Gene expression" refers to the conversion of the information, contained in a gene, into a gene product. A gene product can be the direct transcriptional product of a gene (e.g., mRNA, tRNA, rRNA, antisense RNA, ribozyme, structural RNA or any other type of RNA) or a protein produced by translation of an mRNA. Gene products also include RNAs which are modified, by processes such as capping, polyadenylation, methylation, and editing, and proteins modified by, for example, methylation, acetylation, phosphorylation, ubiquitination, ADP-ribosylation, myristilation, and glycosylation.

"Modulation" of gene expression refers to a change in the activity of a gene. Modulation of expression can include, but is not limited to, gene activation and gene repression, as well as activity and/or stability of gene expression products such as proteins and mRNAs (e.g., modulation of expression at transcriptional, translational, and/or post-translational level). Genome editing (e.g., cleavage, alteration, inactivation, random mutation) can be used to modulate expression, so is RNAi or antisense oligo (ASO)-mediated mRNA cleavage and/or translational blockage. Gene inactivation refers to any reduction in gene expression as compared to a cell that does not include a ZFP, TALE, NgAgo or CRISPR/Cas system as described herein. Thus, gene inactivation may be partial or complete.

A "region of interest" is any region of cellular chromatin, such as, for example, a gene or a non-coding sequence within or adjacent to a gene, in which it is desirable to bind an exogenous molecule. Binding can be for the purposes of targeted DNA cleavage and/or targeted recombination. A region of interest can be present in a chromosome, an episome, an organellar genome (e.g., mitochondrial, chloroplast), or an infecting viral genome, for example. A region of interest can be within the coding region of a gene, within transcribed non-coding regions such as, for example, leader sequences, trailer sequences or introns, or within non-transcribed regions, either upstream or downstream of the coding region. A region of interest can be as small as a single nucleotide pair or up to 2,000 nucleotide pairs in length, or any integral value of nucleotide pairs.

"Eukaryotic" cells include, but are not limited to, fungal cells (such as yeast), plant cells, animal cells, mammalian cells and human cells (e.g., oligodendrocytes), including stem cells (pluripotent and multipotent).

The terms "operative linkage" and "operatively linked" (or "operably linked") are used interchangeably with reference to a juxtaposition of two or more components (such as sequence elements), in which the components are arranged such that both components function normally and allow the possibility that at least one of the components can mediate a function that is exerted upon at least one of the other components. By way of illustration, a transcriptional regulatory element sequence, such as a promoter, is operatively linked to a coding sequence if the transcriptional regulatory element sequence controls the level of transcription of the coding sequence in response to the presence or absence of one or more transcriptional regulatory factors. A transcriptional regulatory element sequence is generally operatively linked in cis with a coding sequence, but need not be directly adjacent to it. For example, an enhancer is a transcriptional regulatory element sequence that is operatively linked to a coding sequence, even though they are not contiguous.

With respect to fusion polypeptides, the term "operatively linked" can refer to the fact that each of the components performs the same function in linkage to the other component as it would if it were not so linked. For example, with respect to a fusion polypeptide in which a ZFP, TALE, NgAgo or Cas DNA-binding domain is fused to an activation domain, the ZFP, TALE, NgAgo or Cas DNA-binding domain and the activation domain are in operative linkage if, in the fusion polypeptide, the ZFP, TALE, NgAgo or Cas DNA-binding domain portion is able to bind its target site and/or its binding site, while the activation domain is able to upregulate gene expression. When a fusion polypeptide in which a ZFP, TALE, NgAgo or Cas DNA-binding domain is fused to a cleavage domain, the ZFP, TALE, NgAgo or Cas DNA-binding domain and the cleavage domain are in operative linkage if, in the fusion polypeptide, the ZFP, TALE, NgAgo or Cas DNA-binding domain portion is able to bind its target site and/or its binding site, while the cleavage domain is able to cleave DNA in the vicinity of the target site.

A "functional fragment" of a protein, polypeptide or nucleic acid is a protein, polypeptide or nucleic acid whose sequence is not identical to the full-length protein, polypeptide or nucleic acid, yet retains the same function as the full-length protein, polypeptide or nucleic acid. A functional fragment can possess more, fewer, or the same number of residues as the corresponding native molecule, and/or can contain one or more amino acid or nucleotide substitutions. Methods for determining the function of a nucleic acid (e.g., coding function, ability to hybridize to another nucleic acid) are well-known in the art. Similarly, methods for determining protein function are well-known. For example, the DNA-binding function of a polypeptide can be determined, for example, by filter-binding, electrophoretic mobility-shift, or immunoprecipitation assays. DNA cleavage can be assayed by gel electrophoresis. See Ausubel et al., supra. The ability of a protein to interact with another protein can be determined, for example, by co-immunoprecipitation, two-hybrid assays or complementation, both genetic and biochemical. See, for example, Fields et al. (1989) *Nature* 340:245-246; U.S. Pat. No. 5,585,245 and PCT WO 98/44350.

A "vector" is capable of transferring gene sequences to target cells. Typically, "vector construct," "expression vector," and "gene transfer vector," mean any nucleic acid construct capable of directing the expression of a gene of interest and which can transfer gene sequences to target cells. Thus, the term includes cloning, and expression vehicles, as well as integrating vectors.

The terms "subject" and "patient" are used interchangeably and refer to mammals such as human patients and non-human primates, as well as experimental animals such as rabbits, dogs, cats, rats, mice, and other animals. Accordingly, the term "subject" or "patient" as used herein means any mammalian patient or subject to which the nucleases, donors and/or genetically modified cells of the invention can be administered. Subjects of the present invention include those with a myelin-related disorder.

"Stemness" refers to the relative ability of any cell to act in a stem cell-like manner, i.e., the degree of toti-, pluri-, or oligopotentcy and expanded or indefinite self-renewal that any particular stem cell may have.

By "cells that that enhances functional myelin production" is meant a cell that exhibits an increased amount of myelin production (as compared to cells without the modification) and/or cells that exhibit an improvement in the functional ability of myelin produced by the cells.

The term "indel" refers to the insertion, deletion, combinations thereof of bases in the nucleotide sequence of an organism or cell. Insertion (also called an insertion mutation) is the addition of one or more nucleotide base pairs into a nucleotide sequence whereas a deletion refers to a mutation in which a part of a nucleotide sequence is removed. Any number of nucleotides can be inserted or deleted, from a single base to an entire piece of chromosome.

"Nonsense-mediated decay" refers to a translation-coupled mechanism in eukaryotic cells that eliminates mRNA transcripts containing premature translation-termination codons (PTCs). In mammalian cells, NMD is also linked to pre-mRNA splicing, as in many instances strong mRNA reduction occurs only when the PTC is located upstream of an intron.

Overview

Embodiments described herein relate to methods of generating cells genetically modified to disrupt or inactivate the proteolipid protein 1 (PLP1) gene and methods for their use in the treatment of human myelin-related disorders. The present application is based, in part, on the demonstration of efficient site directed induction of PLP1-inactivating indels in glial cells and in zygotes. It has been shown that nuclease-mediated editing of the PLP1 gene restores normal function and full lifespan in the jimpy mouse model of the myelin-related disorder Pelizaeus-Merzbacher Disease (PMD) as well as restoring function in PMD model glial cells in vitro. Without being bound by theory, it is believed that PLP1-related toxicity is bypassed by inactivation of the PLP1 gene, thereby enhancing the ability of the modified glial cell or oligodendrocytes to make functional myelin.

Described herein is the site-specific insertion or deletion (indels) in the PLP1 gene or its regulatory elements. When targeting the PLP1 gene, this will provide effective and permanent inactivation or reduction of PLP1 expression. Site-directed nuclease or gene editing PLP1 gene disrupting compositions may be delivered, for example, using one or more AAV vectors, integrase-defective lentiviral vectors (IDLVs), and/or nucleic acids such as plasmids, minicircle plasmids and oligonucleotides.

Also described herein, is precise in situ editing of PLP1 gene or its genetic regulatory elements, in order to create enhanced functional myelin production capabilities in neural stem cells (NSCs) and/or oligodendrocyte precursor cells (OPCs) and their progeny. Nuclease or gene editing mediated introduction of disruptive mutations in situ into the endogenous PLP1 gene in NSCs and/or OPCs confers these enhanced capabilities to the progeny of the edited cells. Additionally, specific knock out or mutation of a PLP1 regulatory gene in situ into the endogenous genes in NSCs or OPCs confers enhanced/improved functional myelin production in the progeny of the cells.

Cells and methods as described can be transplanted into animal models and/or human patients without significantly impacting cell function and viability. In addition, the cells maintain their ability to persist in vivo, and can enhance functional myelin production in the subject after transplantation.

Practice of the methods, as well as preparation and use of the compositions disclosed herein employ, unless otherwise indicated, conventional techniques in molecular biology, biochemistry, chromatin structure and analysis, computational chemistry, cell culture, recombinant DNA and related fields as are within the skill of the art. These techniques are fully explained in the literature. See, for example, Sambrook et al. MOLECULAR CLONING: A LABORATORY MANUAL, Second edition, Cold Spring Harbor Laboratory Press, 1989 and Third edition, 2001; Ausubel et al., CURRENT PROTOCOLS IN MOLECULAR BIOLOGY, John Wiley & Sons, New York, 1987 and periodic updates; the series METHODS IN ENZYMOLOGY, Academic Press, San Diego; Wolffe, CHROMATIN STRUCTURE AND FUNCTION, Third edition, Academic Press, San Diego, 1998; METHODS IN ENZYMOLOGY, Vol. 304, "Chromatin" (P. M. Wassarman and A. P. Wolffe, eds.), Academic Press, San Diego, 1999; and METHODS IN MOLECULAR BIOLOGY, Vol. 119, "Chromatin Protocols" (P. B. Becker, ed.) Humana Press, Totowa, 1999.

Further aspects of the invention are described in the sections below.

Fusion Molecules

Described herein are compositions, for example nucleases, that are useful for cleavage of a selected target gene in a cell (e.g., PLP1 or genetic regulatory elements thereof). In certain embodiments, one or more components of the fusion molecules (e.g., nucleases) are naturally occurring. In other embodiments, one or more of the components of the fusion molecules (e.g., nucleases) are non-naturally occurring, i.e., engineered in the DNA-binding domain(s) and/or cleavage domain(s). For example, the DNA-binding domain of a naturally-occurring nuclease may be altered to bind to a selected target site (e.g., a meganuclease that has been engineered to bind to site different than the cognate binding site). In other embodiments, the nuclease comprises heterologous DNA-binding and cleavage domains (e.g., zinc finger nucleases; TAL-effector domain DNA binding proteins; meganuclease DNA-binding domains with heterologous cleavage domains).

DNA-Binding Domains

In certain embodiments, the composition and methods described herein employ a meganuclease (homing endonuclease) DNA-binding domain for binding to the donor molecule and/or binding to the region of interest in the genome of the cell. Naturally-occurring meganucleases recognize 15-40 base-pair cleavage sites and are commonly grouped into four families: the LAGLIDADG family, the GIY-YIG family, the His-Cyst box family and the HNH family. Exemplary homing endonucleases include I-SceI, I-CeuI, PI-PspI, PI-SceI-SceIV, I-CsmI, I-PanI, I-SceII, I-PpoI, I-SceIII, I-CreI, I-TevI, I-TevII and I-TevIII. Their recognition sequences are known. See, also, U.S. Pat. Nos. 5,420,032; 6,833,252; Belfort et al. (1997) *Nucleic Acids Res.* 25:3379-3388; Dujon et al. (1989) *Gene* 82:115-118; Perler et al. (1994) Nucleic Acids Res. 22, 1125-1127; Jasin (1996) *Trends Genet.* 12:224-228; Gimble et al. (1996) *J. Mol. Biol.* 263:163-180; Argast et al. (1998) *J. Mol. Biol.*

280: 345-353 and the New England Biolabs catalogue. In addition, the DNA-binding specificity of homing endonucleases and meganucleases can be engineered to bind non-natural target sites. See, for example, Chevalier et al. (2002) *Molec. Cell* 10:895-905; Epinat et al. (2003) *Nucleic Acids Res.* 31:2952-2962; Ashworth et al. (2006) *Nature* 441:656-659; Paques et al. (2007) *Current Gene Therapy* 7:49-66; U.S. Patent Publication No. 20070117128. The DNA-binding domains of the homing endonucleases and meganucleases may be altered in the context of the nuclease as a whole (i.e., such that the nuclease includes the cognate cleavage domain) or may be fused to a heterologous cleavage domain.

In other embodiments, the DNA-binding domain of one or more of the nucleases used in the methods and compositions described herein comprises a naturally occurring or engineered (non-naturally occurring) TAL effector DNA binding domain. See, e.g., U.S. Pat. No. 8,586,526, incorporated by reference in its entirety herein. The plant pathogenic bacteria of the genus *Xanthomonas* are known to cause many diseases in important crop plants. Pathogenicity of *Xanthomonas* depends on a conserved type III secretion (T3S) system which injects more than 25 different effector proteins into the plant cell. Among these injected proteins are transcription activator-like (TAL) effectors which mimic plant transcriptional activators and manipulate the plant transcriptome (see Kay et al (2007) *Science* 318:648-651). These proteins contain a DNA binding domain and a transcriptional activation domain. One of the most well characterized TAL-effectors is AvrBs3 from *Xanthomonas campestgris* pv. *Vesicatoria* (see Bonas et al (1989) *Mol Gen Genet* 218: 127-136 and WO2010079430). TAL-effectors contain a centralized domain of tandem repeats, each repeat containing approximately 34 amino acids, which are key to the DNA binding specificity of these proteins. In addition, they contain a nuclear localization sequence and an acidic transcriptional activation domain (for a review see Schornack S, et al. (2006) *J Plant Physiol* 163(3): 256-272). In addition, in the phytopathogenic bacteria *Ralstonia solanacearum* two genes, designated brg11 and hpx17 have been found that are homologous to the AvrBs3 family of Xanthomonasin the *R. solanacearum* biovar 1 strain GMI1000 and in the biovar 4 strain RS 1000 (See Heuer et at (2007) *Appl and Envir Micro* 73(13): 4379-4384). These genes are 98.9% identical in nucleotide sequence to each other but differ by a deletion of 1,575 bp in the repeat domain of hpx17. However, both gene products have less than 40% sequence identity with AvrBs3 family proteins of *Xanthomonas*. See, e.g., U.S. Pat. No. 8,586,526, incorporated by reference in its entirety herein.

Specificity of these TAL effectors depends on the sequences found in the tandem repeats. The repeated sequence comprises approximately 102 bp and the repeats are typically 91-100% homologous with each other (Bonas et al, ibid). Polymorphism of the repeats is usually located at positions 12 and 13 and there appears to be a one-to-one correspondence between the identity of the hypervariable diresidues (RVD) at positions 12 and 13 with the identity of the contiguous nucleotides in the TAL-effector's target sequence (see Moscou and Bogdanove, (2009) *Science* 326:1501 and Boch et al (2009) *Science* 326:1509-1512). Experimentally, the natural code for DNA recognition of these TAL-effectors has been determined such that an HD sequence at positions 12 and 13 leads to a binding to cytosine (C), NG binds to T, NI to A, C, G or T, NN binds to A or G, and ING binds to T. These DNA binding repeats have been assembled into proteins with new combinations and numbers of repeats, to make artificial transcription factors that are able to interact with new sequences and activate the expression of a non-endogenous reporter gene in plant cells (Boch et al, ibid). Engineered TAL proteins have been linked to a FokI cleavage half domain to yield a TAL effector domain nuclease fusion (TALEN). See, e.g., U.S. Pat. No. 8,586,526; Christian et al. ((2010) <*Genetics* epub 10.1534/genetics. 110.120717). In certain embodiments, TALE domain comprises an N-cap and/or C-cap as described in U.S. Pat. No. 8,586,526.

In certain embodiments, the DNA binding domain of one or more of the nucleases used for in vivo cleavage and/or targeted cleavage of the genome of a cell comprises a zinc finger protein. Preferably, the zinc finger protein is non-naturally occurring in that it is engineered to bind to a target site of choice. See, for example, See, for example, Beerli et al. (2002) *Nature Biotechnol.* 20:135-141; Pabo et al. (2001) *Ann. Rev. Biochem.* 70:313-340; Isalan et al. (2001) *Nature Biotechnol.* 19:656-660; Segal et al. (2001) *Curr. Opin. Biotechnol.* 12:632-637; Choo et al. (2000) *Curr. Opin. Struct. Biol.* 10:411-416; U.S. Pat. Nos. 6,453,242; 6,534,261; 6,599,692; 6,503,717; 6,689,558; 7,030,215; 6,794,136; 7,067,317; 7,262,054; 7,070,934; 7,361,635; 7,253,273; and U.S. Patent Publication Nos. 2005/0064474; 2007/0218528; 2005/0267061, all incorporated herein by reference in their entireties.

An engineered zinc finger binding domain can have a novel binding specificity, compared to a naturally-occurring zinc finger protein. Engineering methods include, but are not limited to, rational design and various types of selection. Rational design includes, for example, using databases comprising triplet (or quadruplet) nucleotide sequences and individual zinc finger amino acid sequences, in which each triplet or quadruplet nucleotide sequence is associated with one or more amino acid sequences of zinc fingers which bind the particular triplet or quadruplet sequence. See, for example, co-owned U.S. Pat. Nos. 6,453,242 and 6,534,261, incorporated by reference herein in their entireties.

Exemplary selection methods, including phage display and two-hybrid systems, are disclosed in U.S. Pat. Nos. 5,789,538; 5,925,523; 6,007,988; 6,013,453; 6,410,248; 6,140,466; 6,200,759; and 6,242,568; as well as WO 98/37186; WO 98/53057; WO 00/27878; WO 01/88197 and GB 2,338,237. In addition, enhancement of binding specificity for zinc finger binding domains has been described, for example, in co-owned WO 02/077227.

In addition, as disclosed in these and other references, zinc finger domains and/or multi-fingered zinc finger proteins may be linked together using any suitable linker sequences, including for example, linkers of 5 or more amino acids in length. See, also, U.S. Pat. Nos. 6,479,626; 6,903,185; and 7,153,949 for exemplary linker sequences 6 or more amino acids in length. The proteins described herein may include any combination of suitable linkers between the individual zinc fingers of the protein.

In some aspects, the DNA-binding domain targets a PLP1 gene or PLP1 genetic regulatory element.

Selection of target sites; ZFPs and methods for design and construction of fusion proteins (and polynucleotides encoding same) are known to those of skill in the art and described in detail in U.S. Pat. Nos. 6,140,081; 5,789,538; 6,453,242; 6,534,261; 5,925,523; 6,007,988; 6,013,453; 6,200,759; WO 95/19431; WO 96/06166; WO 98/53057; WO 98/54311; WO 00/27878; WO 01/60970 WO 01/88197; WO 02/099084; WO 98/53058; WO 98/53059; WO 98/53060; WO 02/016536 and WO 03/016496.

In addition, as disclosed in these and other references, zinc finger domains and/or multi-fingered zinc finger proteins may be linked together using any suitable linker sequences, including for example, linkers of 5 or more amino acids in length. See, also, U.S. Pat. Nos. 6,479,626; 6,903,185; and 7,153,949 for exemplary linker sequences 6 or more amino acids in length. The proteins described herein may include any combination of suitable linkers between the individual zinc fingers of the protein.

In certain embodiments, the DNA-binding domain is part of a CRISPR/Cas nuclease system. See, e.g., U.S. Pat. No. 8,697,359 and U.S. patent application Ser. No. 14/278,903. The CRISPR (clustered regularly interspaced short palindromic repeats) locus, which encodes RNA components of the system, and the cas (CRISPR-associated) locus, which encodes proteins (Jansen et al., 2002. *Mol. Microbiol.* 43: 1565-1575; Makarova et al., 2002. *Nucleic Acids Res.* 30: 482-496; Makarova et al., 2006. *Biol. Direct* 1: 7; Haft et al., 2005. *PLoS Comput. Biol.* 1: e60) make up the gene sequences of the CRISPR/Cas nuclease system. CRISPR loci in microbial hosts contain a combination of CRISPR-associated (Cas) genes as well as non-coding RNA elements capable of programming the specificity of the CRISPR-mediated nucleic acid cleavage. CRISPR-Cas systems are separated into two classes. Class 1 uses several Cas proteins together with the CRISPR RNAs (crRNA) to build a functional endonuclease. Class 2 CRISPR systems use a single Cas protein with a crRNA The Class 2 Type II CRISPR is one of the most well characterized systems and carries out targeted DNA double-strand break in four sequential steps. First, two non-coding RNA, the pre-crRNA array and tracrRNA, are transcribed from the CRISPR locus. Second, tracrRNA hybridizes to the repeat regions of the pre-crRNA and mediates the processing of pre-crRNA into mature crRNAs containing individual spacer sequences. Third, the mature crRNA:tracrRNA complex directs functional domain (e.g., nuclease such as Cas) to the target DNA via Watson-Crick base-pairing between the spacer on the crRNA and the protospacer on the target DNA next to the protospacer adjacent motif (PAM), an additional requirement for target recognition. Finally, Cas9 mediates cleavage of target DNA to create a double-stranded break within the protospacer. Activity of the CRISPR/Cas system comprises of three steps: (i) insertion of alien DNA sequences into the CRISPR array to prevent future attacks, in a process called 'adaptation', (ii) expression of the relevant proteins, as well as expression and processing of the array, followed by (iii) RNA-mediated interference with the alien nucleic acid. Thus, in the bacterial cell, several of the so-called 'Cas' proteins are involved with the natural function of the CRISPR/Cas system and serve roles in functions such as insertion of the alien DNA etc.

In certain embodiments, Cas protein may be a "functional derivative" of a naturally occurring Cas protein. A "functional derivative" of a native sequence polypeptide is a compound having a qualitative biological property in common with a native sequence polypeptide. "Functional derivatives" include, but are not limited to, fragments of a native sequence and derivatives of a native sequence polypeptide and its fragments, provided that they have a biological activity in common with a corresponding native sequence polypeptide. A biological activity contemplated herein is the ability of the functional derivative to hydrolyze a DNA substrate into fragments. The term "derivative" encompasses both amino acid sequence variants of polypeptide, covalent modifications, and fusions thereof such as derivative Cas proteins. Suitable derivatives of a Cas polypeptide or a fragment thereof include but are not limited to mutants, fusions, covalent modifications of Cas protein or a fragment thereof. Cas protein, which includes Cas protein or a fragment thereof, as well as derivatives of Cas protein or a fragment thereof, may be obtainable from a cell or synthesized chemically or by a combination of these two procedures. The cell may be a cell that naturally produces Cas protein, or a cell that naturally produces Cas protein and is genetically engineered to produce the endogenous Cas protein at a higher expression level or to produce a Cas protein from an exogenously introduced nucleic acid, which nucleic acid encodes a Cas that is same or different from the endogenous Cas. In some case, the cell does not naturally produce Cas protein and is genetically engineered to produce a Cas protein. In some embodiments, the Cas protein is a small Cas9 ortholog for delivery via an AAV vector (Ran et al. (2015) *Nature* 510, p. 186). In particular embodiments, the Cas protein is a SaCas9 or a SpCas9 Cas protein.

In certain embodiments, the Cas9 protein is a mammalian Cas9, or a Cas9 from *Streptococcus pyogenes, Neisseria Meningitidis, Streptococcus thermophilus, Streptococcus pneumnoniae, Campylobacter coli, Campylobacter jejuni, Streptococcus mutans, Pasteurella multocida, Bifidobacterium longum, Bacillus smithii, Treponema denticola, mycoplasma canis* or *Enterococcus faecalis, Sutterella wadsworthensis, Filifactor alocis, Lactobacillus johnsonii, Campylobacter lari, Corynebacter diptheriae, Parvibaculum lavamentivorans, Mycoplasma gallisepticum, Staphylococcus aureus* subsubspecies *Aureus, Legionella pneumophila Paris, Treponema denticola, Staphylococcus pseudintermedius,* or *Neisseria cinerea.*

In certain embodiments, the Cas9 protein has one or more nuclear localization sequences.

In some embodiments, the DNA-binding domain is part of a Class 2 Type V CRISPR/Cas Cpf1 system Like Cas9, Cpf1 nucleases contain a RuvC-like endonuclease domain, but they lack Cas9's second HNH endonuclease domain and N-terminal alpha-helical recognition lobe. Cpf1 cleaves DNA in a staggered pattern and requires only one RNA rather than the two (tracrRNA and crRNA) needed by Cas9 for cleavage. Cpf1's staggered cleavage pattern opens up the possibility of directional gene transfer, analogous to traditional restriction enzyme cloning. Sticky-end mediated gene transfer can be particularly helpful for targeting non-dividing cells, which are difficult to modify through homology-directed repair (HDR). Cpf1 also expands the number of sites that can be targeted by CRISPR to AT-rich regions or AT-rich genomes that lack the 3'-NGG PAM sites favored by SpCas9 (see e.g., Zetsche et al. (2015) *Cell* 163(3):759-771 and Makarova et al., (2015) *Nature Reviews Microbiology* 13(11):722-736.

In some embodiments, the DNA binding domain is part of an Argonaute endonuclease system suitable for genome editing in human cells. An exemplary Argonaute endonuclease system suitable for genome editing in human cells can include an Argonaute DNA-guided endonuclease from *Natronobacterium gregoryi* (NgAgo) (Gao et al. (2016) *Nature Biotechnology.* 34: 768-773). NgAgo binds 5' phosphorylated single-stranded guide DNA (gDNA) of ~24 nucleotides and efficiently creates site-specific DNA double-strand breaks when loaded with the gDNA. Using 5' phosphorylated ssDNAs as guide molecules reduces the possibility of cellular oligonucleotides misleading NgAgo. A guide molecule can only be attached to NgAgo during the expression of the protein. Once the guide is loaded, NgAgo cannot swap free floating ssDNA for its gDNA. The NgAgo-gDNA system does not require a protospacer-adjacent motif (PAM), as does Cas9, and appears to possess a low tolerance to guide-target mismatches and high efficiency in editing (G+C)-rich genomic targets Exogenous guide DNAs of arbitrary DNA sequence can be loaded onto the NgAgo protein. Since the specificity of NgAgo cleavage is directed by the guide DNA, a NgAgo-DNA complex formed with an exogenous, investigator-specified guide DNA will therefore direct NgAgo target DNA cleavage to a complementary investigator-specified target DNA. In this way, one may create a targeted double-strand break in DNA. Use of the NgAgo-guide DNA system (or orthologous Ago-guide DNA systems from other organisms) allows for targeted cleavage of genomic DNA within cells. Such cleavage can be either single- or double-stranded. For cleavage of mammalian genomic DNA, it would be preferable to use of a version of NgAgo codon optimized for expression in mammalian cells. Further, it might be preferable to treat cells with an NgAgo-DNA complex formed in vitro where the NgAgo protein is fused to a cell-penetrating peptide. Further, it might be preferable to use a version of the NgAgo protein that has been altered via mutagenesis to have improved activity at 37° C. Ago-RNA-mediated DNA cleavage could be used to affect a panopoly of outcomes including gene knock-out, targeted gene addition, gene correction, targeted gene deletion using techniques standard in the art for exploitation of DNA breaks.

Thus, the nuclease includes a DNA-binding domain in that specifically binds to a target site in any gene (e.g., PLP1) into which it is desired to insert or delete bases (create indels) to inactivate or reduce gene expression.

Cleavage Domains

Any suitable cleavage domain can be operatively linked to a DNA-binding domain to form a nuclease. For example, ZFP DNA-binding domains have been fused to nuclease domains to create ZFNs—a functional entity that is able to recognize its intended nucleic acid target through its engineered (ZFP) DNA binding domain and cause the DNA to be cut near the ZFP binding site via the nuclease activity, including for use in genome modification in a variety of organisms. See, for example, U.S. Patent Publications 20030232410; 20050208489; 20050026157; 20050064474; 20060188987; 20060063231; and International Publication WO 07/014275. Likewise, TALE DNA-binding domains have been fused to nuclease domains to create TALENs. See, e.g., U.S. Pat. No. 8,586,526.

As noted above, the cleavage domain may be heterologous to the DNA-binding domain, for example a zinc finger DNA-binding domain and a cleavage domain from a nuclease or a TALEN DNA-binding domain and a cleavage domain, or meganuclease DNA-binding domain and cleavage domain from a different nuclease. Heterologous cleavage domains can be obtained from any endonuclease or exonuclease. Exemplary endonucleases from which a cleavage domain can be derived include, but are not limited to, restriction endonucleases and homing endonucleases. Additional enzymes which cleave DNA are known (e.g., S1 Nuclease; mung bean nuclease; pancreatic DNase I; micrococcal nuclease; yeast HO endonuclease. One or more of these enzymes (or functional fragments thereof) can be used as a source of cleavage domains and cleavage half-domains.

Similarly, a cleavage half-domain can be derived from any nuclease or portion thereof, as set forth above, that requires dimerization for cleavage activity. In general, two fusion proteins are required for cleavage if the fusion proteins comprise cleavage half-domains. Alternatively, a single protein comprising two cleavage half-domains can be used. The two cleavage half-domains can be derived from the same endonuclease (or functional fragments thereof), or each cleavage half-domain can be derived from a different endonuclease (or functional fragments thereof). In addition, the target sites for the two fusion proteins are preferably disposed, with respect to each other, such that binding of the two fusion proteins to their respective target sites places the cleavage half-domains in a spatial orientation to each other that allows the cleavage half-domains to form a functional cleavage domain, e.g., by dimerizing. Thus, in certain embodiments, the near edges of the target sites are separated by 5-8 nucleotides or by 15-18 nucleotides. However any integral number of nucleotides or nucleotide pairs can intervene between two target sites (e.g., from 2 to 50 nucleotide pairs or more). In general, the site of cleavage lies between the target sites.

Restriction endonucleases (restriction enzymes) are present in many species and are capable of sequence-specific binding to DNA (at a recognition site), and cleaving DNA at or near the site of binding. Certain restriction enzymes (e.g., Type IIS) cleave DNA at sites removed from the recognition site and have separable binding and cleavage domains. For example, the Type IIS enzyme Fok I catalyzes double-stranded cleavage of DNA, at 9 nucleotides from its recognition site on one strand and 13 nucleotides from its recognition site on the other. See, for example, U.S. Pat. Nos. 5,356,802; 5,436,150 and 5,487,994; as well as Li et al. (1992) *Proc. Natl. Acad. Sci. USA* 89:4275-4279; Li et al. (1993) *Proc. Natl. Acad. Sci. USA* 90:2764-2768; Kim et al. (1994a) *Proc. Natl. Acad. Sci. USA* 91:883-887; Kim et al. (1994b) *J. Biol. Chem.* 269:31,978-31,982. Thus, in one embodiment, fusion proteins comprise the cleavage domain (or cleavage half-domain) from at least one Type IIS restriction enzyme and one or more zinc finger binding domains, which may or may not be engineered.

An exemplary Type IIS restriction enzyme, whose cleavage domain is separable from the binding domain, is Fok I. This particular enzyme is active as a dimer. Bitinaite et al. (1998) *Proc. Natl. Acad. Sci. USA* 95: 10,570-10,575. Accordingly, for the purposes of the present disclosure, the portion of the Fok I enzyme used in the disclosed fusion proteins is considered a cleavage half-domain. Thus, for targeted double-stranded cleavage and/or targeted replacement of cellular sequences using zinc finger-Fok I fusions, two fusion proteins, each comprising a Fok I cleavage half-domain, can be used to reconstitute a catalytically active cleavage domain. Alternatively, a single polypeptide molecule containing a zinc finger binding domain and two Fok I cleavage half-domains can also be used. Parameters for targeted cleavage and targeted sequence alteration using zinc finger-Fok I fusions are provided elsewhere in this disclosure.

A cleavage domain or cleavage half-domain can be any portion of a protein that retains cleavage activity, or that retains the ability to multimerize (e.g., dimerize) to form a functional cleavage domain.

Exemplary Type IIS restriction enzymes are described in International Publication WO 07/014275, incorporated herein in its entirety. Additional restriction enzymes also contain separable binding and cleavage domains, and these are contemplated by the present disclosure. See, for example, Roberts et al. (2003) *Nucleic Acids Res.* 31:418-420.

In certain embodiments, the cleavage domain comprises one or more engineered cleavage half-domain (also referred to as dimerization domain mutants) that minimize or prevent homodimerization, as described, for example, in U.S. Patent Publication Nos. 20050064474; 20060188987; 20070305346 and 20080131962, the disclosures of all of which are incorporated by reference in their entireties herein. Amino acid residues at positions 446, 447, 479, 483, 484, 486, 487, 490, 491, 496, 498, 499, 500, 531, 534, 537, and 538 of FokI are all targets for influencing dimerization of the FokI cleavage half-domains.

Cleavage domains with more than one mutation may be used, for example mutations at positions 490 (E→K) and 538 (I→K) in one cleavage half-domain to produce an engineered cleavage half-domain designated "E490K: I538K" and by mutating positions 486 (Q→E) and 499 (I→L) in another cleavage half-domain to produce an engineered cleavage half-domain designated "Q486E:I499L;" mutations that replace the wild type Gln (Q) residue at position 486 with a Glu (E) residue, the wild type Iso (I) residue at position 499 with a Leu (L) residue and the wild-type Asn (N) residue at position 496 with an Asp (D) or Glu (E) residue (also referred to as a "ELD" and "ELE" domains, respectively); engineered cleavage half-domain comprising mutations at positions 490, 538 and 537 (numbered relative to wild-type FokI), for instance mutations that replace the wild type Glu (E) residue at position 490 with a Lys (K) residue, the wild type Iso (I) residue at position 538 with a Lys (K) residue, and the wild-type His (H) residue at position 537 with a Lys (K) residue or a Arg (R) residue (also referred to as "KKK" and "KKR" domains, respectively); and/or engineered cleavage half-domain comprises mutations at positions 490 and 537 (numbered relative to wild-type FokI), for instance mutations that replace the wild type Glu (E) residue at position 490 with a Lys (K) residue and the wild-type His (H) residue at position 537 with a Lys (K) residue or a Arg (R) residue (also referred to as "KIK" and "KIR" domains, respectively). See, e.g., U.S. Pat. Nos. 7,914,796; 8,034,598 and 8,623,618, the disclosures of which are incorporated by reference in its entirety for all purposes. In other embodiments, the engineered cleavage half domain comprises the "Sharkey" and/or "Sharkey'" mutations (see Guo et al, (2010) *J. Mol. Biol.* 400(1):96-107)

Alternatively, nucleases may be assembled in vivo at the nucleic acid target site using so-called "split-enzyme" technology (see, e.g., U.S. Patent Publication No. 20090068164). Components of such split enzymes may be expressed either on separate expression constructs, or can be linked in one open reading frame where the individual components are separated, for example, by a self-cleaving 2A peptide or IRES sequence. Components may be individual zinc finger binding domains or domains of a meganuclease nucleic acid binding domain.

Nucleases can be screened for activity prior to use, for example in a yeast-based chromosomal system as described in U.S. Pat. No. 8,563,314.

The Cas9 related CRISPR/Cas system comprises two RNA non-coding components: tracrRNA and a pre-crRNA array containing nuclease guide sequences (spacers) interspaced by identical direct repeats (DRs). To use a CRISPR/Cas system to accomplish genome engineering, both functions of these RNAs must be present (see Cong et al, (2013) *Sciencexpress* 1/10.1126/science 1231143). In some embodiments, the tracrRNA and pre-crRNAs are supplied via separate expression constructs or as separate RNAs.

In other embodiments, a chimeric RNA is constructed where an engineered mature crRNA (conferring target specificity) is fused to a tracrRNA (supplying interaction with the Cas9) to create a chimeric cr-RNA-tracrRNA hybrid (also termed a single guide RNA or sgRNA). Therefore, along with Cas9 nuclease, modification of PLP1 genes in a method of the invention require the introduction of an sgRNA containing an approximately 20 base sequence specific to the target DNA 5' of a non-variable scaffold sequence. sgRNA can be delivered as RNA or by transforming with a plasmid with the sgRNA-coding sequence under a promoter. In particular embodiments, an sgRNA sequence for use in modifying a PLP1 gene includes, but is not limited to, AAGACCACCATCTGCGGCAANGG (SEQ ID NO:1) and CCAGCAGGAGGGCCCCATAANGG (SEQ ID NO:2) which target Exon 3 of the PLP1 gene, GTCAGAGTGC-CAAAGACATGGNNGRRT (SEQ ID NO:3) that targets Exon 1 of the PLP1 gene.

Target Sites

As described in detail above, DNA-binding domains can be engineered to bind to any sequence of choice. An engineered DNA-binding domain can have a novel binding specificity, compared to a naturally-occurring DNA-binding domain.

In certain embodiments, the target site(s) is(are) in an exon of the endogenous PLP1 gene. Non-limiting examples of suitable genomic exonic regions for targeting include, exons 1 or 3 or 7 of PLP1. In some embodiments, the target site includes about an 80 nucleotide segment on the 5' of exon 3 of PLP1.

In certain embodiments, the nuclease targets the PLP1 gene. In certain embodiments, the nuclease targets a PLP1 genetic regulatory element such as a promoter or an enhancer.

Donors

In certain embodiments, the present disclosure relates to nuclease-mediated targeted integration of an exogenous sequence into the genome of a cell. As noted above, insertion of an exogenous sequence (also called a "donor sequence" or "donor" or "transgene"), for example for deletion of a specified region (such as deleting one copy of the PLP1 gene duplicate which appears in about 70% of the PMD patients) and/or correction of a mutant gene (such as a PLP1 point mutation appearing in about 30% of the PMD patients) or for increased expression of a wild-type gene. It will be readily apparent that the donor sequence is typically not identical to the genomic sequence where it is placed. A donor sequence can contain a non-homologous sequence flanked by two regions of homology to allow for efficient HDR at the location of interest or can be integrated via non-homology directed repair mechanisms. Additionally, donor sequences can comprise a vector molecule containing sequences that are not homologous to the region of interest in cellular chromatin. A donor molecule can contain several, discontinuous regions of homology to cellular DNA. Further, for targeted insertion of sequences not normally present in a region of interest, said sequences can be present in a donor nucleic acid molecule and flanked by regions of homology to sequence in the region of interest.

As with nucleases, the donors can be introduced into any form. In certain embodiments, the donors may be introduced using DNA and/or viral vectors by methods known in the art. See, e.g., U.S. Patent Publication Nos. 20100047805 and 20110207221. The donor may be introduced into the cell in double- or single-stranded form. The donor may be introduced into the cell in circular or linear form. If introduced in linear form, the ends of the donor sequence can be protected (e.g., from exonucleolytic degradation) by methods known to those of skill in the art. For example, one or more dideoxynucleotide residues are added to the 3' terminus of a linear molecule and/or self-complementary oligonucleotides are ligated to one or both ends. See, for example, Chang et al. (1987) *Proc. Natl. Acad. Sci. USA* 84:4959-4963; Nehls et al. (1996) *Science* 272:886-889. Additional methods for protecting exogenous polynucleotides from degradation include, but are not limited to, addition of terminal amino group(s) and the use of modified internucleotide linkages such as, for example, phosphorothioates, phosphoramidates, and O-methyl ribose or deoxyribose residues.

In certain embodiments, the donor includes sequences (e.g., coding sequences, also referred to as transgenes) greater than 1 kb in length, for example between 2 and 200 kb, between 2 and 10 kb (or any value therebetween). The donor may also include at least one nuclease target site. In certain embodiments, the donor includes at least 2 target sites, for example for a pair of ZFNs, TALENs, NgAgo or CRISPR/Cas nucleases. Typically, the nuclease target sites are outside the transgene sequences, for example, 5' and/or 3' to the transgene sequences, for cleavage of the transgene. The nuclease cleavage site(s) may be for any nuclease(s). In certain embodiments, the nuclease target site(s) contained in the double-stranded donor are for the same nuclease(s) used to cleave the endogenous target into which the cleaved donor is integrated via homology-independent methods.

The donor can be inserted so that its expression is driven by the endogenous promoter at the integration site, namely the promoter that drives expression of the endogenous gene into which the donor is inserted. However, it will be apparent that the donor may comprise a promoter and/or enhancer, for example a constitutive promoter or an inducible or tissue specific promoter.

The donor molecule may be inserted into an endogenous gene such that all, some or none of the endogenous gene is expressed. In some embodiments, the transgene is integrated into a PLP1 or PLP1 genetic regulatory element such that PLP1 is inactivated or its expression reduced.

Furthermore, although not required for expression, exogenous sequences may also include transcriptional or translational regulatory or other sequences, for example, promoters, enhancers, insulators, internal ribosome entry sites, sequences encoding 2A peptides and/or polyadenylation signals. Additionally, splice acceptor sequences may be included. Exemplary splice acceptor site sequences are known to those of skill in the art and include, by way of example only, CTGACCTCTTCTCTTCCTCCCACAG, (SEQ ID NO: 4) (from the human HBB gene) and TTTCTCTCCACAG (SEQ ID NO: 5) (from the human Immunoglobulin-gamma gene).

The donor sequences (transgenes and/or repair templates) described herein may be isolated from plasmids, cells or other sources using standard techniques known in the art such as PCR. Donors for use can include varying types of topology, including circular supercoiled, circular relaxed, linear and the like. Alternatively, they may be chemically synthesized using standard oligonucleotide synthesis techniques. In addition, donors may be methylated or lack methylation. Donors may be in the form of bacterial or yeast artificial chromosomes (BACs or YACs).

The donor polynucleotides described herein may include one or more non-natural bases and/or backbones. In particular, insertion of a donor molecule with methylated cytosines may be carried out using the methods described herein to achieve a state of transcriptional quiescence in a region of interest.

The exogenous (donor) polynucleotide may comprise any sequence of interest (exogenous sequence). Exemplary exogenous sequences include, but are not limited to any polypeptide coding sequence (e.g., cDNAs), promoter sequences, enhancer sequences, epitope tags, marker genes, cleavage enzyme recognition sites and various types of expression constructs. Marker genes include, but are not limited to, sequences encoding proteins that mediate antibiotic resistance (e.g., ampicillin resistance, neomycin resistance, G418 resistance, puromycin resistance), sequences encoding colored or fluorescent or luminescent proteins (e.g., green fluorescent protein, enhanced green fluorescent protein, red fluorescent protein, luciferase), and proteins which mediate enhanced cell growth and/or gene amplification (e.g., dihydrofolate reductase). Epitope tags include, for example, one or more copies of FLAG, His, myc, Tap, HA or any detectable amino acid sequence.

In some embodiments, the donor further comprises a polynucleotide encoding any polypeptide of which expression in the cell is desired, including, but not limited to antibodies, antigens, enzymes, receptors (cell surface or nuclear), hormones, lymphokines, cytokines, reporter polypeptides, growth factors, and functional fragments of any of the above. The coding sequences may be, for example, cDNAs.

In certain embodiments, the exogenous sequences can comprise a marker gene (described above), allowing selection of cells that have undergone targeted integration, and a linked sequence encoding an additional functionality. Non-limiting examples of marker genes include GFP, drug selection marker(s) and the like.

In certain embodiments, the donor may include, for example, wild-type genes to replace mutated deleterious endogenous sequences. For example, a wild-type (or other functional) gene sequence may be inserted into the genome of a stem cell in which the endogenous copy of the gene is mutated. In other embodiments, the donor may include, for example, a mutant gene to replace wild-type endogenous genes. For example, a wild-type PLP1 sequence may be inserted into the genome of a stem cell to mutate the endogenous deleterious, mutant PLP1 gene involved in a myelin-related disorder.

Construction of such expression cassettes, following the teachings of the present specification, utilizes methodologies well known in the art of molecular biology (see, for example, Ausubel or Maniatis). Before use of the expression cassette to generate a transgenic animal, the responsiveness of the expression cassette to the stress-inducer associated with selected control elements can be tested by introducing the expression cassette into a suitable cell line (e.g., primary cells, transformed cells, or immortalized cell lines).

Furthermore, although not required for expression, exogenous sequences may also include transcriptional or translational regulatory sequences, for example, promoters, enhancers, insulators, internal ribosome entry sites, sequences encoding 2A peptides and/or polyadenylation signals. Further, the control elements of the genes of interest can be operably linked to reporter genes to create chimeric genes (e.g., reporter expression cassettes).

Targeted insertion of non-coding nucleic acid sequence may also be achieved. Sequences encoding antisense RNAs, RNAi, siRNA, shRNAs, and micro RNAs (miRNAs) may also be used for targeted insertions.

In additional embodiments, the donor nucleic acid may comprise non-coding sequences that are specific target sites for additional nuclease designs. Subsequently, additional nucleases may be expressed in cells such that the original donor molecule is cleaved and modified by insertion of another donor molecule of interest. In this way, reiterative integrations of donor molecules may be generated allowing for trait stacking at a particular locus of interest or at a safe harbor locus.

In some embodiments, the therapeutic genetic modifying compositions described herein can be further screened using an in vivo assay that assesses remyelination and reduction of clinical severity in the jimpy mouse model of Pelizaeus-Merzbacher Disease (PMD).

Gene Silencing

In certain embodiments, the nuclease targets the PLP1 gene. In certain embodiments, the nuclease targets a PLP1 genetic regulatory element such as a promoter or an enhancer.

In some embodiments, an endogenous PLP1 gene product or a PLP1 regulatory element gene product that promotes PLP1 expression is modified to decrease PLP1 expression levels. In certain embodiments, an endogenous PLP1 gene product or a PLP1 regulatory element gene product is modified to decrease PLP1 expression levels in a cell using gene silencing.

In other embodiments, the endogenous PLP1 gene product or a PLP1 regulatory element gene product is modified through the use of a gene silencing agent that reduces or inhibits expression of PLP1 or a PLP1 regulatory element that promotes PLP1 expression, in tissue or cells of a subject in need thereof. "Expression", means the overall flow of information from a gene to produce a gene product (typically a protein, optionally post-translationally modified or a functional/structural RNA).

In some embodiments, the agent can include an RNAi construct that inhibits or reduces expression of the PLP1 expression in a cell. RNAi constructs comprise double stranded RNA that can specifically block expression of a target gene. "RNA interference" or "RNAi" is a term initially applied to a phenomenon observed in plants and worms where double-stranded RNA (dsRNA) blocks gene expression in a specific and post-transcriptional manner.

As used herein, the term "dsRNA" refers to siRNA molecules or other RNA molecules including a double stranded feature and able to be processed to siRNA in cells, such as hairpin RNA moieties (shRNA) and micro-RNA (miRNA).

The term "loss-of-function," as it refers to genes inhibited by the subject RNAi method, refers to a diminishment in the level of expression of a gene when compared to the level in the absence of RNAi constructs.

As used herein, the phrase "mediates RNAi" refers to (indicates) the ability to distinguish which RNAs are to be degraded by the RNAi process, e.g., degradation occurs in a sequence-specific manner rather than by a sequence-independent dsRNA response, e.g., a PKR response.

As used herein, the term "RNAi construct" is a generic term used throughout the specification to include small interfering RNAs (siRNAs), hairpin RNAs, and other RNA species (such as miRNA), which can be cleaved in vivo to form siRNAs and/or miRNAs. RNAi constructs herein also include expression vectors (also referred to as RNAi expression vectors) capable of giving rise to transcripts which form dsRNAs or hairpin RNAs in cells, and/or transcripts which can produce siRNAs in vivo.

"RNAi expression vector" (also referred to herein as a "dsRNA-encoding plasmid") refers to replicable nucleic acid constructs used to express (transcribe) RNA which produces siRNA/shRNA/miRNA moieties in the cell in which the construct is expressed. Such vectors include a transcriptional unit comprising an assembly of (1) genetic element(s) having a regulatory role in gene expression, for example, promoters, operators, or enhancers, operatively linked to (2) a "coding" sequence which is transcribed to produce a double-stranded RNA (two RNA moieties that anneal in the cell to form an siRNA, or a single hairpin RNA which can be processed to an siRNA, or an miRNA), and (3) appropriate transcription initiation and termination sequences.

The choice of promoter and other regulatory elements generally varies according to the intended host cell, such as an OPC. In general, expression vectors of utility in recombinant DNA techniques are often in the form of "plasmids" which refer to circular double stranded DNA loops, which, in their vector form are not bound to the chromosome. In the present specification, "plasmid" and "vector" are used interchangeably as the plasmid is the most commonly used form of vector. However, the application describes other forms of expression vectors that serve equivalent functions and which become known in the art subsequently hereto.

The RNAi constructs contain a nucleotide sequence that hybridizes under physiologic conditions of the cell to the nucleotide sequence of at least a portion of the mRNA transcript for the gene to be inhibited (i.e., the "target" gene). The double-stranded RNA need only be sufficiently similar to natural RNA that it has the ability to mediate RNAi. Thus, embodiments tolerate sequence variations that might be expected due to genetic mutation, strain polymorphism or evolutionary divergence. The number of tolerated nucleotide mismatches between the target sequence and the RNAi construct sequence is no more than 1 in 5 basepairs, or 1 in 10 basepairs, or 1 in 20 basepairs, or 1 in 50 basepairs. Mismatches in the center of the siRNA duplex are most critical and may essentially abolish cleavage of the target RNA. In contrast, nucleotides at the 3' end of the siRNA strand that is complementary to the target RNA do not significantly contribute to specificity of the target recognition.

Sequence identity may be optimized by sequence comparison and alignment algorithms known in the art and calculating the percent difference between the nucleotide sequences by, for example, the Smith-Waterman algorithm as implemented in the BESTFIT software program using default parameters (e.g., University of Wisconsin Genetic Computing Group). Greater than 90% sequence identity, or even 100% sequence identity, between the inhibitory RNA and the portion of the target gene is preferred. Alternatively, the duplex region of the RNA may be defined functionally as a nucleotide sequence that is capable of hybridizing with a portion of the target gene transcript.

Production of RNAi constructs can be carried out by chemical synthetic methods or by recombinant nucleic acid techniques. Endogenous RNA polymerase of the treated cell may mediate transcription in vivo, or cloned RNA polymerase can be used for transcription in vitro. The RNAi constructs may include modifications to either the phosphate-sugar backbone or the nucleoside, e.g., to reduce susceptibility to cellular nucleases, improve bioavailability, improve formulation characteristics, and/or change other pharmacokinetic properties. For example, the phosphodiester linkages of natural RNA may be modified to include at least one of a nitrogen or sulfur heteroatom. Modifications in RNA structure may be tailored to allow specific genetic inhibition while avoiding a general response to dsRNA. Likewise, bases may be modified to block the activity of adenosine deaminase. The RNAi construct may be produced enzymatically or by partial/total organic synthesis, a modified ribonucleotide can be introduced by in vitro enzymatic or organic synthesis.

Methods of chemically modifying RNA molecules can be adapted for modifying RNAi constructs (see for example, *Nucleic Acids Res,* 25:776-780; *J Mol Recog* 7:89-98; *Nucleic Acids Res* 23:2661-2668; *Antisense Nucleic Acid Drug Dev* 7:55-61). Merely to illustrate, the backbone of an RNAi construct can be modified with phosphorothioates, phosphoramidate, phosphodithioates, chimeric methylphosphonate-phosphodiesters, peptide nucleic acids, 5-propynyl-pyrimidine containing oligomers or sugar modifications (e.g., 2'-substituted ribonucleosides, a-configuration).

The double-stranded structure may be formed by a single self-complementary RNA strand or two complementary RNA strands. RNA duplex formation may be initiated either inside or outside the cell. The RNA may be introduced in an amount, which allows delivery of at least one copy per cell. Higher doses (e.g., at least 5, 10, 100, 500 or 1000 copies per cell) of double-stranded material may yield more effective inhibition, while lower doses may also be useful for specific applications. Inhibition is sequence-specific in that nucleotide sequences corresponding to the duplex region of the RNA are targeted for genetic inhibition.

In certain embodiments, the subject RNAi constructs are "small interfering RNAs" or "siRNAs." These nucleic acids are around 19-30 nucleotides in length, and even more preferably 21-23 nucleotides in length, e.g., corresponding in length to the fragments generated by nuclease "dicing" of longer double-stranded RNAs. The siRNAs are understood to recruit nuclease complexes and guide the complexes to the target mRNA by pairing to the specific sequences. As a result, the target mRNA is degraded by the nucleases in the protein complex. In a particular embodiment, the 21-23 nucleotides siRNA molecules comprise a 3' hydroxyl group.

The siRNA molecules described herein can be obtained using a number of techniques known to those of skill in the art. For example, the siRNA can be chemically synthesized or recombinantly produced using methods known in the art. For example, short sense and antisense RNA oligomers can be synthesized and annealed to form double-stranded RNA structures with 2-nucleotide overhangs at each end (*Proc Natl Acad Sci USA,* 98:9742-9747; *EMBO J,* 20:6877-88). These double-stranded siRNA structures can then be directly introduced to cells, either by passive uptake or a delivery system of choice, such as described below.

In certain embodiments, the siRNA constructs can be generated by processing of longer double-stranded RNAs, for example, in the presence of the enzyme dicer. In one embodiment, the *Drosophila* in vitro system is used. In this embodiment, dsRNA is combined with a soluble extract derived from *Drosophila* embryo, thereby producing a combination. The combination is maintained under conditions in which the dsRNA is processed to RNA molecules of about 21 to about 23 nucleotides.

The siRNA molecules can be purified using a number of techniques known to those of skill in the art. For example, gel electrophoresis can be used to purify siRNAs. Alternatively, non-denaturing methods, such as non-denaturing column chromatography, can be used to purify the siRNA. In addition, chromatography (e.g., size exclusion chromatography), glycerol gradient centrifugation, affinity purification with antibody can be used to purify siRNAs.

In certain embodiments, the RNAi construct is in the form of a hairpin structure (named as hairpin RNA). The hairpin RNAs can be synthesized exogenously or can be formed by transcribing from RNA polymerase III promoters in vivo. Examples of making and using such hairpin RNAs for gene silencing in mammalian cells are described in, for example, *Genes Dev,* 2002, 16:948-58; Nature, 2002, 418:38-9; RNA, 2002, 8:842-50; and *Proc Natl Acad Sci,* 2002, 99:6047-52. Preferably, such hairpin RNAs are engineered in cells or in an animal to ensure continuous and stable suppression of a desired gene. It is known in the art that siRNAs can be produced by processing a hairpin RNA in the cell.

In certain embodiments, the RNAi construct is in the form of a micro-RNA or miRNA. miRNAs are non-coding single-stranded RNAs transcribed from either their own genes or from introns by RNA polymerase II. After transcription, the primary miRNA is first processed into pre-miRNA with a stem-loop structure (about 70 nucleotides) and then into a functional miRNA (21-23 nucleotides). Like siRNA and shRNA, miRNA also uses the RISC for mRNA degradation and posttranscription gene silencing, and has the potential to target any mRNA of interest. In contrast to siRNA which has perfect complementarity to the target mRNA, miRNA binds imperfectly to the target mRNA. This partial complementary binding allows each miRNA to potentially interact with many similar sets of target mRNA. In addition to mRNA degradation, miRNA may cause translational repression without endonucleolytic cleavage. Thus miRNA-targeted genes may be regulated translationally without affecting the mRNA level of the target. A potential advantage of miRNA over siRNA is that one single miRNA transcript can be processed into multiple siRNAs.

In yet other embodiments, a plasmid is used to deliver the double-stranded RNA, e.g., as a transcriptional product. In such embodiments, the plasmid is designed to include a "coding sequence" for each of the sense and antisense strands of the RNAi construct. The coding sequences can be the same sequence, e.g., flanked by inverted promoters, or can be two separate sequences each under transcriptional control of separate promoters. After the coding sequence is transcribed, the complementary RNA transcripts base-pair to form the double-stranded RNA.

PCT application WO01/77350 describes an example of a vector for bi-directional transcription of a transgene to yield both sense and antisense RNA transcripts of the same transgene in a eukaryotic cell. Accordingly, certain embodiments provide a recombinant vector having the following unique characteristics: it comprises a viral replicon having two overlapping transcription units arranged in an opposing orientation and flanking a transgene for an RNAi construct of interest, wherein the two overlapping transcription units yield both sense and antisense RNA transcripts from the same transgene fragment in a host cell.

In some embodiments, a lentiviral vector can be used for the long-term expression of a siRNA, such as a short-hairpin RNA (shRNA), to knockdown expression of the PLP1 gene. Although there have been some safety concerns about the use of lentiviral vectors for gene therapy, self-inactivating lentiviral vectors are considered good candidates for gene therapy as they readily transfect mammalian cells.

By way of example, short-hairpin RNA (shRNA) down regulation of the PLP1 expression can be created using OligoEngene software (OligoEngine, Seattle, Wash.) to identify sequences as targets of siRNA. The oligo sequences can be annealed and ligated into linearized pSUPER RNAi vector (OligoEngine, Seattle, Wash.) and transformed in *E coli* strain DH5a cells. After positive clones are selected, plasmid can be transfected into 293T cells by calcium precipitation. The viral supernatant collected containing shRNA can then be used to infect mammalian cells in order to down regulate the PLP1 gene product thereby decreasing PLP1 expression level in the cells.

Carriers developed for DNA can also be used for RNAi partly due to their similar physicochemical properties. These carriers can be broadly divided into two categories, i.e., viral and non-viral. See a recent review on viral delivery systems for RNAi (Castanotto and Rossi, *The promises and pitfalls of RNA-interference-based therapeutics. Nature* 457(7228): 426-33, 2009, incorporated herein by reference). Non-viral RNAi vectors typically involve complexing RNAi constructs with a positively charged vector (e.g., cationic cell penetrating peptides, cationic polymers and dendrimers, and cationic lipids); conjugating RNAi constructs with small molecules (e.g., cholesterol, bile acids, and lipids), polymers, antibodies, and RNAs; and encapsulating RNAi construct in nanoparticulate formulations. Modification of the RNA backbone improves the stability of siRNA without affecting its RNAi efficiency. The selection of RNAi delivery systems can depend on the properties of siRNA, the type of target cells, and the delivery routes for in vivo application.

In certain embodiments, the RNAi construct is delivered through cationic cell penetrating peptides (CPP). CPP has been used for intracellular delivery of macromolecules including proteins (e.g., antibodies), peptides, antisense oligonucleotides, and plasmid DNA. In addition to utilizing the traditional endocytotic pathways, CPP-mediated RNAi delivery systems form either non-covalent complexes (non-covalent CPP-siRNA) through electrostatic interactions, or form covalent cross-links through disulfide bonds (covalent CPP-siRNA), and may enter cells directly by crossing the cell membrane.

In certain embodiments, the RNAi construct is delivered through polymeric and dendrimeric carriers. Linear or branched cationic polymers are well established efficient transfection agents for DNA and RNA. These positively charged polymers work by forming polyplexes with the negatively charged phosphates of nucleic acids through electrostatic interactions. Other suitable polymeric carriers of siRNA include micelles, nanoplexes, nanocapsules, and nanogels. The properties of polyplexes (e.g., size, surface charge, and structure) are dependent on the ratio of the positive charges of cationic polymers to the number of phosphate groups of siRNA. A variety of polymers such as poly-1-lysine, polyethyleneimine (PEI), poly-d,l-lactide-co-glycolide (PLGA), poly(alkylcyanoacrylate), chitosan, and gelatin are suitable. Others include dendrimers with positively charged surface groups, the precise core-shell nanostructures of which enable drug loading by interior encapsulation, surface adsorption, or chemical conjugation. Exemplary dendrimers include cationic polyamidoamine (PAMAM, amino-terminated surface), with optional pegylation to improve the surface features of dendrimers; poly (propylene imine) (PPI), and cyclodextrin-containing cationic polymers and dendrimers.

In certain embodiments, the RNAi construct is delivered as bioconjugates. The RNAi construct can be conjugated with a variety of molecules including small molecules (e.g., cholesterol, bile acids, and lipids), peptides (such as cationic cell-penetrating peptides), polymers (such as the endosomolytic agent amphipathic poly(vinyl ether) PBAVE), proteins (e.g., antibody), and aptamers (e.g., RNA aptamers) to improve stability, cellular internalization, or cell-specific active targeting delivery.

In certain embodiments, the RNAi construct is delivered with lipid-based carriers, including liposomes, micelles, microemulsions, and solid lipid nanoparticles. Liposomes are popular siRNA carriers due to their relative simplicity and well-known pharmaceutical properties. Several liposomal carriers of cancer drugs have shown good safety records in humans, and one (Doxil) has received FDA approval for human use. Lipid-based carriers have also been successfully used to deliver siRNA (e.g., intravenous or Intraperitoneal injection of siRNA loaded in liposomes of cationic and fusogenic lipids) to target sites in the endothelium, RES organs (e.g., liver), and solid tumors.

In certain embodiments, the RNAi construct is delivered with the use of molecular Trojan horses (such as a Trojan horse liposome (THL) formulation) and avidin-biotin technology. Molecular Trojan horses may also be formulated as Trojan horse liposomes to deliver shRNA-expressing plasmid DNA to brain in vivo. Similar to the delivery of non-viral gene therapies, plasmid DNA encoding for short hairpin RNA (shRNA) may also be delivered to brain following intravenous administration with pegylated immunoliposomes (PILs). For example, the plasmid DNA may be encapsulated in a liposome (such as a 100 nm liposome), which is pegylated, and conjugated with receptor specific targeting monoclonal antibodies (MAb). Using this delivery means, weekly intravenous RNAi with PILs enables a 90% knockdown of the human epidermal growth factor receptor (EGFR), which results in a 90% increase in survival time in mice with intra-cranial brain cancer. The same technology can also be used to deliver other RNAi constructs including siRNA and miRNA to the brain. For example, the siRNA may be mono-biotinylated in parallel with the production of a conjugate of the targeting MAb and streptavidin.

A molecular Trojan horse (MTH) is an endogenous peptide or peptidomimetic monoclonal antibody (MAb) that undergoes receptor-mediated transport (RMT) across the blood brain barrier (BBB). A peptidomimetic MAb binds to an exofacial epitope on the BBB receptor, which allows the MAb to undergo RMT across the BBB without interference of BBB transport of the endogenous ligand. The peptidomimetic MAb may carry across the BBB any attached drug or even plasmid DNA via the BBB RMT system.

A panel of species-specific MAb molecular Trojan horses has been developed for brain drug delivery. For example, for drug delivery in mice, the rat 8D3 MAb to the mouse TfR is used. This MTH is not active in rats. For brain drug delivery in rats, the murine OX26 MAb to the rat TfR is used, and this MTH is not active in mice or other species. For brain drug delivery to Old World primates such as the Rhesus monkey, the murine 83-14 MAb to the human insulin receptor (HIR) is used. The HIRMAb is not active in New World primates such as squirrel monkey. Genetically engineered forms of the HIRMAb, both a chimeric HIRMAb and a humanized HIRMAb, have been produced to enable brain drug delivery in humans.

The delivery of protein therapeutics to brain following intravenous administration with molecular Trojan horses has been reduced to pharmacologic practice in vivo for a number of experimental systems. See Pardridge (*Adv Drug Deliv Rev.* 59(2-3):141-152, 2007). These studies of recombinant protein delivery to brain in vivo with intravenous administration demonstrate that BBB MTHs can deliver large molecule therapeutics into brain in vivo.

For non-viral plasmid DNA delivery in vivo, a Trojan horse liposome (THL) formulation was developed, whereby the MTH was associated with non-viral plasmid DNA in a way that would be stable in vivo. Specifically, a single plasmid DNA molecule is encapsulated in the interior of a ~100 nm liposome, the surface of which is conjugated with several thousand strands of a polymer, such as 2000 Da polyethylene glycol (PEG). The tips of 1-2% of the PEG strands are conjugated with a receptor (R)-specific MAb that acts as the MTH. This results in the formulation of a pegylated immunoliposome (PIL) encapsulating the plasmid DNA. The targeting MAb binds to the BBB receptor to trigger RMT from blood to the brain interstitial fluid. Subsequently, the targeting MAb binds the same receptor on brain cells to trigger receptor-mediated endocytosis into brain intracellular spaces. In the case of the insulin receptor, which normally delivers its endogenous ligand, insulin, to the nuclear compartment, the insulin receptor delivers the plasmid DNA to the nucleus of the brain cell, which is followed by expression of the endogenous transgene. In a typical formulation, there are 30 to 80 MAb molecules conjugated to an individual liposome. Any DNA that is not fully encapsulated in the interior of the liposome can be exhaustively removed by nuclease treatment.

Using this technology, Luciferase and β-galactosidase reporter genes (and many other genes in similar manner) have been delivered to mice brain with Trojan horse liposomes, by intravenous injection into adult mice at a dose of 5 µg plasmid DNA per mouse in a volume of 0.2 mL. There was global expression of the transgene throughout the brain following an intravenous administration of this non-viral formulation. The pattern of expression parallels the expression of the neuronal transferrin receptor, which is ubiquitous in brain. The transgene is expressed in both cortical and subcortical structures, in choroid plexus, in hippocampus, the midbrain, spinal cord, and is highly expressed in the Purkinje cell layer of the cerebellum. The Trojan horse liposome technology enables "adult transgenics" within 24 hours after intravenous administration of non-viral formulations. The gene is delivered to virtually all cells of the brain. At the dose of 10 µg plasmid DNA/kg body weight, approximately 3-4 plasmid DNA molecules can be delivered to each brain cell of the adult primate brain.

In a similar study, a tyrosine hydroxylase (TH) cDNA was formulated in an expression plasmid driven by the SV40 promoter. The TH expression plasmid was encapsulated in Trojan horse liposomes that were targeted to rat brain with the murine OX26 MAb to the rat TfR. TH gene therapy with the Trojan horse liposomes resulted in a complete normalization of striatal TH enzyme activity ipsilateral to the lesion and resulted in 82% reduction in abnormal rotational behavior induced by apomorphine. See Pardridge (*Adv Drug Deliv Rev.* 59(2-3):141-152, 2007).

In certain embodiment, tissue specific promotor is used to drive and limit the expression of the transgene (e.g., the RNAi construct or ASO) in the brain. One brain specific promoter that can be used in the instant invention may have the 5'-flanking sequence (FS) of the human glial fibrillary acidic protein (GFAP) gene, to eliminate the expression of the transgene in peripheral (non-CNS) tissues. Therefore, the combined use of tissue-specific promoters and Trojan horse liposome delivery technology allows for localization of the expression in vivo of the therapeutic gene to the specific organ or tissue type such as the brain.

IV injection of RNAi constructs (encapsulated in Trojan horse liposomes targeted with the TfR Mab) has been used to deliver the expression of an RNAi construct (shRNA-encoding plasmid DNA) in the brain and achieve a 90% knockdown of target gene expression in a brain tumor. There is no measurable target gene activity in contralateral brain, and the RNAi gene therapy had no effect on the expression of a non-target gene. See Pardridge (*Adv Drug Deliv Rev.* 59(2-3):141-152, 2007). Thus in vivo therapeutic effect of RNAi was made possible by combining RNAi technology with Trojan horse liposome targeting technology.

The delivery of either antisense oligodeoxynucleotides (ASO), antisense peptide nucleic acids (PNA), or siRNA requires high affinity attachment of these agents to the molecular Trojan horse. The bond between the MTH and the nucleic acid therapeutic must be stable in vivo in the circulation. In some embodiments, such nucleic acids can be attached to targeting ligands via a polycationic bridge, such as polylysine or protamine. Alternatively, in other embodiments, such nucleic acid therapeutics may be attached to targeting ligands with the use of avidin-biotin technology.

The bond between avidin or streptavidin and biotin is extremely tight, and is not disrupted by serum proteins. A conjugate of the targeting MAb and either avidin or streptavidin (SA) can be formulated in one vial. In a second vial, the mono-biotinylated antisense agent (ASO) or RNAi/siRNA is produced. The two vials are mixed just prior to intravenous administration. Owing to the extremely high affinity of avidin or SA binding of biotin, there is immediate formation of the conjugate between antisense agent or the siRNA, and the targeting MAb. The dissociation half-time of biotin binding to avidin or SA is 89 days, and the dissociation constant is $10^{-15}$ M. Therefore, the association between the antisense agent and the targeting MAb in vivo in the circulation remains intact for several hours after intravenous administration. The attachment of the antisense agent to the targeting MAb through an avidin-biotin linkage has no inhibitory effect on hybridization of the antisense agent with the target RNA. This was demonstrated in previous studies by both RNAse protection assays and Northern blotting.

Using this technology, ASO agents (including Phosphorothioate (PS) and peptide nucleic acid (PNA), such as mono-biotinylated PNAs) as well as RNAi constructs (such as mono-biotinylated siRNAs) have been delivered to brain using MTH.

In certain embodiments, instead of using the mono-biotinylated siRNA, a chemical conjugate of SA and the molecular Trojan horse is used. In yet another embodiment, MAb-avidin fusion proteins is used. The mono-biotinylated siRNA, and the MTH-SA or MTH-avidin conjugate, can be mixed prior to intravenous administration. The MTHs can carry the siRNA molecules across the BBB and the BCM similar to that demonstrated previously for PNA antisense agents.

In another embodiment, the gene silencing agent that reduces or inhibits expression of PLP1 or a PLP1 regulatory element that promotes PLP1 expression can include antisense oligonucleotides (ASOs). Antisense oligonucleotides are relatively short nucleic acids that are complementary (or antisense) to the coding strand (sense strand) of the mRNA encoding a particular protein. Although antisense oligonucleotides are typically RNA based, they can also be DNA based. Additionally, antisense oligonucleotides are often modified to increase their stability.

The binding of these relatively short oligonucleotides to the mRNA is believed to induce stretches of double stranded RNA that trigger degradation of the messages by endogenous RNAses. Additionally, sometimes the oligonucleotides are specifically designed to bind near the promoter of the message, and under these circumstances, the antisense oligonucleotides may additionally interfere with translation of the message. Regardless of the specific mechanism by which antisense oligonucleotides function, their administration to a cell or tissue allows the degradation of the mRNA encoding a specific protein. Accordingly, antisense oligonucleotides decrease the expression and/or activity of a particular protein (e.g., PLP1).

The oligonucleotides can be DNA or RNA or chimeric mixtures or derivatives or modified versions thereof, single-stranded or double-stranded. The oligonucleotide can be modified at the base moiety, sugar moiety, or phosphate backbone, for example, to improve stability of the molecule, hybridization, etc. The oligonucleotide may include other appended groups, such as peptides (e.g., for targeting host cell receptors), or agents facilitating transport across the cell membrane (see, e.g., *Proc Natl Acad Sci* 86:6553-6556; *Proc Natl Acad Sci* 84:648-652; PCT Publication No. WO88/09810, published Dec. 15, 1988) or the blood-brain barrier (see, e.g., PCT Publication No. WO89/10134, published Apr. 25, 1988), hybridization-triggered cleavage agents (See, e.g., *BioTechniques* 6:958-976) or intercalating agents. (See, e.g., *Pharm Res* 5:539-549). To this end, the oligonucleotide may be conjugated or coupled to another molecule.

Oligonucleotides described herein may be synthesized by standard methods known in the art, e.g., by use of an automated DNA synthesizer (such as are commercially available from Biosearch, Applied Biosystems, etc.). As examples, phosphorothioate oligonucleotides may be synthesized by the method of Stein et al. (*Nucl. Acids Res.* 16:3209), methylphosphonate oligonucleotides can be prepared by use of controlled pore glass polymer supports (*Proc Natl Acad Sci* 85:7448-7451).

The selection of an appropriate oligonucleotide can be performed by one of skill in the art. Given the nucleic acid sequence encoding a particular protein, one of skill in the art can design antisense oligonucleotides that bind to that protein, and test these oligonucleotides in an in vitro or in vivo system to confirm that they bind to and mediate the degradation of the mRNA encoding the particular protein. To design an antisense oligonucleotide that specifically binds to and mediates the degradation of a particular protein, it is important that the sequence recognized by the oligonucleotide is unique or substantially unique to that particular protein. For example, sequences that are frequently repeated across protein may not be an ideal choice for the design of an oligonucleotide that specifically recognizes and degrades a particular message. One of skill in the art can design an oligonucleotide, and compare the sequence of that oligonucleotide to nucleic acid sequences that are deposited in publicly available databases to confirm that the sequence is specific or substantially specific for a particular protein.

A number of methods have been developed for delivering antisense DNA or RNA to cells; e.g., antisense molecules can be injected directly into the tissue site, or modified antisense molecules, designed to target the desired cells (e.g., antisense linked to peptides or antibodies that specifically bind receptors or antigens expressed on the target cell surface) can be administered systematically.

However, it may be difficult to achieve intracellular concentrations of the antisense oligonucleotide sufficient to suppress translation on endogenous mRNAs in certain instances. Therefore, another approach utilizes a recombinant DNA construct in which the antisense oligonucleotide is placed under the control of a strong pol III or pol II promoter. For example, a vector can be introduced in vivo such that it is taken up by a cell and directs the transcription of an antisense RNA. Such a vector can remain episomal or become chromosomally integrated, as long as it can be transcribed to produce the desired antisense RNA. Such vectors can be constructed by recombinant DNA technology methods standard in the art. Vectors can be plasmid, viral, or others known in the art, used for replication and expression in mammalian cells.

Expression of the sequence encoding the antisense RNA can be by a promoter known in the art to act in mammalian, preferably human cells. Such promoters can be inducible or constitutive. Such promoters include but are not limited to: the SV40 early promoter region (*Nature* 290:304-310), the promoter contained in the 3' long terminal repeat of Rous sarcoma virus (Cell 22:787-797), the herpes thymidine kinase promoter (*Proc Natl Acad Sci* 78:1441-1445), the regulatory sequences of the metallothionein gene (Nature 296:39-42), etc. A type of plasmid, cosmid, YAC or viral vector can be used to prepare the recombinant DNA construct that can be introduced directly into the tissue site. Alternatively, viral vectors can be used which selectively infect the desired tissue, in which case administration may be accomplished by another route (e.g., systematically).

Cells

Thus, provided herein are genetically modified cells comprising insertions or deletion (indels) in the PLP1 gene, for example a targeted deletion of nucleotide sequences of exon 1 or 3 in PLP1, or other modification(s) that inactivates or reduces PLP1 expression. The cells preferably produces functional myelin, or is a progenitor cell of a myelin-producing cell. In certain embodiment, the cell is a zygote, an egg, a neuronal stem cell (NSC), an OPC, or an oligodendrocyte. In certain embodiments, the genetically modified cell comprises a targeted deletion of about 80 nucleotides in the 5' end of exon 3 in PLP1 inactivates PLP1 expression. Also provided are genetically modified cells in which a PLP1 regulatory element involved in PLP1 transcription or translation is modified.

The indels (insertions or deletions) are typically integrated in a targeted manner into the cell's genome using one or more nucleases. In certain embodiments, the indels are integrated into PLP1, for example for inactivation of the PLP1 gene. In certain embodiments, the indels are generated as a result of NHEJ or other repair mechanism after introduction of double stranded breaks (DSBs) by nucleases (e.g., in the PLP1 gene or a regulatory element thereof). In other embodiments, the indels integrated into an endogenous genomic locus associated with PLP1, for instance a PLP1 genetic regulatory element such as an enhancer or promoter. In any of the cells described herein, integration may be into an exon and/or an intron (e.g., Exon 1 or 3 of PLP1).

Unlike random integration and deletion, targeted integration or deletion ensures that the indel is integrated into a specified gene. The indel may be integrated anywhere in the target gene. In certain embodiments, the indel or the donor sequence is integrated at or near the nuclease cleavage site, for example, within 1-3000 (or any value therebetween) base pairs upstream or downstream of the site of cleavage, more preferably within 1-1000 base pairs (or any value therebetween) of either side of the cleavage site, or within 1 to 500 base pairs (or any value therebetween), or within 1 to 100 base pairs (or any value therebetween) of either side of the cleavage site. In certain embodiments, the integrated sequence comprising a donor transgene does not include any vector sequences (e.g., viral vector sequences).

Any cell type can be genetically modified as described herein to comprise sequence that inactivates or reduces PLP1 expression, including but not limited to cells and cell lines. Other non-limiting examples of cells as described herein include zygotes, neural stem cells (NSCs), oligodendrocyte progenitor cells (OPCs), neuron cells, and glial cells such as oligodendrocytes, astrocytes, ependymal cells, or microglia cells. Additional non-limiting examples of cells as described herein include autologous (e.g., patient-derived) or heterologous (allogenic) pluripotent, totipotent or multipotent stem cells (e.g., embryonic stem cells or the like). In certain embodiments, the cells as described herein are OPCs.

The cells as described herein are useful in treating and/or preventing myelin-related disorders in a subject with the disorder, for example, by ex vivo therapies. The nuclease-modified cells can be expanded and then reintroduced into the patient using standard techniques. See, e.g., Tebas et al. (2014) *New Eng J Med* 370(10):901. In the case of stem cells, after infusion into the subject, in vivo differentiation of these precursors into cells expressing the inactivated PLP1 also occurs. Pharmaceutical compositions comprising the cells as described herein are also provided. In addition, the cells may be cryopreserved prior to administration to a patient.

The cells and ex vivo methods as described herein provide treatment and/or prevention of myelin-related disorders in a subject and eliminate the need for continuous prophylactic pharmaceutical administration or risky therapies. As such, the invention described herein provides a safer, cost-effective and time efficient way of treating and/or preventing myelin-related disorders.

Delivery

The nucleases, polynucleotides encoding these nucleases, donor polynucleotides and compositions comprising the proteins, oligonucleotides and/or polynucleotides described herein may be delivered by any suitable means. In certain embodiments, the nucleases and/or donors are delivered in vivo. In other embodiments, the nucleases and/or donors are delivered to isolated cells (e.g., autologous or heterologous stem cells) for the provision of modified cells useful in ex vivo delivery to myelin-related disorder patients.

Methods of delivering nucleases as described herein are described, for example, in U.S. Pat. Nos. 6,453,242; 6,503,717; 6,534,261; 6,599,692; 6,607,882; 6,689,558; 6,824,978; 6,933,113; 6,979,539; 7,013,219; and 7,163,824, the disclosures of all of which are incorporated by reference herein in their entireties.

Nucleases and/or donor constructs as described herein may also be delivered using any nucleic acid delivery mechanism, including naked DNA and/or RNA (e.g., mRNA) and vectors containing sequences encoding one or more of the components. Any vector systems may be used including, but not limited to, plasmid vectors, DNA minicircles, retroviral vectors, lentiviral vectors, adenovirus vectors, poxvirus vectors; herpesvirus vectors and adeno-associated virus vectors, etc., and combinations thereof. See, also, U.S. Pat. Nos. 6,534,261; 6,607,882; 6,824,978; 6,933,113; 6,979,539; 7,013,219; and 7,163,824, and U.S. patent application Ser. No. 14/271,008, incorporated by reference herein in their entireties. Furthermore, it will be apparent that any of these systems may comprise one or more of the sequences needed for treatment. Thus, when one or more nucleases and a donor construct are introduced into the cell, the nucleases and/or donor polynucleotide may be carried on the same delivery system or on different delivery mechanisms. When multiple systems are used, each delivery mechanism may comprise a sequence encoding one or multiple nucleases and/or donor constructs (e.g., mRNA encoding one or more nucleases and/or mRNA or AAV carrying one or more donor constructs).

Suitable vectors can include delivery vectors that are non-integrating, non-immunogenic, and capable to infect both dividing and quiescent cells. In some embodiments, in vivo delivery of Cas9 nuclease and sgRNA can be mediated by an adeno-associated virus (AAV) vector. AAV vectors for in vivo delivery include AAV serotypes having the ability to penetrate the central nervous system and infect glial myelin producing cell types of the central nervous system (oligodendrocytes, OPCs, NPCs, etc) of subject. In an exemplary embodiment, AAV vectors are employed for in vivo delivery of a Cas9 nuclease (e.g., a SaCas9 or SpCas9 nuclease). In certain embodiments, the nuclease SaCas9 and a sgRNA are packaged into one AAV vector for the nuclease-mediated genetic disruption of PLP1 in cells. See further details below.

Conventional viral and non-viral based gene transfer methods can be used to introduce nucleic acids encoding nucleases and donor constructs in cells (e.g., mammalian cells) and target tissues. Non-viral vector delivery systems include DNA plasmids, DNA minicircles, naked nucleic acid, and nucleic acid complexed with a delivery vehicle such as a liposome, lipid nanoparticle (LNP), poly-lactateglycolic acid nanoparticles, poly-amine complexing agents, or poloxamer. Viral vector delivery systems include DNA and RNA viruses, which have either episomal or integrated genomes after delivery to the cell. For a review of gene therapy procedures, see Anderson, *Science* 256:808-813 (1992); Nabel & Felgner, *TIBTECH* 11:211-217 (1993); Mitani & Caskey, *TIBTECH* 11:162-166 (1993); Dillon, *TIBTECH* 11:167-175 (1993); Miller, *Nature* 357:455-460 (1992); Van Brunt, *Biotechnology* 6(10):1149-1154 (1988); Vigne, *Restorative Neurology and Neuroscience* 8:35-36 (1995); Kremer & Perricaudet, *British Medical Bulletin* 51(1):31-44 (1995); Haddada et al., in *Current Topics in Microbiology and Immunology* Doerfler and Bohm (eds.) (1995); and Yu et al., *Gene Therapy* 1:13-26 (1994).

Methods of non-viral delivery of nucleic acids include electroporation, lipofection, microinjection, biolistics, virosomes, liposomes, immunoliposomes, polycation or lipid:nucleic acid conjugates, naked DNA, naked RNA, capped RNA, artificial virions, and agent-enhanced uptake of DNA. Sonoporation using, e.g., the Sonitron 2000 system (RichMar) can also be used for delivery of nucleic acids.

Additional exemplary nucleic acid delivery systems include those provided by Amaxa Biosystems (Cologne, Germany), Maxcyte, Inc. (Rockville, Md.), BTX Molecular Delivery Systems (Holliston, Mass.) and Copernicus Therapeutics Inc, (see for example U.S. Pat. No. 6,008,336). Lipofection is described in e.g., U.S. Pat. Nos. 5,049,386; 4,946,787; and 4,897,355) and lipofection reagents are sold commercially (e.g., Transfectam™ and Lipofectin™). Cationic and neutral lipids that are suitable for efficient receptor-recognition lipofection of polynucleotides include those of Felgner, WO 91/17424, WO 91/16024. In some aspects, the nucleases are delivered as mRNAs (e.g., using electroporation) and the transgene is delivered via other modalities such as viral vectors, minicircle DNA, plasmid DNA, single-stranded DNA, linear DNA, liposomes, nanoparticles and the like.

The preparation of lipid:nucleic acid complexes, including targeted liposomes such as immunolipid complexes, is well known to one of skill in the art (see, e.g., Crystal, *Science* 270:404-410 (1995); Blaese et al., *Cancer Gene Ther.* 2:291-297 (1995); Behr et al., *Bioconjugate Chem.* 5:382-389 (1994); Remy et al., *Bioconjugate Chem.* 5:647-654 (1994); Gao et al., *Gene Therapy* 2:710-722 (1995); Ahmad et al., *Cancer Res.* 52:4817-4820 (1992); U.S. Pat. Nos. 4,186,183, 4,217,344, 4,235,871, 4,261,975, 4,485,054, 4,501,728, 4,774,085, 4,837,028, and 4,946,787).

Additional methods of delivery include the use of packaging the nucleic acids to be delivered into EnGeneIC delivery vehicles (EDVs). These EDVs are specifically delivered to target tissues using bispecific antibodies where one arm of the antibody has specificity for the target tissue and the other has specificity for the EDV. The antibody brings the EDVs to the target cell surface and then the EDV is brought into the cell by endocytosis. Once in the cell, the contents are released (see MacDiarmid et al. (2009) *Nature Biotechnology* 27(7):643).

The use of RNA or DNA viral based systems for the delivery of nucleic acids encoding engineered CRISPR/Cas systems, or encoding an RNAi construct that can produce siRNA, shRNA, or miRNA inside the target cell, take advantage of highly evolved processes for targeting a virus to specific cells in the body and trafficking the viral payload to the nucleus. Viral vectors can be administered directly to subjects (in vivo) or they can be used to treat cells in vitro and the modified cells are administered to subjects (ex vivo). Conventional viral based systems for the delivery of CRISPR/Cas systems include, but are not limited to, retroviral, lentivirus, adenoviral, adeno-associated, vaccinia and herpes simplex virus vectors for gene transfer. Integration in the host genome is possible with the retrovirus, lentivirus, and adeno-associated virus gene transfer methods, often resulting in long term expression of the inserted transgene. Additionally, high transduction efficiencies have been observed in many different cell types and target tissues.

The tropism of a retrovirus can be altered by incorporating foreign envelope proteins, expanding the potential target population of target cells. Lentiviral vectors are retroviral vectors that are able to transduce or infect non-dividing cells and typically produce high viral titers. Selection of a retroviral gene transfer system depends on the target tissue. Retroviral vectors are comprised of cis-acting long terminal repeats with packaging capacity for up to 6-10 kb of foreign sequence. The minimum cis-acting LTRs are sufficient for replication and packaging of the vectors, which are then used to integrate the therapeutic gene into the target cell to provide permanent transgene expression. Widely used retroviral vectors include those based upon murine leukemia virus (MuLV), gibbon ape leukemia virus (GaLV), Simian Immunodeficiency virus (SIV), human immunodeficiency virus (HIV), and combinations thereof (see, e.g., Buchscher et al., *J. Virol.* 66:2731-2739 (1992); Johann et al., *J. Virol.* 66:1635-1640 (1992); Sommerfelt et al., *Virol.* 176:58-59 (1990); Wilson et al., *J. Virol.* 63:2374-2378 (1989); Miller et al., *J. Virol.* 65:2220-2224 (1991); PCT/US94/05700).

Adenoviral based vectors are capable of very high transduction efficiency in many cell types and do not require cell division. With such vectors, high titer and high levels of expression have been obtained. This vector can be produced in large quantities in a relatively simple system. Adeno-associated virus ("AAV") vectors are also used to transduce cells with target nucleic acids, e.g., in the in vitro production of nucleic acids and peptides, and for in vivo and ex vivo gene therapy procedures (see, e.g., West et al., *Virology* 160:38-47 (1987); U.S. Pat. No. 4,797,368; WO 93/24641; Kotin, *Human Gene Therapy* 5:793-801 (1994); Muzyczka, *J. Clin. Invest.* 94:1351 (1994). Construction of recombinant AAV vectors are described in a number of publications, including U.S. Pat. No. 5,173,414; Tratschin et al., *Mol. Cell. Biol.* 5:3251-3260 (1985); Tratschin, et al., *Mol. Cell. Biol.* 4:2072-2081 (1984); Hermonat & Muzyczka, *PNAS* 81:6466-6470 (1984); and Samulski et al., *J. Virol.* 63:03822-3828 (1989). Any AAV serotype can be used, including AAV1, AAV3, AAV4, AAV5, AAV6 and AAV8, AAV 8.2, AAV9, and AAV rh10 and pseudotyped AAV such as AAV2/8, AAV2/5 and AAV2/6. Additional adenoviral based vectors include AAV variants that efficiently and widely transduce the mammalian central nervous system (CNS) after intravenous injection such as AAV-PHP.B vectors described in Deverman et al. (2016) *Nature Biotechnology* 204-209.

At least six viral vector approaches are currently available for gene transfer in clinical trials, which utilize approaches that involve complementation of defective vectors by genes inserted into helper cell lines to generate the transducing agent.

pLASN and MFG-S are examples of retroviral vectors that have been used in clinical trials (Dunbar et al., *Blood* 85:3048-305 (1995); Kohn et al., *Nat. Med.* 1:1017-102 (1995); Malech et al., *PNAS* 94:22 12133-12138 (1997)). PA317/pLASN was the first therapeutic vector used in a gene therapy trial. (Blaese et al., *Science* 270:475-480 (1995)). Transduction efficiencies of 50% or greater have been observed for MFG-S packaged vectors. (Ellem et al., *Immunol Immunother.* 44(1):10-20 (1997); Dranoff et al., *Hum. Gene Ther.* 1:111-2 (1997).

Recombinant adeno-associated virus vectors (rAAV) are a promising alternative gene delivery systems based on the defective and nonpathogenic parvovirus adeno-associated type 2 virus. All vectors are derived from a plasmid that retains only the AAV 145 base pair (bp) inverted terminal repeats flanking the transgene expression cassette. Efficient gene transfer and stable transgene delivery due to integration into the genomes of the transduced cell are key features for this vector system. (Wagner et al., *Lancet* 351:9117 1702-3 (1998), Kearns et al., *Gene Ther.* 9:748-55 (1996)). Other AAV serotypes, including AAV1, AAV3, AAV4, AAV5, AAV6, AAV8, AAV9 and AAVrh10, and all variants thereof including engineered mutants selected from libraries, can also be used in accordance with the present invention.

Replication-deficient recombinant adenoviral vectors (Ad) can be produced at high titer and readily infect a number of different cell types. Most adenovirus vectors are engineered such that a transgene replaces the Ad E1a, E1b, and/or E3 genes; subsequently the replication defective vector is propagated in human 293 cells that supply deleted gene function in trans. Ad vectors can transduce multiple types of tissues in vivo, including non-dividing, differentiated cells such as those found in liver, kidney and muscle. Conventional Ad vectors have a large carrying capacity. An example of the use of an Ad vector in a clinical trial involved polynucleotide therapy for anti-tumor immunization with intramuscular injection (Sterman et al., *Hum. Gene Ther.* 7:1083-9 (1998)). Additional examples of the use of adenovirus vectors for gene transfer in clinical trials include Rosenecker et al., *Infection* 24:1 5-10 (1996); Sterman et al., *Hum. Gene Ther.* 9:7 1083-1089 (1998); Welsh et al., *Hum. Gene Ther.* 2:205-18 (1995); Alvarez et al., *Hum. Gene Ther.* 5:597-613 (1997); Topf et al., *Gene Ther.* 5:507-513 (1998); Sterman et al., *Hum. Gene Ther.* 7:1083-1089 (1998).

Packaging cells are used to form virus particles that are capable of infecting a host cell. Such cells include 293 cells, which package adenovirus, and ψ2 cells or PA317 cells, which package retrovirus. Viral vectors used in gene therapy are usually generated by a producer cell line that packages a nucleic acid vector into a viral particle. The vectors typically contain the minimal viral sequences required for packaging and subsequent integration into a host (if applicable), other viral sequences being replaced by an expression cassette encoding the protein to be expressed. The missing viral functions are supplied in trans by the packaging cell line. For example, AAV vectors used in gene therapy typically only possess inverted terminal repeat (ITR) sequences from the AAV genome which are required for packaging and integration into the host genome. Viral DNA is packaged in a cell line, which contains a helper plasmid encoding the other AAV genes, namely rep and cap, but lacking ITR sequences. The cell line is also infected with adenovirus as a helper. The helper virus promotes replication of the AAV vector and expression of AAV genes from the helper plasmid. The helper plasmid is not packaged in significant amounts due to a lack of ITR sequences. Contamination with adenovirus can be reduced by, e.g., heat treatment to which adenovirus is more sensitive than AAV.

In many gene therapy applications, it is desirable that the gene therapy vector be delivered with a high degree of specificity to a particular tissue type. Accordingly, a viral vector can be modified to have specificity for a given cell type by expressing a ligand as a fusion protein with a viral coat protein on the outer surface of the virus. The ligand is chosen to have affinity for a receptor known to be present on the cell type of interest. For example, Han et al., *Proc. Natl. Acad. Sci. USA* 92:9747-9751 (1995), reported that Moloney murine leukemia virus can be modified to express human heregulin fused to gp70, and the recombinant virus infects certain human breast cancer cells expressing human epidermal growth factor receptor. This principle can be extended to other virus-target cell pairs, in which the target cell expresses a receptor and the virus expresses a fusion protein comprising a ligand for the cell-surface receptor. For example, filamentous phage can be engineered to display antibody fragments (e.g., FAB or Fv) having specific binding affinity for virtually any chosen cellular receptor. Although the above description applies primarily to viral vectors, the same principles can be applied to nonviral vectors. Such vectors can be engineered to contain specific uptake sequences which favor uptake by specific target cells.

Gene therapy vectors can be delivered in vivo by administration to an individual subject, typically by systemic administration (e.g., intravenous, intraperitoneal, intramuscular, subdermal, sublingual or intracranial infusion) topical application, as described below, or via pulmonary inhalation. Alternatively, vectors can be delivered to cells ex vivo, such as cells explanted from an individual patient (e.g., OPCs) or universal donor neural stem cells, followed by reimplantation of the cells into a patient, usually after selection for cells which have incorporated the vector.

Vectors (e.g., retroviruses, adenoviruses, AAVs, liposomes, etc.) containing nucleases and/or donor constructs can also be administered directly to an organism for transduction of cells in vivo. Alternatively, naked DNA can be administered. Administration is by any of the routes normally used for introducing a molecule into ultimate contact with glial cells including, but not limited to, injection, infusion, topical application, inhalation and electroporation. Suitable methods of administering such nucleic acids are available and well known to those of skill in the art, and, although more than one route can be used to administer a particular composition, a particular route can often provide a more immediate and more effective reaction than another route.

Vectors suitable for introduction of polynucleotides described herein include non-integrating lentivirus vectors (IDLV). See, for example, Ory et al. (1996) *Proc. Natl. Acad. Sci. USA* 93:11382-11388; Dull et al. (1998) *J. Virol.* 72:8463-8471; Zuffery et al. (1998) *J. Viro.* 72:9873-9880; Follenzi et al. (2000) *Nature Genetics* 25:217-222; U.S. Patent Publication No 2009/054985.

Pharmaceutically acceptable carriers are determined in part by the particular composition being administered, as well as by the particular method used to administer the composition. Accordingly, there is a wide variety of suitable formulations of pharmaceutical compositions available, as described below (see, e.g., *Remington's Pharmaceutical Sciences,* 17th ed., 1989).

It will be apparent that the nuclease-encoding sequences and donor constructs can be delivered using the same or different systems. For example, a donor polynucleotide can be carried by an AAV, while the one or more nucleases can be carried by mRNA. Furthermore, the different systems can be administered by the same or different routes (intramuscular injection, tail vein injection, other intravenous injection, intraperitoneal administration and/or intramuscular injection. Multiple vectors can be delivered simultaneously or in any sequential order.

Formulations for both ex vivo and in vivo administrations include suspensions in liquid or emulsified liquids. The active ingredients often are mixed with excipients which are pharmaceutically acceptable and compatible with the active ingredient. Suitable excipients include, for example, water, saline, dextrose, glycerol, ethanol or the like, and combinations thereof. In addition, the composition may contain minor amounts of auxiliary substances, such as, wetting or emulsifying agents, pH buffering agents, stabilizing agents or other reagents that enhance the effectiveness of the pharmaceutical composition.

CRISPR/Cas Mediated Gene Silencing Delivered by AAV

In certain embodiments, the method of the invention can be carried out by delivering the CRISPR/Cas system, including a guide RNA (sgRNA) specifically targeting the PLP1 gene or regulatory element thereof, or a portion thereof.

In one embodiment, this system may employ 2 AAV vectors, with an optional $3^{rd}$ AAV vector: one encoding Cas9 or a functional ortholog thereof, one containing the guide RNA sequence for targeted cleavage of the PLP1 gene or regulatory elements, and optionally another one containing a donor cDNA sequence of the mutated PLP1 gene (such as a PLP1 point mutation) to be inserted at the cleavage site in order to repair or replace the defective PLP1 gene. The donor to Cas9 construct administration ratios can range anywhere from 1:1 to 5:1.

In another embodiment, this system can employ 2 AAV vectors: one encoding a Cas9 ortholog less than 3.5 kb in length and will have the guide RNA encoded in cis, and one vector containing the donor cDNA sequence of the mutated PLP1 gene to be inserted at the cleavage site. For target greater than 4.8 kb, this donor can contain either the 3' cDNA portion of the gene up to 4.8 kb allowing correction upstream of the majority of the mutated gene, or the 5' promoter and upstream cDNA portion of the gene, which will then splice to the correct downstream sequence.

In a further embodiment, this system will employ 2 AAV vectors: one encoding a Cas9 or a functional ortholog, and one containing a guide RNA sequence specific for cleavage of a target gene.

In yet another embodiment, this system will employ one AAV vector, the vector comprising a nucleic acid encoding a functional Type II CRISPR-Cas9 and a guide RNA specific for cleavage of a target gene (e.g., PLP1).

In one embodiment, the method comprises providing one or more AAV vectors (typically 1, 2 or 3 AAV vectors) comprising elements of a CRISPR system, to bind to the target gene to effect cleavage of said target gene/polynucleotide, thereby modifying the target gene, such as disrupting the target gene or correcting or replacing all or a part of the target gene with a donor nucleic acid. Elements of said CRISPR system include a CRISPR enzyme, which can be complexed with a guide RNA sequence, said guide RNA which can be hybridized to a target sequence within said target gene.

Cleavage at the target gene can involve cleaving one or two strands by the CRISPR enzyme. In some embodiments, a method includes correcting or replacing the cleaved target gene by introduction of a donor nucleic acid, which donor nucleic acid encodes a protein that corrects for the mutated or defective target gene.

A Cas gene as described herein includes, but is not limited to, Cas3 or Cas9. The enzyme may be a Cas9 homolog or ortholog. Cas9 orthologs may include Cas9 from *Streptococcus pyogenes, Neisseria meningitidis, Streptococcus thermophilus, Streptococcus pneumnoniae, Campylobacter coli, Campylobacter jejuni, Streptococcus mutans, Pasteurella multocida, Bifidobacterium longum, Bacillus smithii, Treponema denticola, mycoplasma canis* and *Enterococcus faecalis*. A Cas9 may include mutated Cas9 derived from these organisms.

Exemplary AAV vectors include capsid sequence of any of AAV 1, AAV2, AAV3, AAV4, AAV5, AAV6, AAV7, AAV 8, AAV9, AAV10, AAV 11, RhlO, Rh74 or AAV-2i8, or a capsid variant of AAV 1, AAV2, AAV3, AAV4, AAV5, AAV6, AAV7, AAV8, AAV9, AAV10, AAV11, RhlO, Rh74 or AAV-2i8. Recombinant AAV vectors of the invention also include AAV1, AAV2, AAV3, AAV4, AAV5, AAV6, AAV7, AAV8, AAV9, AAV10, AAV11, RhlO, Rh74 or AAV-2i8, and variants thereof.

Particular capsid variants include capsid variants of AAV 1, AAV2, AAV3, AAV4, AAV5, AAV6, AAV7, AAV8, AAV9, AAV 10, AAV11, RhlO, Rh74 or AAV-2i8, such as a capsid sequence with an amino acid substitution, deletion or insertion/addition.

AAV vectors can include additional elements that function in cis or in trans. In particular embodiments, an AAV vector that includes a vector genome also has: one or more inverted terminal repeat (ITR) sequences that flank the 5' or 3' terminus of the donor sequence; an expression control element that drives transcription (e.g., a promoter or enhancer) of the donor sequence, such as a constitutive or regulatable control element, or tissue-specific expression control element; an intron sequence, a staffer or filler polynucleotide sequence; and/or a poly-Adenine sequence located 3' of the donor sequence.

Typically, expression control elements are nucleic acid sequence(s) that influence expression of an operably linked polynucleotide. Control elements, including expression control elements as set forth herein such as promoters and enhancers, present within a vector are included to facilitate proper nucleic acid transcription and translation (e.g., a promoter, enhancer, splicing signal for introns, maintenance of the correct reading frame of the gene to permit in-frame translation of mRNA and, stop codons etc.), and AAV packaging. Such elements typically act in cis, referred to as a "cis acting" element, but may also act in trans.

Expression control can be effected at the level of transcription, translation, splicing, message stability, etc. Typically, an expression control element that modulates transcription is juxtaposed near the 5' end (i.e., "upstream") of a transcribed nucleic acid. Expression control elements can also be located at the 3' end (i.e., "downstream") of the transcribed sequence or within the transcript (e.g., in an intron). Expression control elements can be located adjacent to or at a distance away from the transcribed sequence. Typically, owing to the polynucleotide length limitations of certain vectors, such as AAV vectors, such expression control elements will be within 1 to 1000 nucleotides from the transcribed nucleic acid.

A "promoter" as used herein is operatively linked to an adjacent sequence, and increases an amount expressed from a nucleic acid as compared to an amount expressed when no promoter exists.

An "enhancer" as used herein is located adjacent to the nucleic acid, typically located upstream of a promoter element but also function and can be located downstream of or within a DNA sequence (e.g., a donor nucleic acid). An enhancer element can be located 100 base pairs, 200 base pairs, or 300 or more base pairs upstream or downstream of a nucleic acid. Enhancer elements also typically increase expression of a nucleic acid.

Expression control elements include ubiquitous or promiscuous promoters/enhancers which are capable of driving expression of a polynucleotide in many different cell types. Such elements include, but are not limited to the cytomegalovirus (CMV) immediate early promoter/enhancer sequences, the Rous sarcoma virus (RSV) promoter/enhancer sequences and the other viral promoters/enhancers active in a variety of mammalian cell types, or synthetic elements that are not present in nature (see, e.g., Boshart et al, Cell, 41:521-530 (1985)), the SV40 promoter, the dihydrofolate reductase (DHFR) promoter, the cytoplasmic β-actin promoter and the phosphoglycerol kinase (PGK) promoter.

Expression control elements may also include those active in a particular tissue or cell type, referred to herein as a "tissue-specific expression control elements/promoters." Tissue-specific expression control elements are typically active in specific cell or tissue (e.g., eye, retina, central nervous system, spinal cord, eye, retina, etc.). In certain embodiments, the tissue-specific expression control elements are active in the CNS, such as neuronal stem cells, OPCs, oligodendrocytes, etc. In certain embodiments, the issue-specific expression control elements are active in the zygote or an egg.

Expression control elements are typically active in these cells, tissues or organs because they are recognized by transcriptional activator proteins, or other regulators of transcription, that are unique to a specific cell, tissue or organ type.

Expression control elements also can confer expression in a manner that is regulatable, that is, a signal or stimuli increases or decreases expression of the operably linked nucleic acid. A regulatable element that increases expression of the operably linked nucleic acid in response to a signal or stimuli is also referred to as an "inducible element" (i.e., is induced by a signal). Particular examples include, but are not limited to, a hormone (e.g., steroid) inducible promoter. A regulatable element that decreases expression of the operably linked nucleic acid in response to a signal or stimuli is referred to as a "repressible element" (i.e., the signal decreases expression such that when the signal, is removed or absent, expression is increased). Typically, the amount of increase or decrease conferred by such elements is proportional to the amount of signal or stimuli present; the greater the amount of signal or stimuli, the greater the increase or decrease in expression.

Expression control elements also include the native elements(s). A native control element (e.g., promoter) may be used when it is desired that expression of the nucleic acid may mimic the native expression. A native element may be used when expression of the nucleic acid is to be regulated temporally or developmentally, or in a tissue-specific manner, or in response to specific transcriptional stimuli. Other native expression control elements, such as introns, polyadenylation sites or Kozak consensus sequences may also be used.

AAV vectors may also include filler or staffer polynucleotide sequence. For example, where a donor nucleic acid has a length less than about 4.7 kb, a filler or staffer polynucleotide sequence has a length that, when combined with donor nucleic acid, the total combined length is between about 3.0-5.5 kb, or between about 4.0-5.0 kb, or between about 4.3-4.8 kb.

Filler or staffer polynucleotide sequences can be located in the vector sequence at any desired position such that it does not prevent a function or activity of the vector. In one aspect, a filler or staffer polynucleotide sequence is positioned between a 5' and/or 3' ITR (e.g., an ITR of AAV1, AAV2, AAV3, AAV4, AAV5, AAV6, AAV7, AAV8, AAV9, AAV10, AAV11, RhlO, Rh74 or AAV-2i8, and variants thereof) that flanks the respective 5' and/or 3' termini of a donor nucleic acid sequence.

Typically, a filler or staffer polynucleotide sequence is inert or innocuous and has no function or activity. In various particular aspects, a filler or staffer polynucleotide sequence is not a bacterial polynucleotide sequence, a filler or staffer polynucleotide sequence is not a sequence that encodes a protein or peptide, a filler or staffer polynucleotide sequence is a sequence distinct from any of: the donor sequence, an AAV inverted terminal repeat (ITR) sequence, an expression control element, or a poly-adenylation (poly-A) signal sequence. In various particular aspects, a filler or staffer polynucleotide sequence is an intron sequence that is related to or unrelated to the donor sequence.

An intron can also function as a filler or staffer polynucleotide sequence in order to achieve a length for AAV vector packaging into a virus particle. Introns and intron fragments (e.g. portion of intron I of FIX) that function as a filler or staffer polynucleotide sequence also can enhance expression. Inclusion of an intron element may enhance expression compared with expression in the absence of the intron element (Kurachi et al., 1995, supra).

The use of introns is not limited to naturally occurring genomic sequence, and can include introns associated with a completely different gene or other DNA sequence. Accordingly, other untranslated (non-protein encoding) regions of nucleic acid, such as introns found in genomic sequences from cognate (related) genes and non-cognate (unrelated) genes can also function as filler or staffer polynucleotide sequences in accordance with the invention.

Donor nucleic acids, expression control elements, ITRs, poly A sequences, filler or staffer polynucleotide sequences can vary in length. In particular aspects, a sequence between about 1-10, 10-20, 20-30, 30-40, 40-50, 50-60, 60-75, 75-100, 100-150, 150-200, 200-250, 250-300, 300-400, 400-500, 500-750, 750-1,000, 1,000-1,500, 1,500-2,000, 2,000-2,500, 2,500-3,000, 3,000-3,500, 3,500-4,000, 4,000-4,500, 4,500-5,000 or more nucleotides in length up to the limit of AAV packaging size limit.

The CRISPR/Cas system including the Cas9 coding sequence and the sgRNA can be introduced/transferred/transduced/transfected into the target cell by way of AAV vector. The terms "transduce" and "transfect" refers to introduction of a molecule such as a nucleic acid into a cell or host organism. Accordingly, a transduced cell (e.g., in a mammal, such as a cell or tissue or organ cell), means a genetic change in a cell following incorporation of an exogenous molecule, for example, a polynucleotide or protein (e.g., a transgene) into the cell. Thus, a "transduced" cell is a cell into which, or a progeny thereof in which an exogenous molecule has been introduced. In methods and uses of the invention, a transduced cell can be in a subject, e.g., in vivo or ex vivo.

Methods and uses of the invention provide a means for delivering (transducing) CRISPR/Cas/sgRNA and optionally donor nucleic acid (transgenes) into host cells, including dividing and/or non-dividing cells. The AAV vectors, methods, uses and pharmaceutical formulations of the invention are additionally useful in a method of delivering, administering or providing a nucleic acid, or protein to a subject in need thereof, as a method of treatment. In this manner, the nucleic acid is transcribed and the protein may be produced in vivo in a subject. The subject may benefit from or be in need of the nucleic acid or protein because the subject has a deficiency of the nucleic acid or protein, or because production of the nucleic acid or protein in the subject may impart some therapeutic effect, as a method of treatment or otherwise.

In various embodiments, the AAV vectors are delivered to the eukaryotic cell in a subject. Subjects are typically animals and include human and veterinary applications. Suitable subjects therefore include mammals, such as humans, as well as non-human mammals (e.g., primates). Other subjects include primates (apes, gibbons, gorillas, chimpanzees, orangutans, macaques), a domestic animal (dogs and cats), a farm animal (poultry such as chickens and ducks, horses, cows, goats, sheep, pigs), and experimental animals (mouse, rat, rabbit, guinea pig). Human subjects include fetal, neonatal, infant, juvenile and adult subjects. For example, the subject can be a human younger than 20 year-old, 15 year-old, 10 year-old, 5 year-old, 3 year-old, 2 year-old, 1 year-old, 6 month-old, 3 month-old, or 1 month-old. Subjects can also include animal disease models, for example, mouse and other animal models of blood clotting diseases and others known to those of skill in the art.

Subjects appropriate for treatment include those having or at risk of producing an insufficient amount or having a deficiency in a functional gene product (protein), or produce an aberrant, partially functional or non-functional gene product (protein), which can lead to disease. In particular embodiments, a subject that would benefit from or is in need of disrupting, correcting or replacing a defective gene (e.g., PLP1), or is in need of disrupting, correcting or replacing a gene encoding a protein having defective or partial function or activity.

A therapeutic or beneficial effect of treatment is therefore any objective or subjective measurable or detectable improvement or benefit provided to a particular subject. A therapeutic or beneficial effect can but need not be complete ablation of all or any particular adverse symptom, disorder, illness, or complication of a disease. Thus, a satisfactory clinical endpoint is achieved when there is an incremental improvement or a partial reduction in an adverse symptom, disorder, illness, or complication caused by or associated with a disease, or an inhibition, decrease, reduction, suppression, prevention, limit or control of worsening or progression of one or more adverse symptoms, disorders, illnesses, or complications caused by or associated with the disease, over a short or long duration (hours, days, weeks, months, etc.).

The dose to achieve a therapeutic effect, e.g., the dose in vector genomes/per kilogram of body weight (vg/kg), will vary based on several factors including, but not limited to: route of administration, the nucleic acid expression required to achieve a therapeutic effect, the specific disease treated, any host immune response to the vector, and the stability of the protein expressed. One skilled in the art can determine a rAAV/vector genome dose range to treat a patient having a particular disease or disorder based on the aforementioned factors, as well as other factors.

Administration or in vivo delivery to a subject can be performed prior to development of an adverse symptom, condition, complication, etc. caused by or associated with the disease. For example, a screen (e.g., genetic) can be used to identify such subjects as candidates for invention compositions, methods and uses. Such subjects therefore include those screened positive for an insufficient amount or a deficiency in a functional gene product (protein), or that produce an aberrant, partially functional or nonfunctional gene product (protein).

Methods of administration or delivery include any mode compatible with a subject. Methods and uses of the invention include delivery and administration systemically, regionally or locally, or by any route, for example, by injection or infusion. Such delivery and administration include parenterally, e.g., intraocularly, intravascularly, intravenously, intramuscularly, intraperitoneally, intradermally, subcutaneously, or transmucosal. Exemplary administration and delivery routes include intravenous (i.v.), intraperitoneal (i.p.), intrarterial, subcutaneous, intra-pleural, intubation, intrapulmonary, intracavity, iontophoretic, intraorgan, intralymphatic. In particular embodiments, an AAV vector is administered or delivered parenterally, such as intravenously, intraarterially, intraocularly, intramuscularly, subcutaneously, or via catheter or intubation.

Doses can vary and depend upon whether the type, onset, progression, severity, frequency, duration, or probability of the disease to which treatment is directed, the clinical endpoint desired, previous or simultaneous treatments, the general health, age, gender, race or immunological competency of the subject and other factors that will be appreciated by the skilled artisan. The dose amount, number, frequency or duration may be proportionally increased or reduced, as indicated by any adverse side effects, complications or other risk factors of the treatment or therapy and the status of the subject. The skilled artisan will appreciate the factors that may influence the dosage and timing required to provide an amount sufficient for providing a therapeutic or prophylactic benefit.

The subject AAV vectors, and other compositions, can be incorporated into pharmaceutical compositions, e.g., a pharmaceutically acceptable carrier or excipient. Such pharmaceutical compositions are useful for, among other things, administration and delivery to a subject in vivo or ex vivo.

As used herein the term "pharmaceutically acceptable" and "physiologically acceptable" mean a biologically acceptable formulation, gaseous, liquid or solid, or mixture thereof, which is suitable for one or more routes of administration, in vivo delivery or contact. A "pharmaceutically acceptable" or "physiologically acceptable" composition is a material that is not biologically or otherwise undesirable, e.g., the material may be administered to a subject without causing substantial undesirable biological effects. Thus, such a pharmaceutical composition may be used, for example in administering a viral vector or viral particle to a subject.

Such compositions include solvents (aqueous or non-aqueous), solutions (aqueous or non-aqueous), emulsions (e.g., oil-in-water or water-in-oil), suspensions, syrups, elixirs, dispersion and suspension media, coatings, isotonic and absorption promoting or delaying agents, compatible with pharmaceutical administration or in vivo contact or delivery. Aqueous and non-aqueous solvents, solutions and suspensions may include suspending agents and thickening agents. Such pharmaceutically acceptable carriers include tablets (coated or uncoated), capsules (hard or soft), microbeads, powder, granules and crystals. Supplementary active compounds (e.g., preservatives, antibacterial, antiviral and antifungal agents) can also be incorporated into the compositions.

Pharmaceutical compositions can be formulated to be compatible with a particular route of administration or delivery, as set forth herein or known to one of skill in the art. Thus, pharmaceutical compositions include carriers, diluents, or excipients suitable for administration by various routes.

Compositions suitable for parenteral administration comprise aqueous and nonaqueous solutions, suspensions or emulsions of the active compound, which preparations are typically sterile and can be isotonic with the blood of the intended recipient. Non-limiting illustrative examples include water, saline, dextrose, fructose, ethanol, animal, vegetable or synthetic oils.

Cosolvents and adjuvants may be added to the formulation. Non-limiting examples of cosolvents contain hydroxyl groups or other polar groups, for example, alcohols, such as isopropyl alcohol; glycols, such as propylene glycol, polyethyleneglycol, polypropylene glycol, glycol ether; glycerol; polyoxyethylene alcohols and polyoxyethylene fatty acid esters. Adjuvants include, for example, surfactants such as, soya lecithin and oleic acid; sorbitan esters such as sorbitan trioleate; and polyvinylpyrrolidone.

Pharmaceutical compositions and delivery systems appropriate for the compositions, methods and uses of the invention are known in the art (see, e.g., Remington: The Science and Practice of Pharmacy (2003) 20th ed., Mack Publishing Co., Easton, Pa.; Remington's Pharmaceutical Sciences (1990) 18th ed., Mack Publishing Co., Easton, Pa.; The Merck Index (1996) 12th ed., Merck Publishing Group, Whitehouse, N.J.; Pharmaceutical Principles of Solid Dosage Forms (1993), Technonic Publishing Co., Inc., Lancaster, Pa.; Ansel and Stoklosa, Pharmaceutical Calculations (2001) 11th ed., Lippincott Williams & Wilkins, Baltimore, Md.; and Poznansky et al, Drug Delivery Systems (1980), R. L. Juliano, ed., Oxford, N.Y., pp. 253-315).

A "unit dosage form" as used herein refers to physically discrete units suited as unitary dosages for the subject to be treated; each unit containing a predetermined quantity optionally in association with a pharmaceutical carrier (excipient, diluent, vehicle or filling agent) which, when administered in one or more doses, is calculated to produce a desired effect (e.g., prophylactic or therapeutic effect). Unit dosage forms may be within, for example, ampules and vials, which may include a liquid composition, or a composition in a freeze-dried or lyophilized state; a sterile liquid carrier, for example, can be added prior to administration or delivery in vivo. Individual unit dosage forms can be included in multi-dose kits or containers. AAV vectors, and pharmaceutical compositions thereof can be packaged in single or multiple unit dosage form for ease of administration and uniformity of dosage.

In related embodiments, the AAV delivery system described herein can be readily adapted to deliver into a target cell (e.g., an OPC or NSC, either in vitro, in vivo or ex vivo) other nucleases (such as TALEN or ZFN) or RNAi constructs (that encode and produce functional siRNA once inside the target cell) or ASO constructs (that encode and produce functional anti-sense oligoes).

Applications

The methods and compositions disclosed herein are for providing cell-based therapies for myelin-related disorders. The cell may be modified in vivo or may be modified ex vivo and subsequently administered to a subject. In some embodiments, NSCs, OPCs, neuron cells, and glial cells such as oligodendrocytes, astrocytes, ependymal cells, and microglia cells in the central nervous system of patients would be edited in situ. In some embodiments, cells would be modified ex vivo and transplanted to patients.

Use of the subject's own cells eliminates the requirement of HLA matching between donor and recipient for the transplant. Furthermore, the genetically modified cells described herein have been shown to be suitable for serial (secondary) transplantations in that stem cells can be isolated from the subject and these cells retain the genetic modification and can be administered to one or more additional subjects. Thus, the methods and compositions provide for the treatment and/or prevention of a myelin-related disorder.

Targeted deletion of PLP1, a portion of PLP1, or a PLP regulatory element may be used to correct an aberrant gene, create a loss-of function mutation within an endogenous gene, or change the expression of an endogenous gene. In other aspects, targeted integration of an anti-PLP1 donor of a PLP1 or PLP1 genetic regulatory element nucleotide sequence may be used to correct an aberrant gene, insert a wild type gene, create a gain-of-function mutation within an endogenous gene, or change the expression of an endogenous gene. For instance, a transgene encoding a PLP1 or a PLP1 genetic regulatory element transgene may be integrated into a cell to provide a cell (e.g., oligodendrocyte or a progenitor) that produces a non-deleterious protein capable of enhancing functional myelin production. Targeted knock out or gene silencing of PLP1 or a PLP1 genetic regulatory element, or modification by the methods described herein may provide a cell that enhances functional myelin production by reducing PLP1 toxicity through inactivation of PLP1 gene. Genomic editing may also include correction or introduction of mutations (e.g., point mutations) in an endogenous gene, for example to modify endogenous PLP1 gene expression.

The compositions (e.g., cells and/or nucleotides) described herein can be administered to a subject to treat myelin related diseases and disorders. Myelin-related diseases and disorders contemplated for treatment by some aspects of the present invention can include can include any disease, condition (e.g., those occurring from traumatic spinal cord injury and cerebral infarction), or disorder related to demyelination, insufficient myelination and remyelination, or dysmyelination in a subject. A myelin related disorder as used herein can arise from a myelination related disorder or demyelination resulting from a variety of neurotoxic insults. "Demyelination" as used herein, refers to the act of demyelinating, or the loss of the myelin sheath insulating the nerves, and is the hallmark of some neurodegenerative autoimmune diseases, including multiple sclerosis, transverse myelitis, chronic inflammatory demyelinating polyneuropathy, and Guillain-Barre Syndrome. Leukodystrophies are caused by inherited enzyme deficiencies, which cause abnormal formation, destruction, and/or abnormal turnover of myelin sheaths within the CNS white matter. Both acquired and inherited myelin disorders share a poor prognosis leading to major disability. Thus, some embodiments of the present invention can include methods for the treatment of neurodegenerative autoimmune diseases in a subject. Remyelination of neurons requires oligodendrocytes. The term "remyelination", as used herein, refers to the re-generation of the nerve's myelin sheath by replacing myelin producing cells or restoring their function.

Myelin related diseases or disorders which may be treated or ameliorated by the methods of the present invention include diseases, disorders or injuries which relate to dysmyelination or demyelination in a subject's brain cells, e.g., CNS neurons. Such diseases include, but are not limited to, diseases and disorders in which the myelin which surrounds the neuron is either absent, incomplete, not formed properly, or is deteriorating. Such disease include, but are not limited to, multiple sclerosis (MS), neuromyelitis optica (NMO), progressive multifocal leukoencephalopathy (PML), encephalomyelitis (EPL), central pontine myelolysis (CPM), adrenoleukodystrophy, Alexander's disease, Pelizaeus Merzbacher disease (PMD), Wallerian Degeneration, optic neuritis, transverse myelitis, amylotrophic lateral sclerosis (ALS), Huntington's disease, Alzheimer's disease, Parkinson's disease, spinal cord injury, traumatic brain injury, post radiation injury, neurologic complications of chemotherapy, stroke, acute ischemic optic neuropathy, vitamin E deficiency, isolated vitamin E deficiency syndrome, AR, Bassen-Kornzweig syndrome, Marchiafava-Bignami syndrome, metachromatic leukodystrophy, trigeminal neuralgia, acute disseminated encephalitis, Guillian-Barre syndrome, Marie-Charcot-Tooth disease and Bell's palsy.

Myelin related diseases or disorders which may be treated or ameliorated by the methods of the present invention include a disease or disorder characterized by a myelin deficiency. Insufficient myelination in the central nervous system has been implicated in a wide array of neurological disorders. Among these are forms of cerebral palsy in which a congenital deficit in forebrain myelination in children with periventricular leukomalacia, contributes to neurological morbidity (Goldman et al., 2008) Goldman, S. A., Schanz, S., and Windrem, M. S. (2008). Stem cell-based strategies for treating pediatric disorders of myelin. Hum Mol Genet. 17, R76-83. At the other end of the age spectrum, myelin loss and ineffective repair may contribute to the decline in cognitive function associated with senescence (Kohama et al., 2011) Kohama, S. G., Rosene, D. L., and Sherman, L. S. (2011) Age (Dordr). Age-related changes in human and non-human primate white matter: from myelination disturbances to cognitive decline. Therefore, it is contemplated that effective compounds and methods of enhancing myelination and/or remyelination may have substantial therapeutic benefits in halting disease progression and restoring function in PMD and in a wide array of myelin-related disorders.

In some embodiments, the compositions of the present invention can be administered to a subject that does not have, and/or is not suspected of having, a myelin related disorder in order to enhance or promote a myelin dependent process. In some embodiments, compounds described herein can be administered to a subject to promote myelination of CNS neurons in order to enhance cognition, which is known to be a myelin dependent process, in cognitive healthy subjects. In certain embodiments, compounds described herein can be administered in combination with cognitive enhancing (nootropic) agents. Exemplary agents include any drugs, supplements, or other substances that improve cognitive function, particularly executive functions, memory, creativity, or motivation, in healthy individuals. Non limiting examples include racetams (e.g., piracetam, oxiracetam, and aniracetam), nutraceuticals (e.g., bacopa monnieri, panax ginseng, ginko biloba, and GABA), stimulants (e.g., amphetamine pharmaceuticals, methylphenidate, eugeroics, xanthines, and nicotine), L-Theanine, Tolcapone, Levodopa, Atomoxetine, and Desipramine.

One particular aspect of the present invention contemplates the treatment of PMD in a subject. The method includes administering to the subject a therapeutically effective amount of genetically modified cells or nucleotide compositions described above.

The overall dosage will be a therapeutically effective amount depending on several factors including the overall health of a subject, the subject's disease state, severity of the condition, the observation of improvements and the formulation and route of administration of the selected agent(s). Determination of a therapeutically effective amount is within the capability of those skilled in the art. The exact formulation, route of administration and dosage can be chosen by the individual physician in view of the subject's condition.

In certain embodiments, genetically modified cells or nucleotide compositions described herein may be administered in an amount effective to enhance myelin production of CNS neurons in a subject by an increase in the amount of myelin proteins (e.g., MBP) of at least 5%, 10%, 20%, 25%, 30%, 40%, 50%, 60%, 70%, 75%, 80%, 85%, 90%, 95%, 100%, 110%, 120%, 130%, 140%, 150%, 160%, 170%, 180%, 190%, 200%, 250%, 300%, 350%, 400%, 450%, 500%, 550%, 600%, 650%, 700%, 750%, 800%, 850%, 900%, 950%, or 1000% as compared to the level of myelin proteins of an untreated CNS neurons or subject.

In other embodiments, genetically modified cells or nucleotide compositions may be administered in an amount effective to promote survival of CNS neurons in a subject by an increase in the number of surviving neurons of at least 5%, 10%, 20%, 25%, 30%, 40%, 50%, 60%, 70%, 75%, 80%, 85%, 90%, 95%, 100%, 110%, 120%, 130%, 140%, 150%, 160%, 170%, 180%, 190%, 200%, 250%, 300%, 350%, 400%, 450%, 500%, 550%, 600%, 650%, 700%, 750%, 800%, 850%, 900%, 950%, or 1000% as compared to the number of surviving neurons in an untreated CNS neurons or subject.

Another strategy for treating a subject suffering from myelin-related disorder is to administer a therapeutically effective amount of genetically modified cells or nucleotide compositions described herein along with a therapeutically effective amount of an oligodendrocyte differentiation and/or proliferation inducing agent(s) and/or anti-neurodegenerative disease agent. Examples of anti-neurodegenerative disease agents include L-dopa, cholinesterase inhibitors, anticholinergics, dopamine agonists, steroids, and immunomodulators including interferons, monoclonal antibodies, and glatiramer acetate.

Therefore, in a further aspect of the invention, the genetically modified cells or nucleotide compositions described herein can be administered as part of a combination therapy with adjunctive therapies for treating neurodegenerative and myelin related disorders.

The phrase "combination therapy" embraces the administration of the oligodendrocyte precursor differentiation inducing compounds described herein and a therapeutic agent as part of a specific treatment regimen intended to provide a beneficial effect from the co-action of these therapeutic agents. When administered as a combination, the oligodendrocyte precursor differentiation inducing compound and a therapeutic agent can be formulated as separate compositions. Administration of these therapeutic agents in combination typically is carried out over a defined time period (usually minutes, hours, days or weeks depending upon the combination selected).

"Combination therapy" is intended to embrace administration of these therapeutic agents in a sequential manner, that is, wherein each therapeutic agent is administered at a different time, as well as administration of these therapeutic agents, or at least two of the therapeutic agents, in a substantially simultaneous manner. Substantially simultaneous administration can be accomplished, for example, by administering to the subject a single capsule having a fixed ratio of each therapeutic agent or in multiple, single capsules for each of the therapeutic agents. Sequential or substantially simultaneous administration of each therapeutic agent can be effected by any appropriate route including, but not limited to, oral routes, intravenous routes, intramuscular routes, and direct absorption through mucous membrane tissues. The therapeutic agents can be administered by the same route or by different routes. For example, a first therapeutic agent of the combination selected may be administered by intravenous injection while the other therapeutic agents of the combination may be administered orally. Alternatively, for example, all therapeutic agents may be administered orally or all therapeutic agents may be administered by intravenous injection. The sequence in which the therapeutic agents are administered is not narrowly critical. "Combination therapy" also can embrace the administration of the therapeutic agents as described above in further combination with other biologically active ingredients (such as, but not limited to, a second and different therapeutic agent) and non-drug therapies (e.g., surgery).

In another aspect of the invention, the therapeutic agents administered in a combination therapy with the genetically modified cells or nucleotide compositions described herein can include at least one anti-neurodegenerative agent such as but not limited to, an immunotherapeutic agent.

An immunotherapeutic agent for use in the methods of the present invention can include therapies which target the immune component of the disease and/or the acute inflammatory response evidenced during an acute attack in remitting-relapsing myelin-related disorder such as multiple sclerosis. Examples include, but are not limited to immunomodulators such as interferon beta-1a and beta-1b (Avonex and Betaseron respectively), natalizumab (Copaxone) natalizumab (Tysabri), glatiramer acetate (Copaxone) or mitoxantrone.

The invention is further illustrated by the following examples, which are not intended to limit the scope of the claims.

Example 1 Nuclease Mediated PLP1 Inactivation to Treat Genetic Myelin Disorders

Introduction

Abnormal myelination results in aberrant neuronal-signaling and neurological dysfunction. Restoration of the myelinating-capacity in these patients by correction of the genetic abnormalities within their endogenous, myelinating cells represents a promising curative avenue, however the feasibility of this therapeutic approach has yet to be demonstrated. Therefore, we chose to validate this paradigm by focusing on a severe, archetypal leukodystrophy called Pelizaeus-Merzbacher Disease (PMD).

PMD is a severe X-linked genetic disorder of myelin caused by mutations in the proteolipid protein 1 (PLP1). PMD patients typically experience severe neurological disease, including profound cognitive and motor disability, which invariably culminates in early mortality during childhood or adolescence. Therefore, we looked to determine if severe PMD patients could be treated through introduction of nuclease mediated insertions or deletions (indels) in the PLP1 gene or its regulatory elements which effectively and permanently inactivate or reduce PLP1 expression (PLP1-indel). Nuclease mediated indels can be targeted to oligodendrocytes or their progenitors including neural stem cells or oligodendrocyte precursor cells (OPCs). Targeting of progenitor cells would provide a permanent and self-amplifying therapy as PLP-indel progenitor cells would continue to generate functional PLP1-indel oligodendrocytes over the life of the patient. Given the many distinct and various PMD-causative mutations already identified in patients, our PLP1-indel approach is unique as it provides a universal approach applicable to all PMD patients.

Jimpy Mouse

To develop a PLP1-indel therapeutic we utilized a PMD mouse model called jimpy. This mouse harbors a point mutation in splice acceptor site of intron 4 in the PLP1 gene, leading to a misfolded PLP1 protein that eventually causes oligodendrocyte loss, profound hypomyelination, severe tremor, ataxia, seizures, and early mortality by the third postnatal week. Therefore it effectively recapitulates many aspects of severe PMD seen in human patients.

Figure 2:
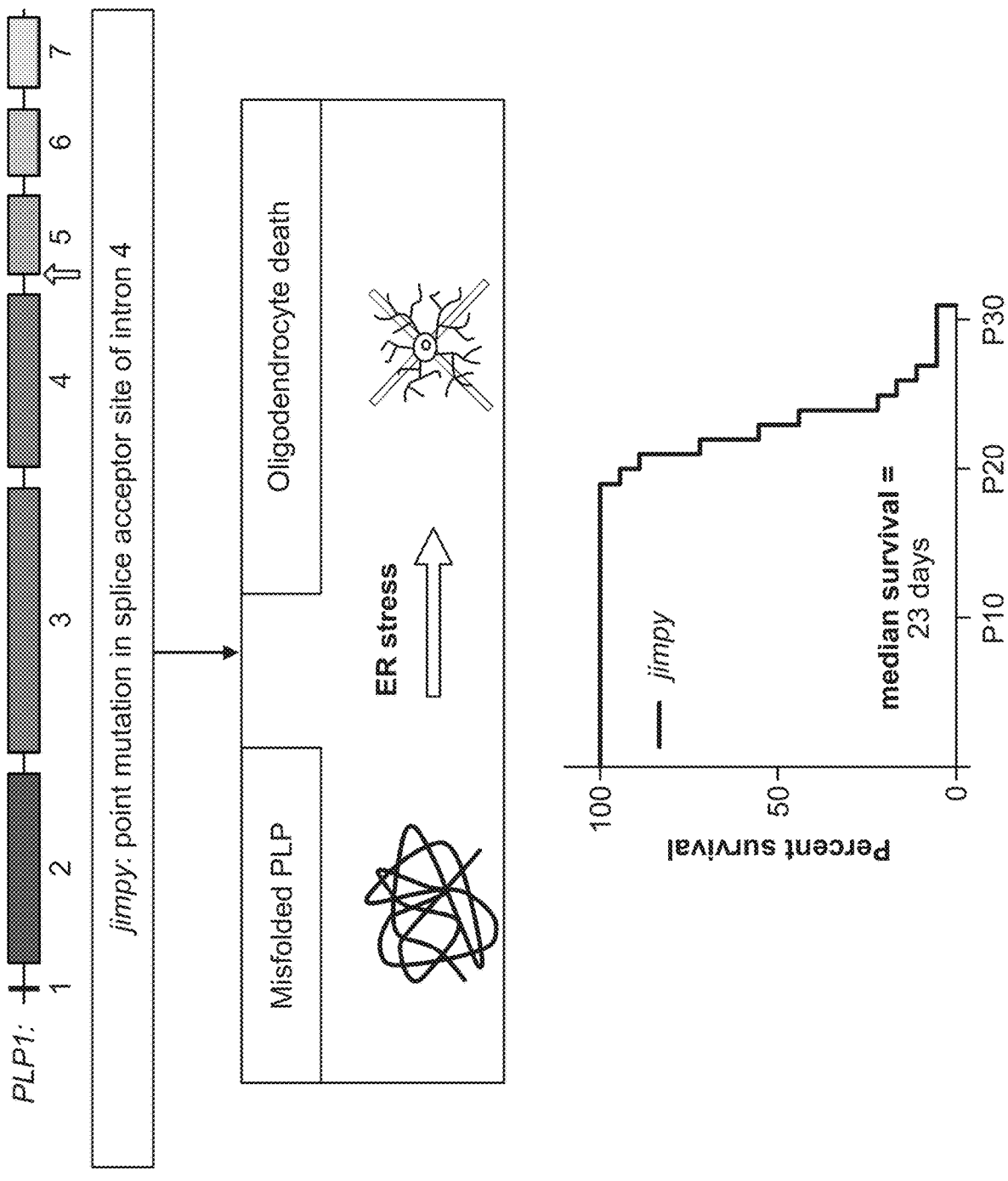
FIG. 2 is a schematic drawing (not to scale) showing the location of the jimpy genetic mutation in the mouse PLP1 gene, and the resulting gene product that eventually causes oligodendrocytes death. The bottom of the figure shows severely reduced lifespan of jimpy mice with a median survival of about 23 days.

The Jimpy mice represent the most severe model of PMD. FIG. 2 is a schematic drawing (not to scale) showing the location of the jimpy genetic mutation in the mouse PLP1 gene, and the resulting gene product that eventually causes oligodendrocytes death. The bottom of the figure shows severely reduced lifespan of jimpy mice with a median survival of only about 23 days.

Figure 3:
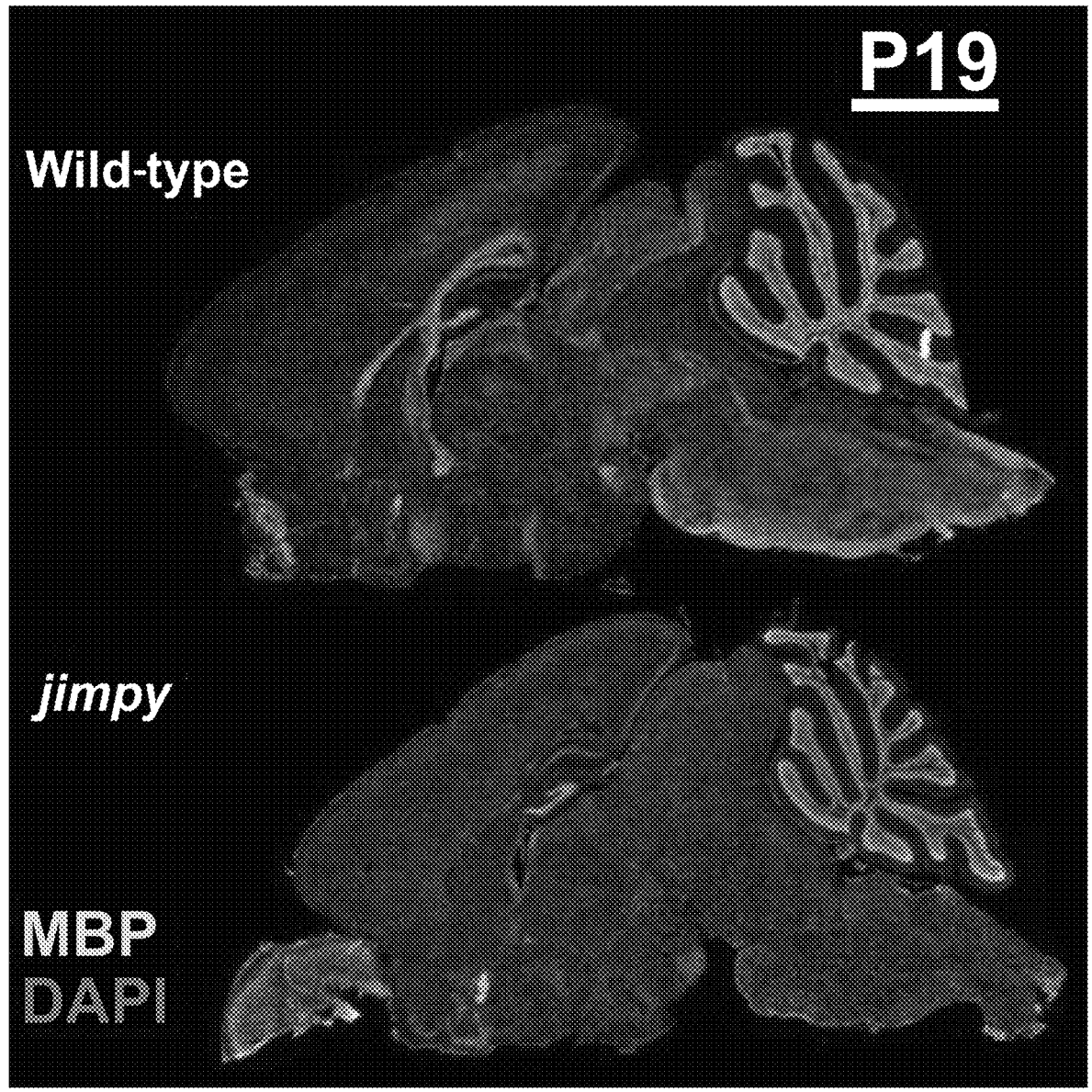
FIG. 3 shows severe hypomyelination in jimpy mouse brain. Note the significantly less myelin basic protein (MBP) staining marking mature oligodendrocytes in the postnatal day 19 (P19) jimpy mouse brain section compared to that of the wild-type control. The jimpy mouse also display neurological symptoms of intention tremor and ataxia at the same age (data not shown).

FIG. 3 shows severe hypomyelination in jimpy mouse brain. Note the significantly less MBP staining in the P19 (19 days postnatal) jimpy mouse brain section compared to that of the wild-type control. The jimpy mouse also display intention tremor and ataxia at the same age (data not shown).

Guide RNA Selection and Validation

CRISPR-Cas9 is one example of an efficient nuclease-mediated system to induce indels in mammalian cells by introduction of the nuclease Cas9 and a 22 bp single-guide RNA (sgRNA). Suitable sgRNA were designed as described in Hsu et al. (2013) *Nature Biotechnology* 31, 827-832. Specifically, sgRNAs were selected to maximize on-target and minimize off-target indel formation as well as early exon targeting to increase the efficiency of nonsense mediated decay. sgRNAs were validated for nuclease activity by Clontech's Guide-it sgRNA Screening Kits and for functional indel induction by electroporating plasmid expressing SaCas9 or SpCas9 and sgRNA into mouse and human cells using the Thermofisher Neon Transfection System. Cutting efficiency and sgRNA ranking was determined by quantification of indel formation through deep sequencing using the illumina MiSeq System. Top sgRNAs are detailed in Table 1.

TABLE 1

Top Validated sgRNA sequences

| Nuclease | sgRNA Identifier | Sequence (5'-3') | Target PLP1 Exon |
|---|---|---|---|
| SpCas9 | A | AAGACCACCATCTGCGGCAANGG (SEQ ID NO: 1) | 3 |
| SpCas9 | B | CCAGCAGGAGGGCCCCATAANGG (SEQ ID NO: 2) | 3 |
| SaCas9 | C | GTCAGAGTGCCAAAGACATGGNNGRRT (SEQ ID NO: 3) | 1 |

Figure 4:
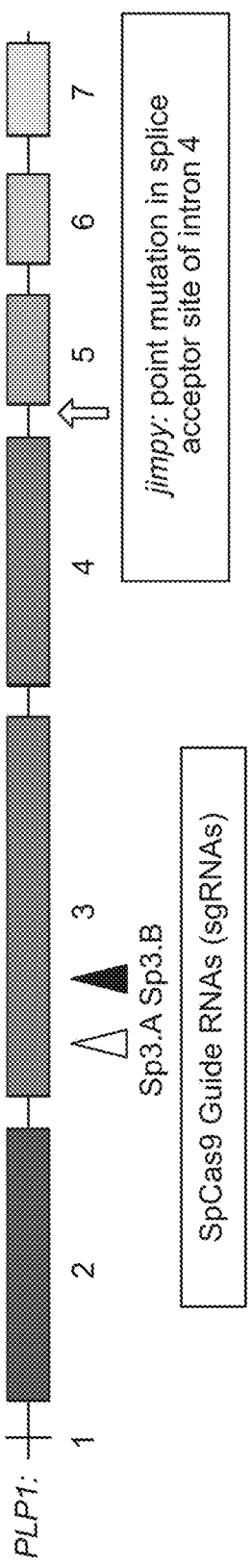
FIGS. 4 and 5 are schematic drawings showing an exemplary approach to knockout the PLP1 gene in the zygote of a jimpy mouse, through CRISPR SpCas9/dual guide RNAs (sgRNAs) targeting of exon 3, to create the CRISPR-knockout jimpy (CR-impy [or crimpy]) progeny mice.
Figure 5:
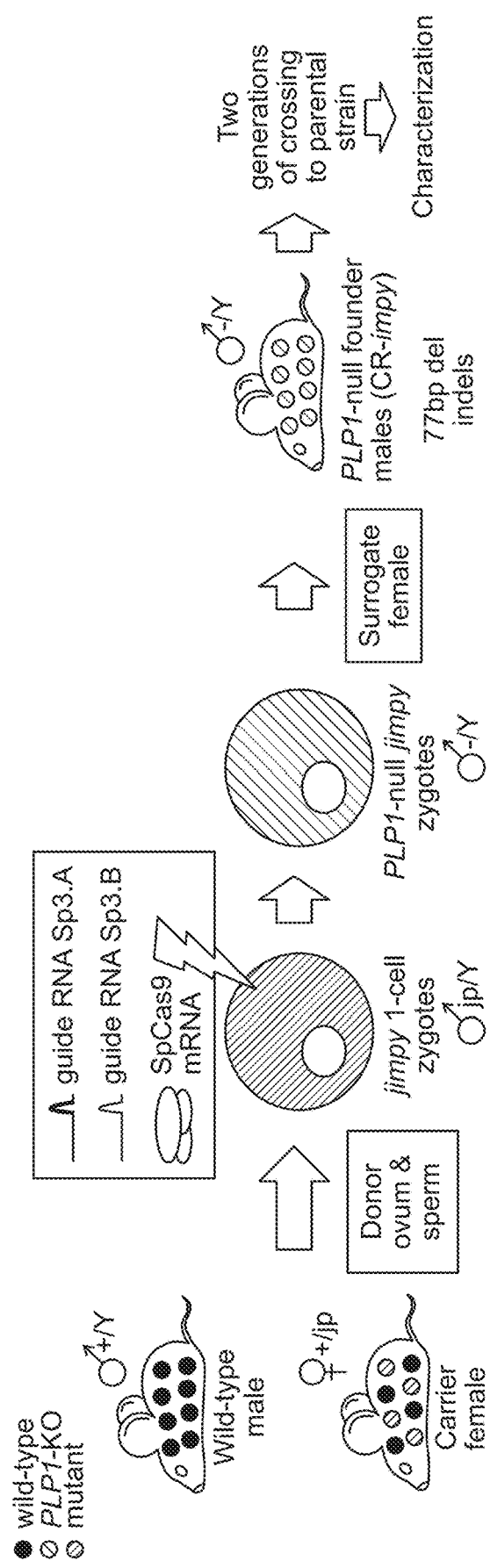

FIGS. 4 and 5 are schematic drawings showing an exemplary approach to knockout the PLP1 gene in the zygote of a jimpy mouse, through CRISPR SpCas9/dual guide RNAs (sgRNAs) targeting of exon 3, to create the CR-impy KO progeny mice. FIG. 4 shows the relative locations of the sgRNA A and B targeting sites in exon 3. FIG. 5 shows the general experimental approach to generate the jimpy male zygote for receiving the sgRNAs and the SpCas9 mRNA. Successful CRISPR/Cas9 mediated knockout of the jimpy PLP1 gene leads to the birth of a PLP1 null male CR-impy founder born by a surrogate host female. Two generations of crossing to the parental strain yield progeny mice for further characterization.

SPCas9-Mediated PLP1 Deletion in Animals

As an initial proof-of-concept for our therapeutic PLP1-indel strategy zygotes from jimpy breeders were electroplated with 200 ng/µl SpCas9 mRNA and 10 ng/µl each of sgRNAs A and B and then implanted into surrogate females (see FIG. 5). This resulted in the generation of a CRISPR-knockout jimpy (CR-impy [or crimpy]) male mouse carrying an ~80-nucleotide deletion on the 5' end of exon 3 in PLP1. While jimpy males exhibit severe phenotypes and die by the third postnatal week, the crimpy male was strikingly distinct from jimpy males as it displayed no tremor, seizures, ataxia, or early mortality (data not shown). Remarkably this crimpy male was able to successfully breed and lived more than six months before it was sacrificed for histological analysis which demonstrated full myelination of the central nervous system indistinguishable from wild type (see FIG. 1). Transmission of the crimpy allele to healthy grandsons confirms the dramatic therapeutic effect of our PLP1-indel treatment.

Figure 6:
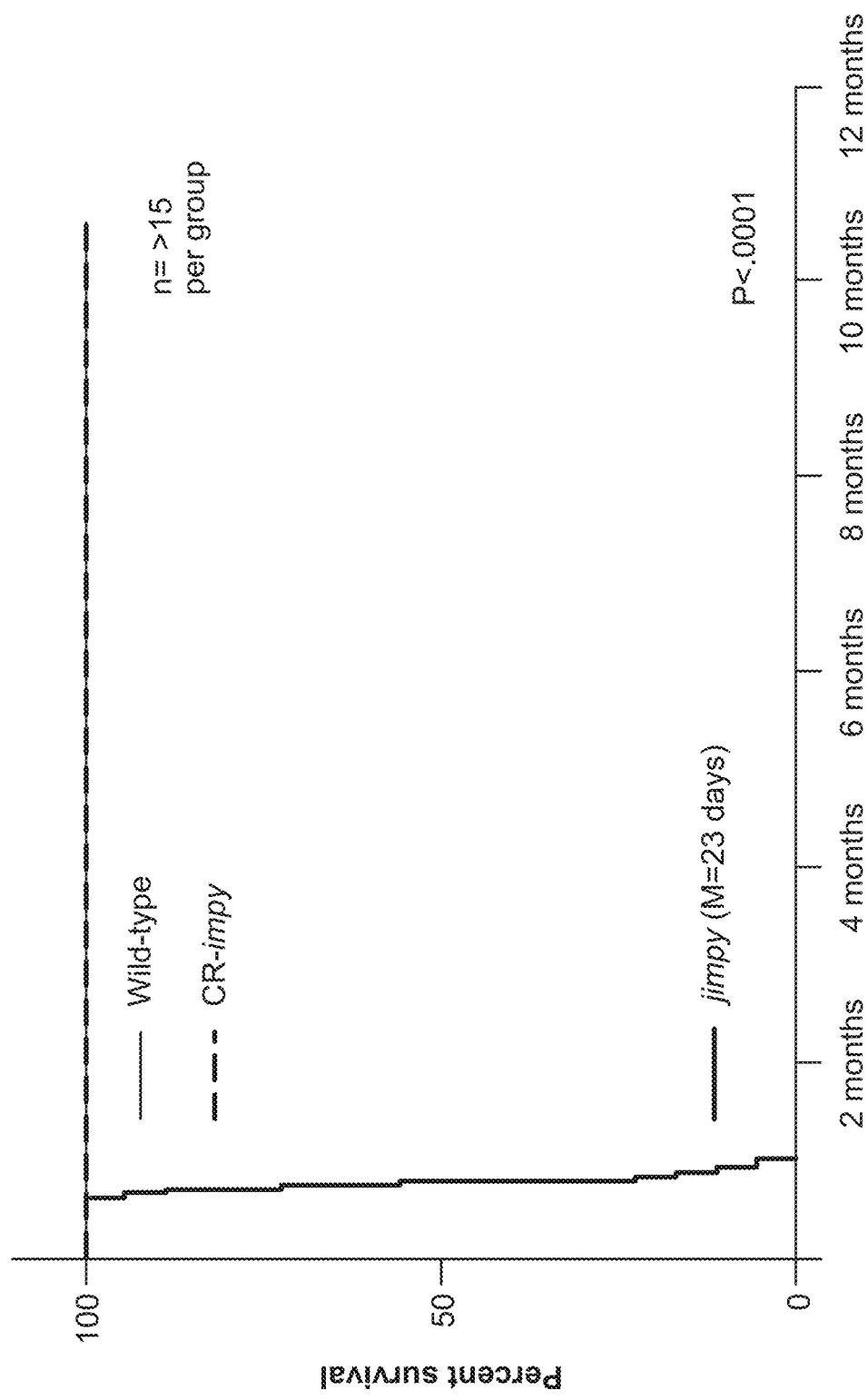
FIG. 6 shows that the CR-impy mice have a restored lifespan compared to the jimpy and wild-type controls.

Indeed, FIG. 6 shows that the CR-impy mice have a restored lifespan compared to the jimpy and wild-type controls (n>15 for each group, p<0.0001).

Figure 7:
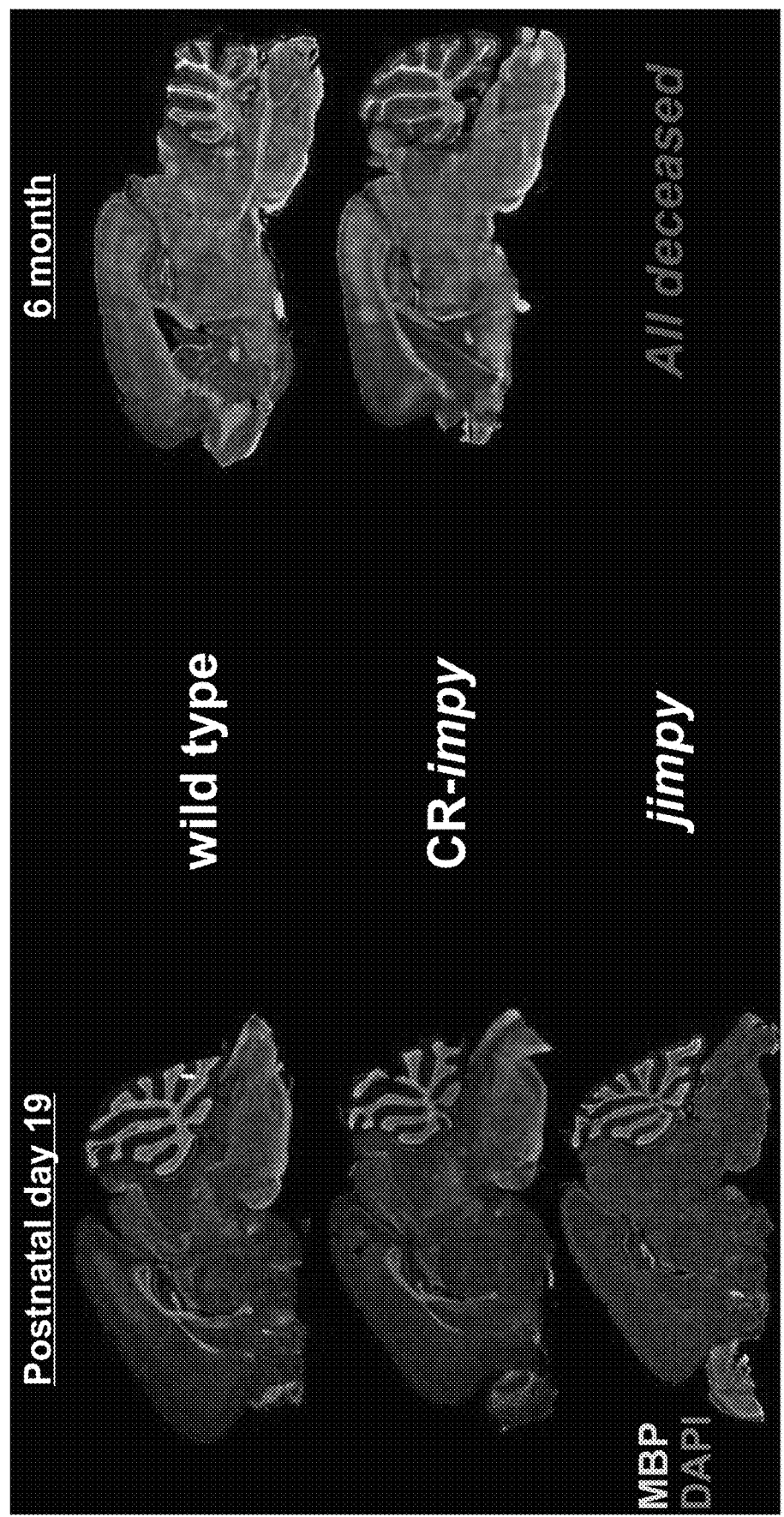
FIG. 7 shows that the CR-impy mice show recovery in mature oligodendrocytes by whole-brain IHC that detects MBP. Compare postnatal day 19 and 6 months postnatal.

FIG. 7 shows that the CR-impy mice show recovery in mature oligodendrocytes by whole-brain IHC that detects MBP. At postnatal D19, both the wild-type and CR-impy mice have significantly more MBP staining than that of jimpy mice. At 6 months postnatal, while all jimpy mice have died, the levels of MBP staining in the wild-type and CR-impy mice are indistinguishable.

Two additional functional tests were used to assess the restoration of motor coordination and locomotion in the CR-impy mice.

FIG. 8 shows a schematic drawing for the rotarod testing for assessing motor coordination of CR-impy mice, where motor coordination is quantitated by a measured time to fall from the rotating bar when the rotating bar is accelerated. The measurements were done at P19, 2 months, and 6 months postnatal, in wild-type, jimpy, and CR-impy mice at each time point. Statistical significance between the different values is indicated by p values. At P19, both the wild-type and CR-impy mice had statistically significantly longer time to fall compared to that of the jimpy mice. At 2 and 6 months postnatal, while all jimpy mice have died, the levels of measured time to fall in the wild-type and CR-impy mice are indistinguishable. The results show restoration of motor coordination in CR-impy mice compared to wild-type and jimpy mice.

Figure 9:
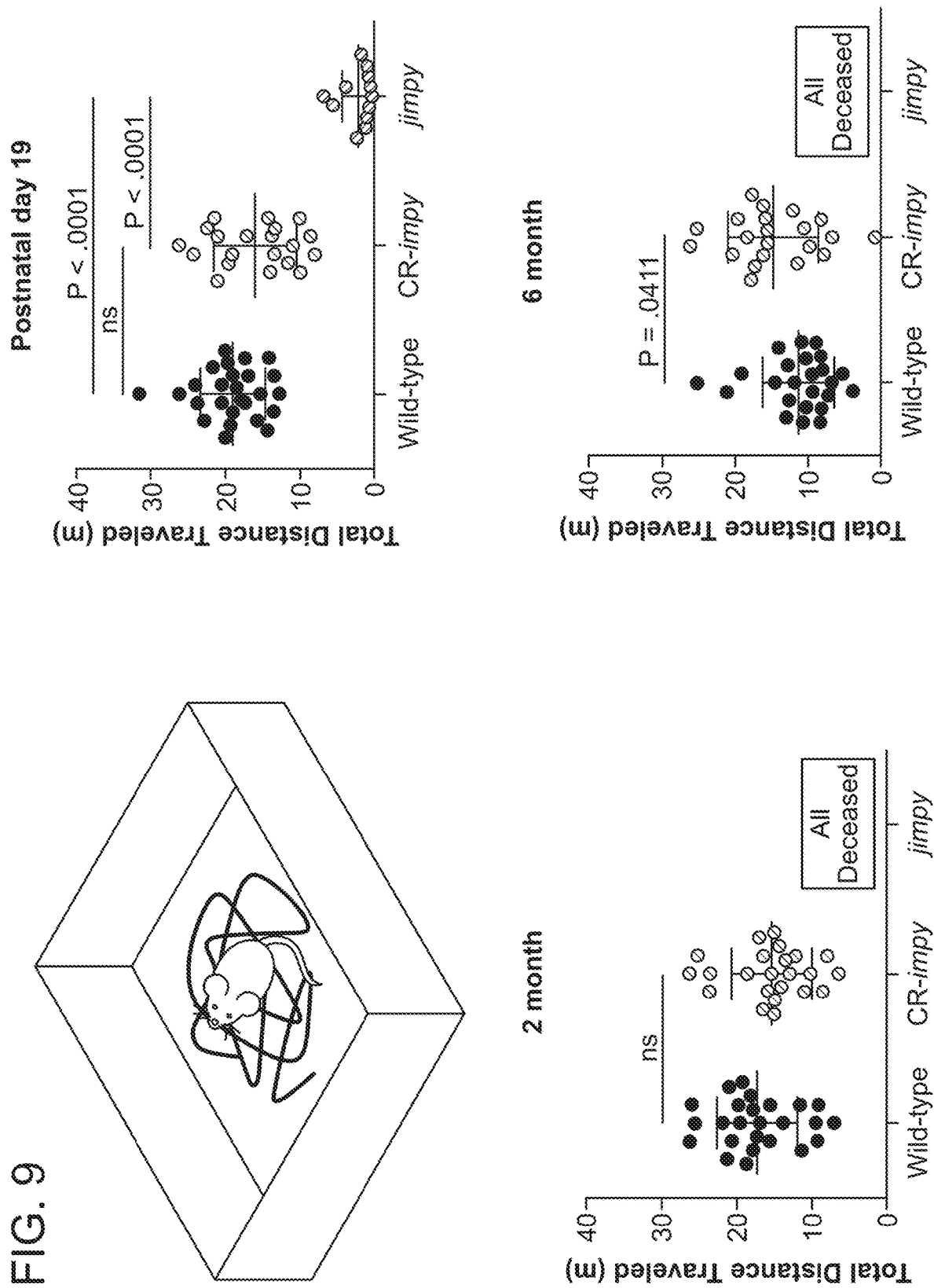
FIG. 9 shows a schematic drawing for the open field testing for assessing locomotor activity of CR-impy mice, where locomotor activity is quantitated by a measured total distance traveled in a box as tracked by automated video tracking for 5 minutes. The measurements were done at postnatal day 19 (P19), 2 months postnatal, and 6 months postnatal, in wild-type, jimpy, and CR-impy mice at each time point. Statistical significance between the different values is indicated by p values. The results show restoration of locomotor activity in CR-impy mice compared to wild-type and jimpy mice.

FIG. 9 shows a schematic drawing for the open field testing for assessing locomotor activity of CR-impy mice, where locomotor activity is quantitated by a measured total distance traveled in a box as tracked by automated video tracking for 5 minutes. The measurements were done at P19, 2 months, and 6 months postnatal, in wild-type, jimpy, and CR-impy mice at each time point. Statistical significance between the different values is indicated by p values. At P19, both the wild-type and CR-impy mice had statistically significantly longer total distance traveled compared to that of the jimpy mice. At 2 and 6 months postnatal, while all jimpy mice have died, the levels of measured total distance traveled in the wild-type and CR-impy mice are indistinguishable. The results show restoration of locomotor activity in CR-impy mice compared to wild-type and jimpy mice.

Figure 10:
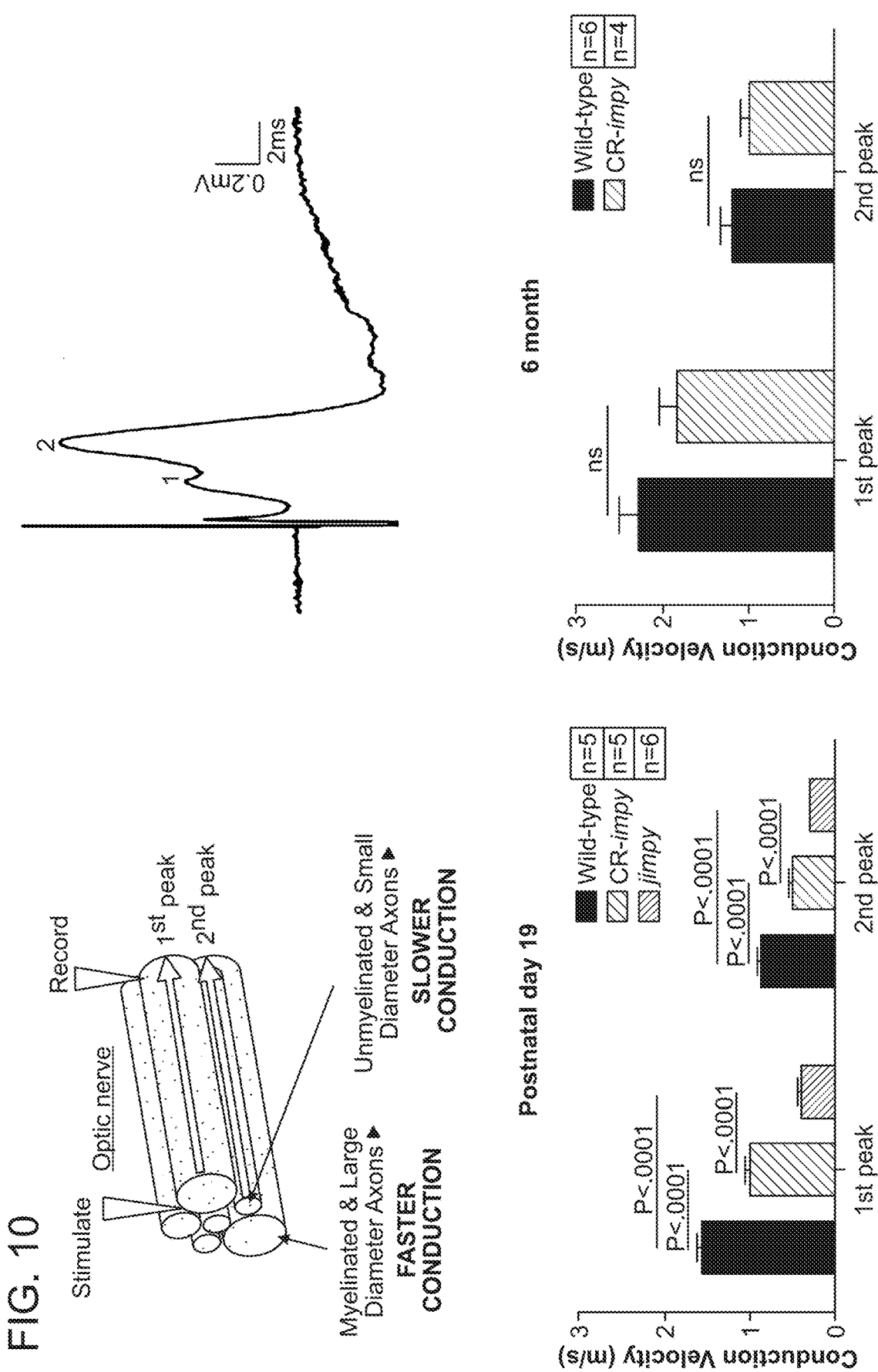
FIG. 10 shows a schematic drawing for the optic nerve conduction velocity testing and the representative results of the faster and slower conduction peaks—$1^{st}$ peak and $2^{nd}$ peak, respectively. Myelinated and large diameter axons generally have faster conductivity compared to unmyelinated and smaller diameter axons. At postnatal day 19 (P19), fast and slow conduction velocities, as measured by the $1^{st}$ and the $2^{nd}$ peaks, respectively, are both statistically significantly different between any two of the wild-type, the jimpy mice, and the CR-impy mice. At 6 months postnatal, however, while all jimpy mice have died, no difference is observed between the wild-type and CR-impy mice.

Further functional test was conducted based on a measurement of conduction velocity after axon stimulation. FIG. 10 shows a schematic drawing for the optic nerve conduction velocity testing and the representative results of the faster and slower conduction peaks—$1^{st}$ peak and $2^{nd}$ peak, respectively. Myelinated and large diameter axons generally have faster conductivity compared to unmyelinated and smaller diameter axons. At postnatal D19, fast and slow conduction velocities, as measured by the $1^{st}$ and the $2^{nd}$ peaks, respectively, are both statistically significantly different between any two of the wild-type, the jimpy mice, and the CR-impy mice. At 6 months postnatal, however, while all jimpy mice have died, the difference between the wild-type and CR-impy mice, if any, becomes statistically insignificant. This suggests that axon conduction velocity speed in CR-impy mice, while initially lagging behind that of the wild-type mice, eventually catches up over time.

Indeed, electron microscopy (EM) imaging of the wild-type and CR-impy mice optic nerves at about 6 months of age reveals no discernible difference. See FIG. 11.

The fact that CR-impy mice continued to show similar functional performance to that of wild-type at 6 months suggests long-term, functional stability of the gene-therapy mediated correction.

These results demonstrate that introduction of inactivating indels in PLP1 can fully rescue a mouse model of PMD.

Summary

The present disclosure involves a method of generating genetically modified cells and methods for their use in the treatment of human disorders of myelin. Specifically, we used nuclease-mediated genetic disruption of the proteolipid protein 1 (PLP1) gene as a novel therapeutic approach for myelin-related disorders with efficacy demonstrated in the context of a leukodystrophy called Pelizaeus Merzbacher Disease (PMD).

Figure 12:
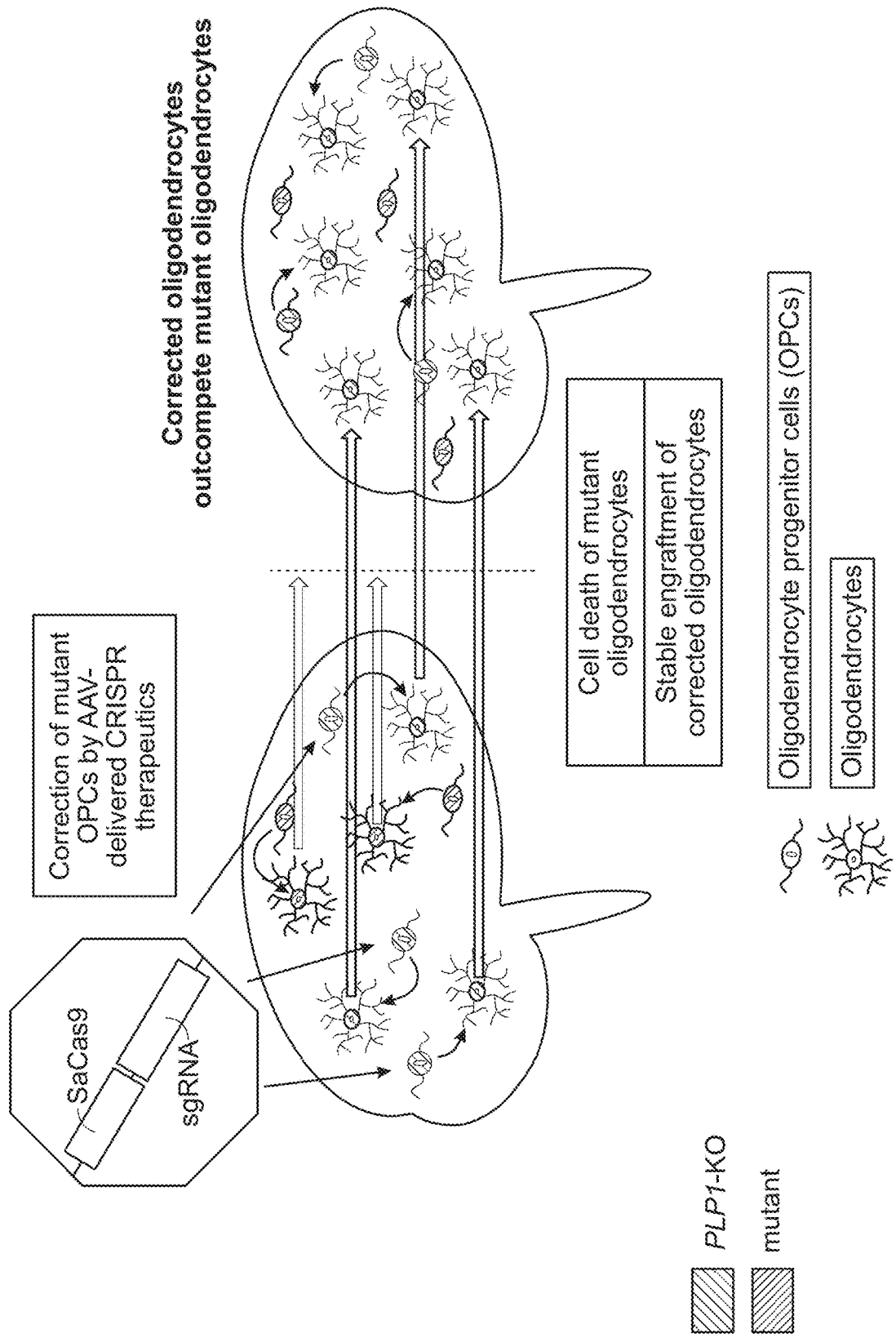
FIG. 12 is a schematic drawing showing one embodiment of the invention where CRISPR-Cas9 mediated gene silencing is delivered to postnatal brain, e.g., through an AAV viral vector encoding SaCas9 and single sgRNA, which can at least partially correct mutant OPCs in a patient's brain. OPCs so corrected will produce oligodendrocytes that in time will outcompete any mutant oligodendrocytes, thus providing sufficiently restored myelination and functions of the patient neurons.

FIG. 12 is a schematic drawing showing one embodiment of the invention where CRISPR-Cas9 mediated gene silencing is delivered to postnatal brain, e.g., through an AAV viral vector encoding SaCas9 and sgRNA, which can at least partially correct mutant OPCs in patient's brain. OPCs so corrected will in time outcompete any mutant OPCs, thus providing sufficiently restored myelination and functions of the patient neurons.

Our strategy bypasses PLP1-related toxicity through inactivation of the PLP1 gene which enhances the ability to make functional myelin. In some instances, neural stem cells, oligodendrocyte progenitor cells (OPCs), or other glial cells in the central nervous system of patients can be edited in situ. In another instance, cells can be modified ex vivo and transplanted to patients.

More specifically, we have demonstrated a novel therapeutic strategy using nuclease-mediated creation of indels in the PLP1 gene or PLP1 genetic regulatory elements to inactivate PLP1 translation or transcription, respectively. We have shown that nuclease-mediated editing of the PLP1 gene in vivo in rodents restores normal function and full lifespan to mice with a severe form of PMD. We demonstrated that this perturbation of PLP1 restores function to PMD model cells in vitro. As part of these proof-of-concept studies CRISPR-Cas9 nuclease with a site directed guide RNA is exemplified but this therapeutic strategy can encompass any site-directed nuclease or gene editing technology.

Development of therapeutics for PMD and other leukodystrophy patients is challenging due to the spectrum of diverse DNA mutations seen in patients. Here, we provide a universal therapeutic for all PMD patients. This single method/product can be used in all PMD patients to effectively inactivate a deleterious, mutant PLP1 gene. Furthermore, inactivation of the PLP1 gene can be beneficial in other myelin disorders to alleviate cell stress in oligodendrocytes. Therefore, there is considerable value in this therapeutic approach and there are strong pharmaceutical and economic interest in pursuing a PLP1-inactivating clinical therapy.

It should be understood that the methods described herein may be carried out in a number of ways and with various modifications and permutations thereof that are well known in the art. It may also be appreciated that any theories set forth as to modes of action should not be construed as limiting this invention in any manner, but are presented such that the methods of the invention can be more fully understood.

All publications and patents mentioned in the above specification are herein incorporated by reference.

Example 2 Post-Natal Inactivation of PLP1 Using AAV Delivery of CRISPR/Cas9

This example demonstrates that post-natal inactivation of PLP1 can be used to effectively treat PMD, or reduce the severity of PMD.

To facilitate the delivery of the CRISPR/Cas9 system with sgRNA targeting the PLP1 locus in a patient, several CNS-targeted AAV serotypes, including PHP.B, were generated, and AAV tropism for OPCs were validated. The AAV constructs (AAV9 or AAV-PHP.B) contain a SaCRISPR-Cas9 nuclease (CMV-SaCas9, SaCas9 coding sequence under the control of a CMV promotor) with a site directed guide RNA (sgRNA) against PLP1 (U6-sgRNA, the sgRNA is under the control of the U6 promotor), which is designed to generate indels in the PLP1 gene and thus prevent expression of the defective PLP1 protein.

Mice were maintained in accordance with approved protocols reviewed by Case Western Reserve University's Institutional Animal Care and Use Committee. Mice were housed in a temperature and humidity controlled housing unit under a 12 hour day/light cycle and were allowed ad libitum access to food.

Jimpy (a severe mouse model of Pelizaeus Merzbacher Disease) mice were then treated via stereotaxic intraventricular injection with the CRISPR-containing AAVs or controls encoding GFP. Specifically, male postnatal day 0 pups were obtained from jimpy breeding pairs and rapidly anesthetized using cryoanesthesia.

A 10 µL Hamilton syringe with a 32 gauge needle was loaded with AAV (AAV9 or AAV-PHP.B) packaging CMV-SaCas9 and U6-sgRNA targeting PLP1. The needle is lowered through the skull to a depth of about 2 mm at a position 2/5 from the intersection of the saggital suture and lambdoid to the eye. 2 µL of viral solution was injected into the lateral ventricle. The injection was then repeated in the contralateral lateral ventricle using the same coordinates, and injection volume for a total delivery of about $1\times10^{10}$-$1\times10^{11}$ vector genomes to the ventricular system. The same was repeated for control mice.

Pups were allowed to recover on a heating pad and then reintroduced to their mother. Pups were monitored daily for phenotype improvement as compared to untreated or vehicle-treated jimpy animals, which develop severe motor phenotype (e.g., intention tremor and seizures) by 2 weeks of age and death by 3 weeks of age.

Treated animals surviving beyond 3 weeks are analyzed using behavioral (e.g., rotarod and open field testing for motor performance, see Example 1 and FIGS. 8 and 9), histology (immunostaining of the CNS for myelin proteins and electron microscopy for myelin ultrastructure, see Example 1 and FIGS. 7 and 11), or daily monitoring for lifespan extension statistical analysis (see Example 1 and FIG. 6).

Further, the spatial requirements for the number of cells required to be edited in the CNS ("dose response" of gene edited cells) are determined to generate a functional response with immunohistochemistry.

Finally, the temporal relationship is explored by introducing an optimized construct at post-natal days P1, P7 and P14.

An optimized CRISPR/Cas9 approach within a defined therapeutic window reduces expression of the mutant PLP1 protein, increases lifespan of treated individual, and restores myelination of axons.

Example 3 Post-Natal Knockdown of PLP1 Using Antisense Oligonucleotides (ASO)

This example demonstrates that post-natal down-regulation or knockdown of PLP1 gene activity using ASO can be used to effectively treat PMD, or reduce the severity of PMD.

Mice are maintained in accordance with approved protocols reviewed by Case Western Reserve University's Institutional Animal Care and Use Committee. Mice are housed in a temperature and humidity controlled housing unit under a 12 hour day/light cycle and are allowed ad libitum access to food.

Male postnatal day 0 pups are obtained from jimpy (a severe mouse model of Pelizaeus Merzbacher Disease) breeding pairs and rapidly anesthetized using cryoanesthesia. A 10 µL Hamilton syringe with a 32 gauge needle is loaded with antisense oligonucleotides targeting PLP1. The needle is lowered through the skull to a depth of about 2 mm at a position 2/5 from the intersection of the saggital suture and lambdoid to the eye. 2 µL of ASO solution is injected into the lateral ventricle. The injection is then repeated in the contralateral lateral ventricle using the same coordinates and injection volume for a total delivery of about 10-75 µg of ASO to the ventricular system.

Pups are allowed to recover on a heating pad and then reintroduced to their mother. Pups are monitored daily for phenotype improvement as compared to untreated or vehicle-treated jimpy animals, which develop severe motor phenotype (e.g., intention tremor and seizures) by 2 weeks of age and death by 3 weeks of age.

Treated animals surviving beyond 3 weeks are analyzed using behavioral (e.g., rotarod and open field testing for motor performance, see Example 1 and FIGS. 8 and 9), histology (immunostaining of the CNS for myelin proteins and electron microscopy for myelin ultrastructure, see Example 1 and FIGS. 7 and 11), or daily monitoring for lifespan extension statistical analysis (see Example 1, and FIG. 6).

Example 4 Post-Natal Knockdown of PLP1 Using RNAi

This example demonstrates that post-natal down-regulation or knockdown of PLP1 gene activity using RNAi can be used to effectively treat PMD, or reduce the severity of PMD.

Mice are maintained in accordance with approved protocols reviewed by Case Western Reserve University's Institutional Animal Care and Use Committee. Mice are housed in a temperature and humidity controlled housing unit under a 12 hour day/light cycle and are allowed ad libitum access to food.

Male postnatal day 0 pups are obtained from jimpy (a severe mouse model of Pelizaeus Merzbacher Disease) breeding pairs and rapidly anesthetized using cryoanesthesia. A 10 µL Hamilton syringe with a 32 gauge needle is loaded with AAV (AAV9 or AAV-PHP.B) packaging CMV-RNAi targeting PLP1 (an RNAi construct that can be transcribed inside the cell under the control of a CMV promotor to generate a functional RNAi molecules, which can then be processed to siRNA/shRNA/miRNA targeting PLP1). Alternatively, the needle is loaded with a non-viral formulation of the RNAi construct targeting PLP1, using non-viral siRNA carriers such as cell-penetrating peptides, polymers, dendrimers, siRNA bioconjugates, and lipid-based siRNA carriers, etc. The needle is lowered through the skull to a depth of about 2 mm at a position 2/5 from the intersection of the saggital suture and lambdoid to the eye. 2 µL of RNAi solution is injected into the lateral ventricle. The injection is then repeated in the contralateral lateral ventricle using the same coordinates and injection volume.

Pups are allowed to recover on a heating pad and then reintroduced to their mother. Pups are monitored daily for phenotype improvement as compared to untreated or vehicle-treated jimpy animals, which develop severe motor phenotype (e.g., intention tremor and seizures) by 2 weeks of age and death by 3 weeks of age.

Treated animals surviving beyond 3 weeks are analyzed using behavioral (e.g., rotarod and open field testing for motor performance, see Example 1 and FIGS. 8 and 9), histology (immunostaining of the CNS for myelin proteins and electron microscopy for myelin ultrastructure, see Example 1 and FIGS. 7 and 11), or daily monitoring for lifespan extension statistical analysis (see Example 1, and FIG. 6).

What is claimed:

1. A method of generating a cell that enhances functional myelin production, the method comprising delivering to the cell an antisense oligonucleotide (ASO) or a polynucleotide encoding said ASO, (1) wherein said ASO decreases expression level of an endogenous PLP1 gene, (2) wherein the cell produces functional myelin, or is a progenitor that produces or differentiates into the cell that produces functional myelin; and (3) wherein the endogenous PLP1 gene is a deleterious disease-causing mutant PLP1 gene.

2. The method of claim 1. wherein the deleterious disease-causing mutant PLP1 gene is a PLP1 gene duplicate.

3. The method of claims 1, wherein the cell, upon delivery of the ASO or the polynucleotide encoding said ASO, exhibits enhanced myelin production.

4. The method of claim 1, wherein the method comprises contacting the cell with a delivery vehicle encoding said ASO.

5. The method of claim 4. wherein the delivery vehicle is an AAV vector, an adenoviral vector, or a lentivirus vector.

6. The method of claim 4, wherein the cell is contacted in vitro, in vivo, or ex vivo.

7. The method of claim 1, wherein the ASO is delivered to the cell in vitro, in vivo, or ex vivo.

8. The method of claim 1. wherein the deleterious disease-causing mutant PLP1 gene is a PLP1 gene point mutation.

* * * * *